United States Patent
Zhou et al.

(10) Patent No.: US 10,086,039 B2
(45) Date of Patent: Oct. 2, 2018

(54) LAMIN A, AN ACTIVATOR OF LONGEVITY/ANTI-AGING SIRT1 PROTEIN

(71) Applicant: THE UNIVERSITY OF HONG KONG, Hong Kong (CN)

(72) Inventors: Zhongjun Zhou, Hong Kong (CN); Baohua Liu, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 14/687,553

(22) Filed: Apr. 15, 2015

(65) Prior Publication Data

US 2016/0067305 A1    Mar. 10, 2016

Related U.S. Application Data

(62) Division of application No. 14/078,010, filed on Nov. 12, 2013, now abandoned.

(60) Provisional application No. 61/725,252, filed on Nov. 12, 2012.

(51) Int. Cl.

| | |
|---|---|
| *A61K 38/16* | (2006.01) |
| *A61K 38/17* | (2006.01) |
| *C12Q 1/37* | (2006.01) |
| *C12Q 1/34* | (2006.01) |
| *A61K 31/05* | (2006.01) |
| *G01N 33/573* | (2006.01) |

(52) U.S. Cl.
CPC .......... *A61K 38/1709* (2013.01); *A61K 31/05* (2013.01); *A61K 38/16* (2013.01); *C12Q 1/34* (2013.01); *C12Q 1/37* (2013.01); *G01N 33/573* (2013.01); *G01N 2333/47* (2013.01); *G01N 2333/91142* (2013.01); *G01N 2333/98* (2013.01); *G01N 2500/02* (2013.01); *G01N 2500/04* (2013.01); *G01N 2500/10* (2013.01)

(58) Field of Classification Search
CPC ........... G01N 2500/04; G01N 2500/02; G01N 2500/10; G01N 33/573; A61K 38/16; A61K 38/17; A61K 38/00; C12Q 1/34
USPC ..................... 514/1.1; 435/18, 375
See application file for complete search history.

(56) References Cited

U.S. PATENT DOCUMENTS

2005/0090438 A1* 4/2005 Brodsky ............ C07K 14/4707
                                                514/16.4
2010/0010099 A1* 1/2010 Chiou .................... A61K 31/05
                                                514/733

OTHER PUBLICATIONS

Liu et al. Dynamics of Lamin-a Processing Following Precursor Accumulation; PLoS One, vol. 5, No. 5 (2010) pp. 1-10.*
Li et al. Resveratrol Inhibits Proliferation and Promotes Apoptosis of Osteosarcoma Cells; European Journal of Pharmacology, vol. 609 (2009) pp. 13-18.*
Lee et al. Functional Proteomics of Resveratrol-Induced Colon Cancer Cell Apoptosis: Caspase-6-Mediated Cleavage of Lamin A is a Major Signaling Loop; Proteomics, vol. 6 (2006) pp. 23-86-2394.*
Deppert, W. SIRT1 Protein Levels in Cancer: Tuning SIRT1 to the Needs of a Cancer Cells; Cell Cycle, vol. 7, No. 19 (2008) pp. 2947-2948.*
Guo et al. Repression of SIRT1 Promotes the Differentiation of Mouse Induced Plutipotent Stem Cells Into Neural Stem Cells; Cell Mol Neurobiol, vol. 34 (2014) pp. 905-912.*
Hu et al. Efficient Production of Chimeric Mice From Embryonic Stem Cells Injected Into 4-to 8-Cell and Blastocyst Embryos; Journal of Animal Science and Biotechnology; vol. 4, No. 12 (2013) pp. 1-7.*
Liu et al. Resveratrol Rescues SIRT1-Dependent Adult Stem Cell Decline and Alleviates Progeroid Features in Laminopathy-Based Progeria; Cell Metabolism, vol. 16 (2012) pp. 738-750.*
Saunders et al. MIRNAS Regulate SIRT1 Expression During Mouse Embryonic Stem Cell Differentiation and in Adult Mouse Tissues; Aging, vol. 2, No. 7 (2010) pp. 415-431.*
Soleimani et al. A Protocol for Isolation and Culture of Mesenchymal Stem Cells From Mouse Bone Marrow; Nature Protocols, vol. 4, No. 1 (2009) pp. 102-106.*
Yang et al. Treatment With a Farnesyltransferase Inhibitor Improves Survival in Mice With a Hutchinson-Gilford Progeria Syndrome Mutation; Biochim Biophys Acta, vol. 1781, No. 1-2 (2008) pp. 36-39.*
Yuan et al. SIRT1 is Required for Long-Term Growth of Human Mesenchymal Stem Cells; Journal of Molecular Medicine, vol. 90 (2012) pp. 389-400.*
Ullah et al. Human Mesenchymal Stem Cells-Current Trends and Future Prospective; Bioscience Reports, vol. 35 (2015) pp. 1-18.*
Zuo et al., Influences of Lamin A Levels on Induction of Pluripotent Stem Cells, Biology Open, Sep. 7, 2012, pp. 1118-1127, vol. 1.
Witowski et al., Conversion of a Beta-Ketoacyl Synthase to a Malonyl Decarboxylase by Replacement of the Active-Site Cysteine with Glutamine, Biochemistry, 1999, pp. 11643-11650, vol. 38.
Whisstock et al., Prediction of Protein Function from Protein Sequence and Structure, Quarterly Reviews of Biophysics, 2003, pp. 307-340, vol. 36.
Chica et al., Semi-Rational Approaches to Engineering Enzyme Activity: Combining the Benefits of Directed Evolution and Rational Design, Current Opinion in Biotechnology, 2005, pp. 378-384, vol. 16.

(Continued)

*Primary Examiner* — Scott Long
*Assistant Examiner* — Paul C Martin
(74) *Attorney, Agent, or Firm* — Saliwanchik, Lloyd & Eisenschenk

(57) ABSTRACT

In one embodiment, the present invention provides methods of modulating the deacetylase activity of SIRT1 in one or more cell by modifying the binding affinity of lamin A to SIRT1 via one or more interaction modifying compound. In another embodiment, the present invention provides methods of screening SIRT1-activating/inhibiting compounds based on the interaction between lamin A and SIRT1 proteins and SIRT1-activating property of lamin A. In another embodiment, the present invention provides uses of SIRT1-activating compounds to treat patient(s) suffering from metabolic and/or aging-related degenerative diseases, and uses of SIRT1-inhibiting compounds to treat human malignancies.

4 Claims, 29 Drawing Sheets

Specification includes a Sequence Listing.

(56) References Cited

OTHER PUBLICATIONS

Lee et al., Sirtuin1 Facilitates Generation of Induced Pluripotent Stem Cells from Mouse Embryonic Fibroblasts through the miR-34A and p53 Pathways, Plos One, 2012, pp. 1-13, vol. 7, No. 9.
Office Action dated Dec. 15, 2014 in U.S. Appl. No. 14/078,010.
Villalba, J. M. et al., A patent review of sirtuin activators: an update, Expert Opinion on Therapeutic Patents, 2012, 22(4):355-367, 2012 Informa UK, Ltd.
Varela, I. et al., Accelerated ageing in mice deficient in Zmpste24 protease is linked to p53 signalling activation, Nature, Sep. 22, 2005, 437:564-568, 2005 Nature Publishing Group.
Kim, J. et al., DBC1 is a negative regulator of SIRT1, Nature, Jan. 31, 2008, 451:583-587, 2008 Nature Publishing Group.
Manju, K. et al., Expression of disease-causing lamin A mutants impairs the formation of DNA repair foci, Journal of Cell Science, 2006, 119(13):2704-2714, The Company of Biologists 2006.
Liu, B. et al., Genomic instability in laminopathy-based premature aging, Nature Medicine, Jul. 2005, 11(7):780-785, 2005 Nature Publishing Group.
Phair, R. D. et al., High mobility of proteins in the mammalian cell nucleus, Nature, Apr. 6, 2000, 404:604-609, 2002 Macmillan Magazines Ltd.
Glynn, M. W. et al., Incomplete processing of mutant lamin A in Hutchinson-Gilford progeria leads to nuclear abnormalities, which are reversed by farnesyltransferase inhibition, Human Molecular Genetics, 2005, 14(20):2959-2969, The Author 2005, Oxford University Press.
Chen, D. et al., Increase in Activity During Calorie Restriction Requires Sirt 1, Science, Dec. 9, 2005, 310(5754):1641.
Tissenbaum, H. A. et al., Increased dosage of a sir-2 gene extends lifespan in *Caenorhabditis elegans*, Nature, Mar. 8, 2001, 410:227-230, 2001 Macmillan Magazines Ltd.
Rodgers, J. T. et al., Nutrient control of glucose homeostasis through a complex of PGC-1α and SIRT1, Nature, Mar. 3, 2005, 434:113-118, 2005 Nature Publishing Group.
Eriksson, M. et al., Recurrent de novo point mutations in lamin A cause Hutchinson-Gilford progeria syndrome, Nature, May 15, 2003, 423:293-298, 2003 Nature Publishing Group.
Tissenbaum, H. A. et al., Regulation of *Caenorhabditis elegans* lifespan by sir-2.1 transgenes, Nature, Sep. 22, 2011, 477:E1-E2, 2011 Macmillan Publishers Limited.
Wood, J. G. et al., Sirtuin activators mimic caloric restriction and delay ageing in metazoans, Nature, Aug. 5, 2004, 430:1-5, 2004 Nature Publishing Group.
Chalkiadaki, A. et al., Sirtuins mediate mammalian metabolic responses to nutrient availability, Nature Reviews, Endocrinology, May 2012, 8:287-296, 2012 Macmillan Publishers Limited.
Lavu, S. et al., Sirtuins-novel therapeutic targets to treat age-associated diseases, Nature Reviews, Drug Discovery, Oct. 2008, 7:1-14, 2009 Macmillan Publishers Limited.
Howitz, K. T. et al., Small molecule activators of sirtuins extend *Saccharomyces cerevisiae* lifespan, Nature, Sep. 11, 2003, 425:191-196, 2003 Nature Publishing Group.
Agarwal, B., et al., Resveratrol and life extension, Annals of the New York Academy of Sciences, 2011, 1215:138-143, New York Academy of Sciences.
Alcendor, R. R., et al., Sirt1 Regulates Aging and Resistance to Oxidative Stress in the Heart, Circulation Research, May, 25, 2007, 100:1512-1521, American Heart Association, Inc.
Banks, A. S., et al., SirT1 Gain of Function Increases Energy Efficiency and Prevents Diabetes in Mice, Cell Metabolism, Oct. 8, 2008, 8:333-341, Elsevier Inc.
Barger, J. L., et al., Short-term consumption of a resveratrol-containing nutraceutical mixture mimics gene expression of long-term caloric restriction in mouse heart, Experimental Gerontology, 2008, 43:859-866, Elsevier Inc.
Baur, J. A., Biochemical Effects of SIRT1 Activators, Biochimica et Biophysica Acta, Aug. 2010, 1804(8):1626-1634, 2009 Elsevier B.V.
Baur, J. A., et al., Resveratrol improves health and survival of mice on a high-calorie diet, Nature, Nov. 16, 2006, 444(7117):337-342.
Beher, D., et al., Resveratrol is Not a Direct Activator of SIRT1 Enzyme Activity, Chemical Biology & Drug Design, 2009, 74:619-624, John Wiley & Sons A/S.
Blencowe, B. J., et al., Association of Nuclear Matrix Antigens with Exon-containing Splicing Complexes, The Journal of Cell Biology, Nov. 1994,127(3):593-607, The Rockefeller University Press.
Bordone, L., et al., SIRT1 transgenic mice show phenotypes resembling calorie restriction, Aging Cell, 2007, 6:759-767, Blackwell Publishing Ltd/Anatomical Society of Great Britain and Ireland.
Borra, M. T., et al., Mechanism of Human SIRT1 Activation by Resveratrol, The Journal of Biological Chemistry, Apr. 29, 2005, 280(17):17187-17195, The American Society for Biochemistry and Molecular Biology, Inc., USA.
Brunet, A. et al., Stress-Dependent Regulation of FOXO Transcription Factors by the SIRT1 Deacetylase, Science, Mar. 26, 2004, 303:2011-2015, American Association for the Advancement of Science, Washington, DC.
Burnett, C., et al., Absence of effects of Sir2 over-expression on lifespan in *C. elegans and Drosophila*, Nature, Sep. 21, 2011, 477(7365):482-485.
Burtner, C. R., et al., Progeria syndromes and ageing: what is the connection?, Nature Reviews, Molecular Cell Biology, Aug. 2010, 11:567-578, Macmillan Publishers Limited.
Candelario, J., et al., Perturbation of wild-type lamin A metabolism results in a progeroid phenotype, Aging Cell, Jun. 2008, 7(3):355-367.
Cantó, C., et al., AMPK regulates energy expenditure by modulating $NAD^+$ metabolism and SIRT1 activity, Nature, Apr. 23, 2009, 458(7241):1056-1060.
Cao, K., et al., Progerin and telomere dysfunction collaborate to trigger cellular senescence in normal human fibroblasts, The Journal of Clinical Investigation, Jul. 2011, 121(7):2833-2844.
Capell, B. C., et al., Inhibiting farnesylation of progerin prevents the characteristic nuclear blebbing of Hutchinson-Gilford progeria syndrome, Proceedings of the National Academy of Sciences of the United States of America, Sep. 6, 2005, 102(36):12879-12884, The National Academy of Sciences of the USA.
Cheng, H., et al., Developmental defects and p53 hyperacetylation in Sir2 homolog (SIRT1)-deficient mice, Proceedings of the National Academy of Sciences of the United States of America, Sep. 16, 2003, 100(19):10794-10799, The National Academy of Sciences of the USA.
Dai, H., et al., SIRT1 Activation by Small Molecules Kinetic and Biophysical Evidence for Direct Interaction of Enzyme and Activator, The Journal of Biological Chemistry, Oct. 22, 2010, 285(43):32695-32703, The American Society for Biochemistry and Molecular Biology, Inc., USA.
Deng, C., SIRT1, Is it a Tumor Promoter or Tumor Suppressor?, International Journal of Biological Sciences, 2009, 5(2):147-152, Ivyspring International Publisher.
Denu, J. M., The Sir2 family of protein deacetylases, Current Opinion in Chemical Biology, 2005, 9:431-440, Elsevier Ltd.
Donmez, G., et al., Aging and disease: connections to sirtuins, Aging Cell, 2010, 9:285-290, Blackwell Publishing Ltd/Anatomical Society of Great Britain and Ireland.
Downes, M., et al., Identification of a nuclear domain with deacetylase activity, Proceedings of the National Academy of Sciences of the United States of America, Sep. 12, 2000, 97(19):10330-10335.
Espada, J., et al., Nuclear envelope defects cause stem cell dysfunction in premature-aging mice, The Journal of Cell Biology, Apr. 7, 2008, 181(1):27-35.
Finkel, T., et al., Recent progress in the biology and physiology of sirtuins, Nature, Jul. 30, 2009, 460(7255):587-591, Macmillan Publishers Limited.
Fong, L. G., et al., A Protein Farnesyltransferase Inhibitor Ameliorates Disease in a Mouse Model of Progeria, Science, Mar. 17, 2006, 311(5767), 1621-1623, American Association for the Advancement of Science, Washington DC.
Fong, L. G., et al., Heterozygosity for Lmna deficiency eliminates the progeria-like phenotypes in Zmpste24-deficient mice, Proceed-

(56) References Cited

OTHER PUBLICATIONS ings of the National Academy of Sciences of the United States of America, Dec. 28, 2004, 101(52):18111-18116, The National Academy of Sciences of the USA.

Gledhill, J. R., et al., Mechanism of inhibition of bovine $F_1$-ATPase by resveratrol and related polyphenols, Proceedings of the National Academy of Sciences of the United States of America, Aug. 21, 2007, 104(34):13632-13637, The National Academy of Sciences of the USA.

Goodarzi, A. A., et al., ATM Signaling Facilitates Repair of DNA Double-Strand Breaks Associated with Heterochromatin, Molecular Cell, Jul. 25, 2008, 31:167-177, Elsevier Inc.

Gu, W., et al., Activation of p53 Sequence-Specific DNA Binding by Acetylation of the p53 C-Terminal Domain, Cell, Aug. 22, 1997, 90:595-606, Cell Press.

Haigis, M. C., et al., Mammalian Sirtuins: Biological Insights and Disease Relevance, Annual Review of Pathology, 2010, 5:253-295, Annual Reviews.

Han, M., et al., SIRT1 regulates apoptosis and Nanog expression in mouse embryonic stem cells by controlling p53 subcellular localization, Cell Stem Cell, Mar. 6, 2008, 2(3):1-17.

Harikumar, K. B., et al., Resveratrol: A multitargeted agent for age-associated chronic diseases, Cell Cycle, 2008, 7(8):1020-1035, Landes Bioscience, Taylor & Francis Group.

Hawley, S. A., et al., Use of Cells Expressing γ Subunit Variants to Identify Diverse Mechanisms of AMPK Activation, Cell Metabolism, Jun. 9, 2010, 11:554-565, Elsevier Inc.

Hendzel, M. J., et al., Histone Deacetylase Is a Component of the Internal Nuclear Matrix, The Journal of Biological Chemistry, Nov. 15, 1991, 266(32):21936-21942, The American Society for Biochemistry and Molecular Biology, Inc., USA.

Herranz, D., et al., Sirt1 improves healthy ageing and protects from metabolic syndrome-associated cancer syndrome, Nature Communications, Apr. 12, 2010, 1(3):1-17.

Houtkooper, R. H., et al., Sirtuins as regulators of metabolism and healthspan, Nature Reviews, Molecular Cell Biology, Apr. 2012, 13:225-238, Macmillan Publishers Limited.

Kaeberlein, M., et al., Substrate-specific Activation of Sirtuins by Resveratrol, The Journal of Biological Chemistry, Apr. 29, 2005, 280(17), 17038-17045, The American Society for Biochemistry and Molecular Biology, Inc., USA.

Kim, E., et al., Active Regulator of SIRT1 Cooperates with SIRT1 and Facilitates Suppression of p53 Activity, Molecular Cell, Oct. 26, 2007, 28:277-290, Elsevier Inc.

Klar, A. J. S., et al., MAR1-A Regulator of the HMa and HMα Loci in *Saccharomyces Cerevisiae*, Genetics, Sep. 1979, 93:37-50.

Krishnan, V., et al., Histone H4 lysine 16 hypoacetylation is associated with defective DNA repair and premature senescence in Zmpste24-deficient mice, Proceedings of the National Academy of Sciences of the United States of America, Jul. 26, 2011, 108(30):12325-12330.

Kruhlak, M. J., et al., Reduced Mobility of the Alternate Splicing Factor (ASF) through the Nucleoplasm and Steady State Speckle Compartments, The Journal of Cell Biology, Jul. 10, 2000, 150(1):41-51, The Rockefeller University Press.

Kudlow, B. A., et al., Suppression of Proliferative Defects Associated with Processing-defective Lamin A Mutants by hTERT or Inactivation of p53, Molecular Biology of the Cell, Dec. 2008, 19:5238-5248, The American Society for Cell Biology.

Lee, H., et al., Expression of DBC1 and SIRT1 is associated with poor prognosis for breast carcinoma, Human Pathology, 2011, 42:204-213, Elsevier Inc.

Li, L., et al., Activation of p53 by SIRT1 inhibition enhances elimination of CML leukemia stem cells in combination with imatinib, Cancer Cell, Feb. 14, 2012, 21(2):266-281, 2011 Elsevier Inc.

Li, W., et al., Properties of chicken erythrocyte histone deacetylase associated with the nuclear matrix, Biochemical Journal, 1996, 314:631-637, Great Britain.

Lin, F., et al., Structural Organization of the Human Gene Encoding Nuclear Lamin A and Nuclear Lamin C, The Journal of Biological Chemistry, Aug. 5, 1993, 268(22):16321-16326, The American Society for Biochemistry and Molecular Biology, Inc., USA.

Liu, B., et al., Lamin A/C, laminopathies and premature ageing, Histology and Histopathology, 2008, 23:747-763.

Liu, Y., et al., Involvement of Xeroderma Pigmentosum Group A (XPA) in Progeria Arising from Defective Maturation of Prelamin A, Federation of American Societies for Experimental Biology Journal, Feb. 2008, 22(2):603-611.

Lombard, D. B., et al., Longevity hits a roadblock, Nature, Sep. 22, 2011, 477:410-411, Macmillan Publishers Limited.

Mantel, C. R., et al., Sirt1, Notch and stem cell "age asymmetry", Cell Cycle, Sep. 15, 2008, 7(18):2821-2825, Landes Bioscience, Taylor & Francis Group.

Mcburney, M. W., et al., The Mammalian SIR2α Protein Has a Role in Embryogenesis and Gametogenesis, Molecular and Cellular Biology, Jan. 2003, 23(1):38-54, American Society for Microbiology.

McClintock, D., et al., The Mutant Form of Lamin A that Causes Hutchinson-Gilford Progeria Is a Biomarker of Cellular Aging in Human Skin, PLoS One, Dec. 2007, e1269(12):1-10.

Méndez, J., et al., Chromatin Association of Human Origin Recognition Complex, Cdc6, and Minichromosome Maintenance Proteins during the Cell Cycle: Assembly of Prereplication Complexes in Late Mitosis, Molecular and Cellular Biology, Nov. 2000, 20(22):8602-8612, American Society for Microbiology.

Milne, J. C., et al., Small molecule activators of SIRT1 as therapeutics for the treatment of type 2 diabetes, Nature, Nov. 29, 2007, 450(7170):712-716, Nature Publishing Group.

Pacholec, M., et al., SRT1720, SRT2183, SRT1460, and Resveratrol Are Not Direct Activators of SIRT1, The Journal of Biological Chemistry, Mar. 12, 2010, 285(11):8340-8351, the American Society for Biochemistry and Molecular Biology, Inc., USA.

Park, S., et al., Resveratrol Ameliorates Aging-Related Metabolic Phenotypes by Inhibiting cAMP Phosphodiesterases, Cell, Feb. 3, 2012, 148(3):421-433, Elsevier Inc.

Pendás, A. M., et al., Defective prelamin a processing and muscular and adipocyte alterations in Zmpste24 metalloproteinase-deficient mice, nature genetics, May 2002, 31:94-99, Nature Publishing Group.

Pfluger, P. T., et al., Sirt1 protects against high-fat diet-induced metabolic damage, Proceedings of the National Academy of Sciences of the United States of America, Jul. 15, 2008, 105(28):97939798, The National Academy of Sciences of the USA.

Picard, F., et al., Sirt1 promotes fat mobilization in white adipocytes by repressing PPAR-γ, Nature, Jun. 17, 2004, 429(6993):1-14, Nature Publishing Group.

Price, N. L., et al., SIRT1 is required for AMPK activation and the beneficial effects of resveratrol on mitochondrial function, Cell Metabolism, May 2, 2012, 15(5):675-690, Elsevier Inc.

Rusiñol, A. E., et al., Farnesylated lamins, progeroid syndromes and farnesyl transferase inhibitors, Journal of Cell Science, 2006, 119(16):3265-3272, The Company of Biologists.

Ryan, R. F., et al., KAP-1 Corepressor Protein Interacts and Colocalizes with Heterochromatic and Euchromatic HP1 Proteins: a Potential Role for Krüppel-Associated Box-Zinc Finger Proteins in Heterochromatin-Mediated Gene Silencing, Molecular and Cellular Biology, Jun. 1999, 19(6):4366-4378, American Society for Microbiology.

Scaffidi, P., et al., Reversal of the cellular phenotype in the premature aging disease Hutchinson-Gilford Progeria Syndrome, Nature Medicine, Apr. 2005, 11(4):440-445.

Scaffidi, P., et al., Lamin A-Dependent Nuclear Defects in Human Aging, Science, May 19, 2006, 312(5776):1059-1063.

Scaffidi, P., et al., Lamin A-dependent misregulation of adult stem cells associated with accelerated ageing, Nature Cell Biology, Apr. 2008, 10(4):452-459.

Sgambato, A., et al., Resveratrol, a natural phenolic compound, inhibits cell proliferation and prevents oxidative DNA damage, Mutation Research, 2001, 496:171-180, Elsevier Science B.V.

Smith, B. C., et al., Mechanisms and Molecular Probes of Sirtuins, Chemistry Biology, Oct. 20, 2008, 15(10):1002-1013.

(56) References Cited

OTHER PUBLICATIONS

Sun, C., et al., SIRT1 Improves Insulin Sensitivity under Insulin-Resistant Conditions by Repressing PTP1B, Cell Metabolism, Oct. 2007, 6:307-319, Elsevier Inc.

Timmers, S., et al., Calorie restriction-like effects of 30 days of Resveratrol (resVida™) supplementation on energy metabolism and metabolic profile in obese humans, Cell Metabolism, Nov. 2, 2011, 14(5):1-22.

Toth, J. I., et al., Blocking protein farnesyltransferase improves nuclear shape in fibroblasts from humans with progeroid syndromes, Proceedings of the National Academy of Sciences of the United States of America, Sep. 6, 2005, 102(36):12873-12878, The National Academy of Sciences of the USA.

Valenzano, D. R., et al., Resveratrol Prolongs Lifespan and Retards the Onset of Age-Related Markers in a Short-Lived Vertebrate, Current Biology, Feb. 7, 2006, 16:296-300, Elsevier Ltd.

Varela, I., et al., Combined treatment with statins and aminobisphonates extends longevity in a mouse model of human premature aging, Nature Medicine, Jul. 2008, 14(7):767-772, Nature Publishing Group.

Viswanathan, M., et al., Regulation of *Caenorhabditis elegans* lifespan by sir-2.1 transgenes, Nature, Sep. 22, 2011, 477:E1-E2, Macmillan Publishers Limited.

Viswanathan, M., et al., A Role for SIR-2.1 Regulation of ER Stress Response Genes in Determining *C. elegans* Life Span, Developmental Cell, Nov. 2005, 9:605-615, Elsevier Inc.

Wang, R., et al., Impaired DNA damage response, genome instability, and tumorigenesis in SIRT1 mutant mice, Cancer Cell, Oct. 7, 2008, 14(4):312-323.

Zhao, W., et al., Negative regulation of the deacetylase SIRT1 by DBC1, Nature, Jan. 31, 2008, 451(7178):587-590.

Luo, J., et al., Negative Control of p53 by Sirα Promotes Cell Survival under Stress, Cell, Oct. 19, 2001, 107:137-148, Cell Press.

Pearson, K. J., et al., Resveratrol Delays Age-Related Deterioration and Mimics Transcriptional Aspects of Dietary Restriction without Extending Life Span, Cell Metabolism, Aug. 6, 2008, 8:157-168, Elsevier Inc.

Hudson, P. J., et al., High avidity scFv multimers; diabodies, and triabodies, Journal of Immunological Methods, 1999, 231:177-189, Elsevier Science B.V.

Köhler, G., et al., Continuous cultures of fused cells secreting antibody of predefined specificity, Nature, Aug. 7, 1975, 256:495-497, Nature Publishing Group.

Niman, H. L., et al., Generation of protein-reactive antibodies by short peptides is an event of high frequency: Implications for the structural basis of immune recognition, Proceedings of the National Academy of Sciences of the United States of America, Aug. 1983, 80:4949-4953.

Harlow, E., et al., antibodies a Laboratory Manual, 1988, 2 pages, Cold Spring Harbor Laboratory.

Sastry, L., et al., Cloning of the immunological repertoire in *Escherichia coli* for generation of monoclonal catalytic antibodies: Construction of a heavy chain variable region-specific cDNA library, Proceedings of the National Academy of Sciences of the United States of America, Aug. 1989, 86:5728-5732.

Huse, W. D., et al., Generation of a Large Combinatorial Library of the Immunoglobulin Repertoire in Phage Lambda, Science, Dec. 8, 1989, 246(4935):1275-1281, American Association for the Advancement of Science, Washington DC.

Berezney, R., et al., The Nuclear Matrix: A Structural Milieu for Genomic Function, International Review of Cytology, 1995, 162A:1-65, Academic Press, Inc.

\* cited by examiner

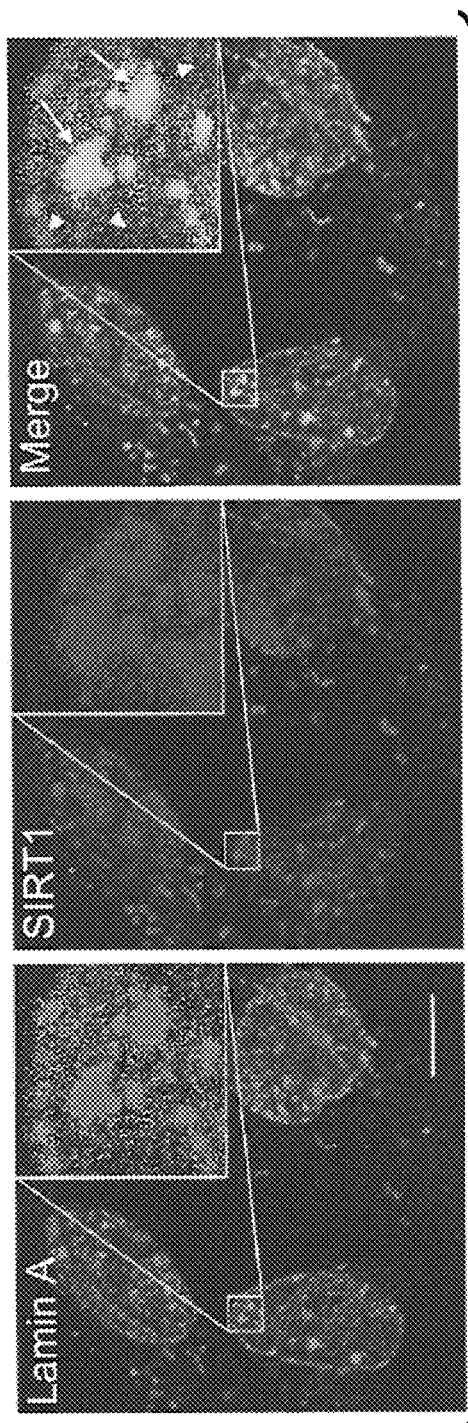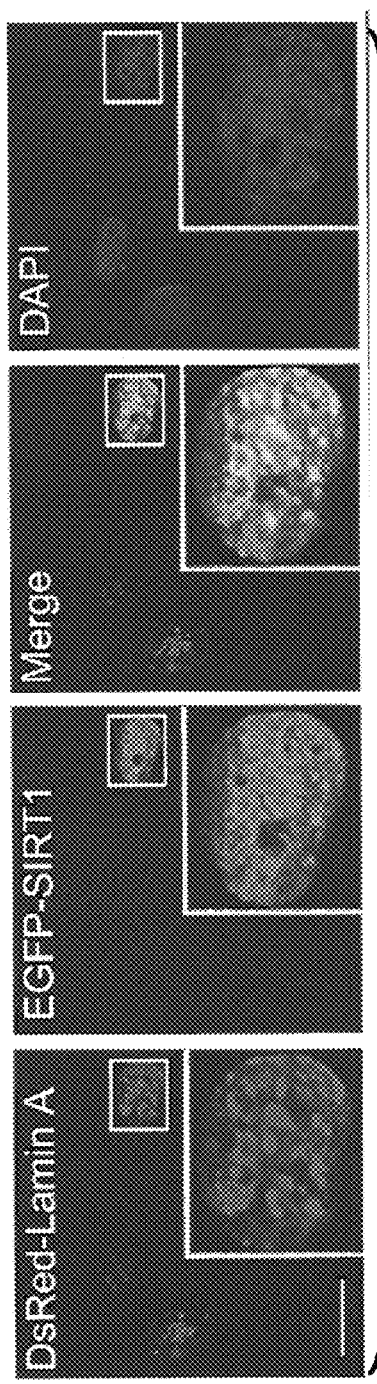

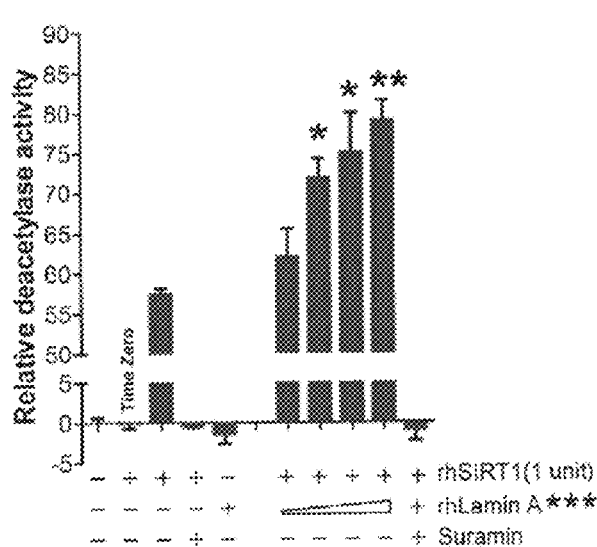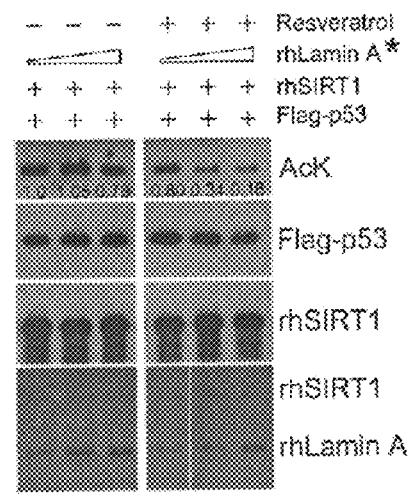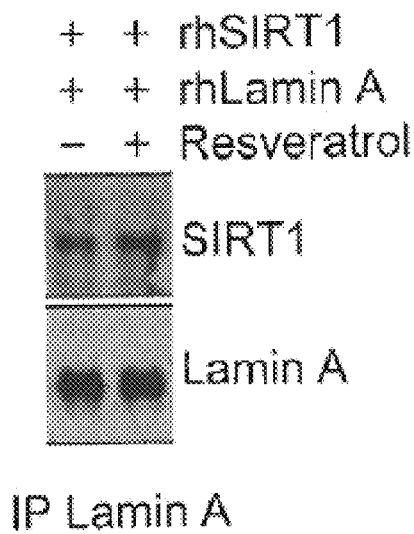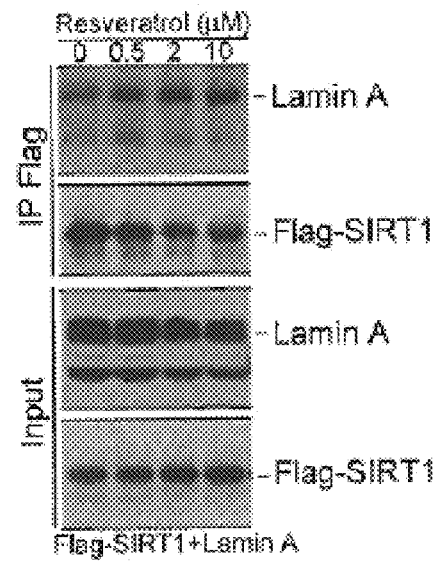
FIG. 3A  FIG. 3B
FIG. 3C  FIG. 3D

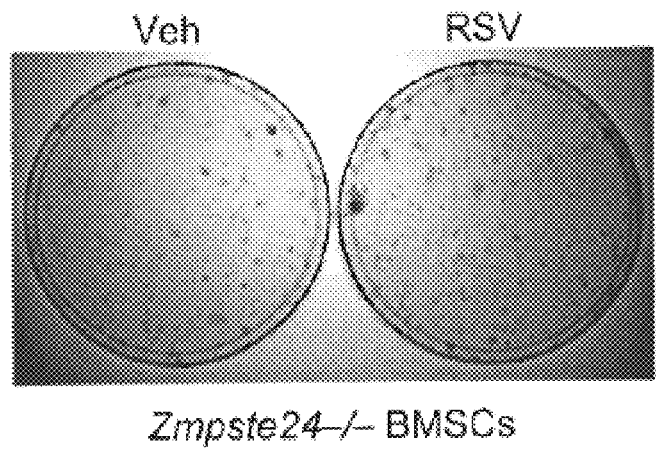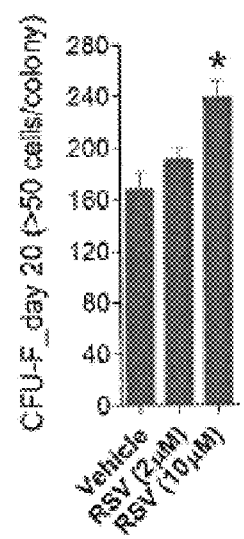
FIG. 4A          FIG. 4B
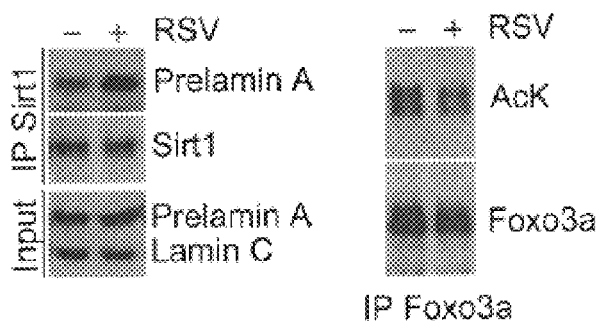
FIG. 4C
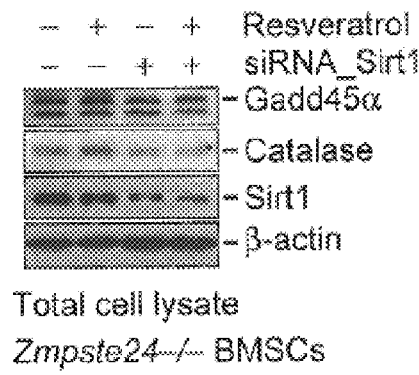
FIG. 4D

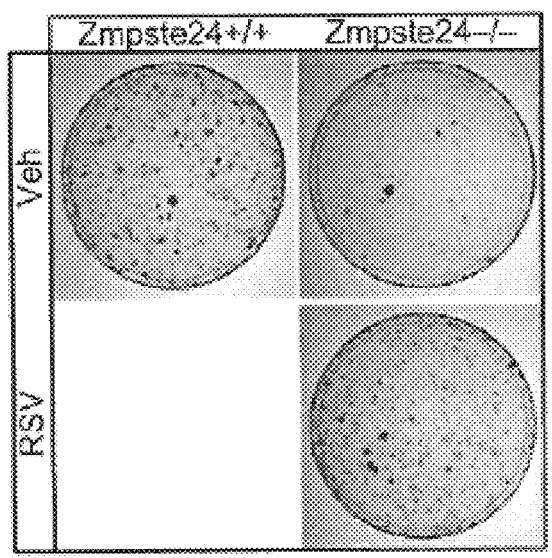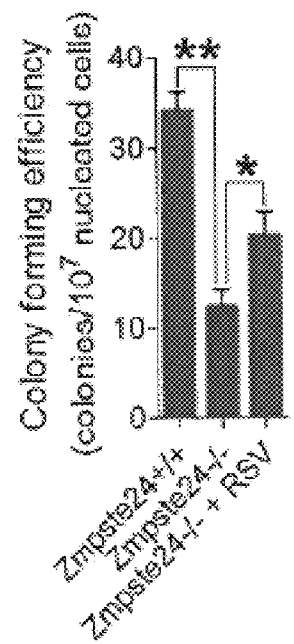
FIG. 5A    FIG. 5B
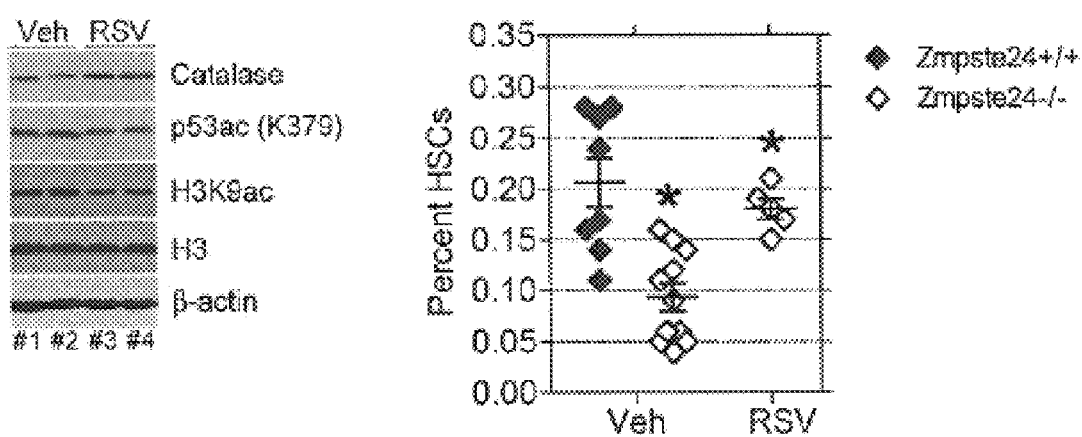
FIG. 5C    FIG. 5D

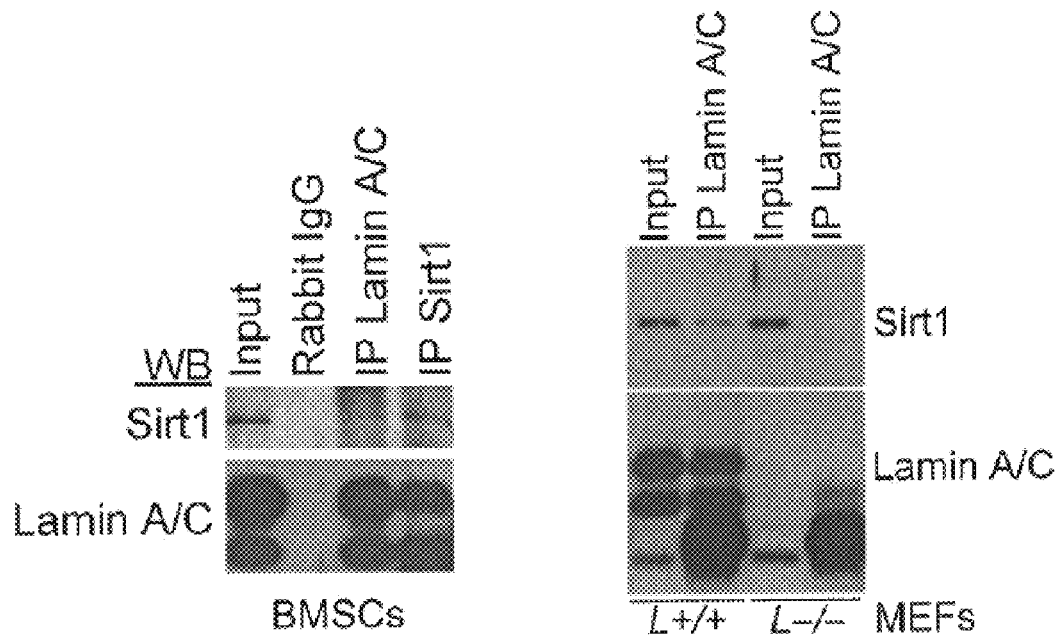
FIG. 6A
FIG. 6B
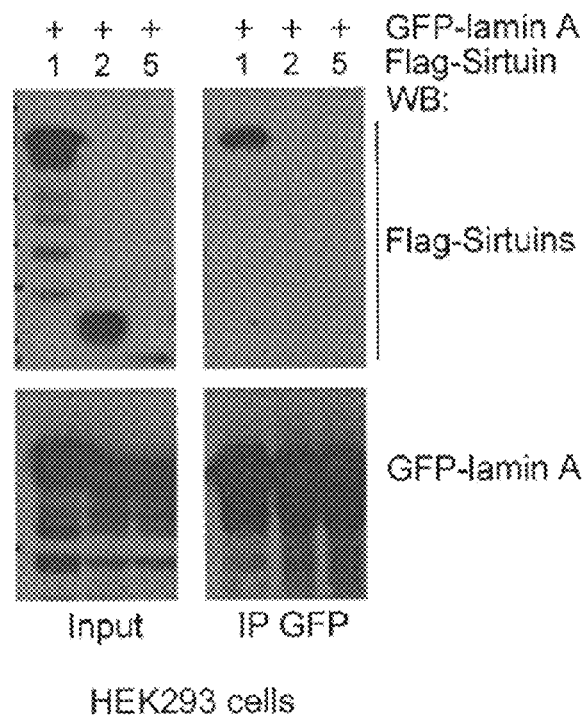
FIG. 6C

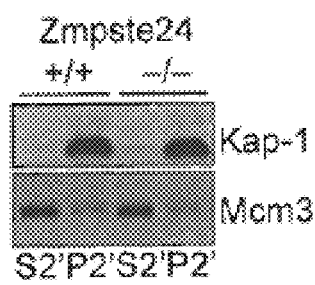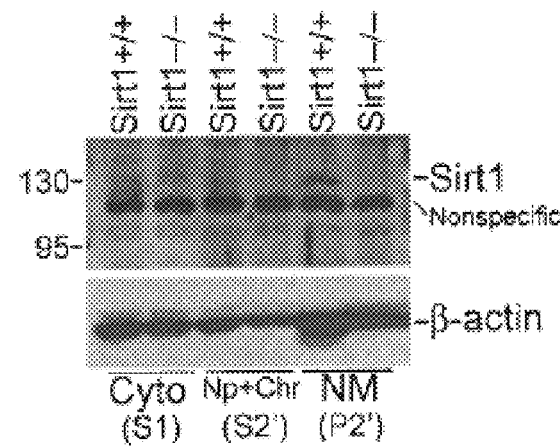
FIG. 7A          FIG. 7B
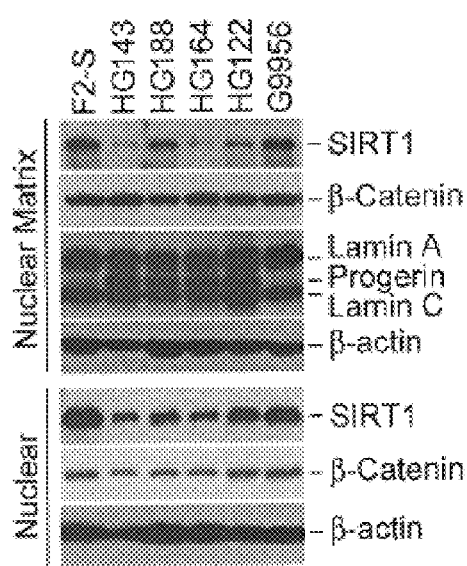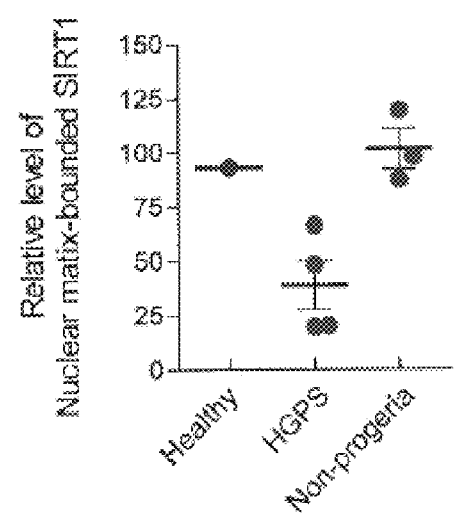
FIG. 7C          FIG. 7D

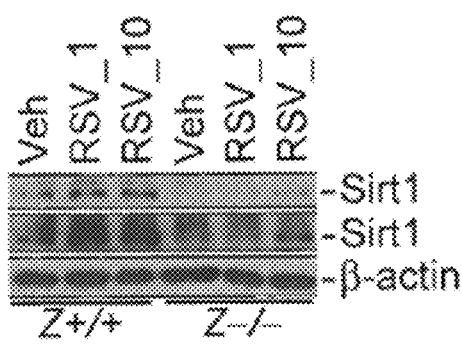
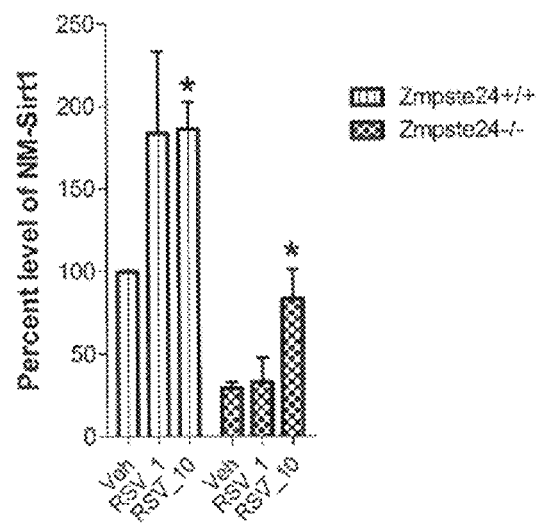
FIG. 7G　　　　　　　FIG. 7H
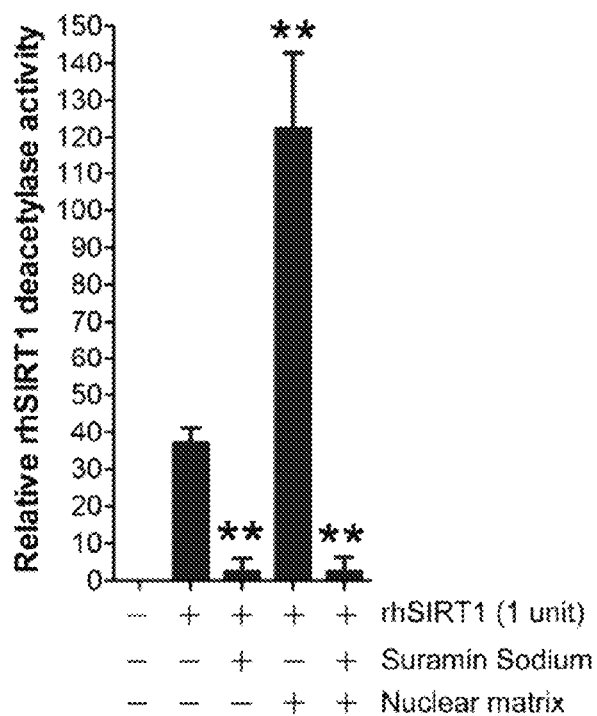
FIG. 7I

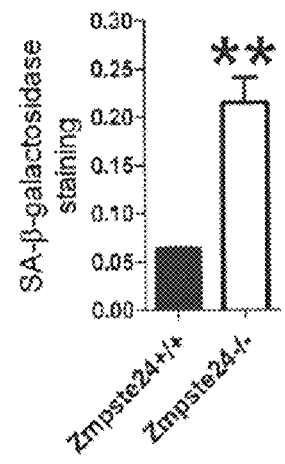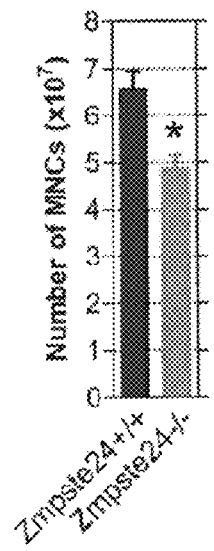
FIG. 9D    FIG. 9E
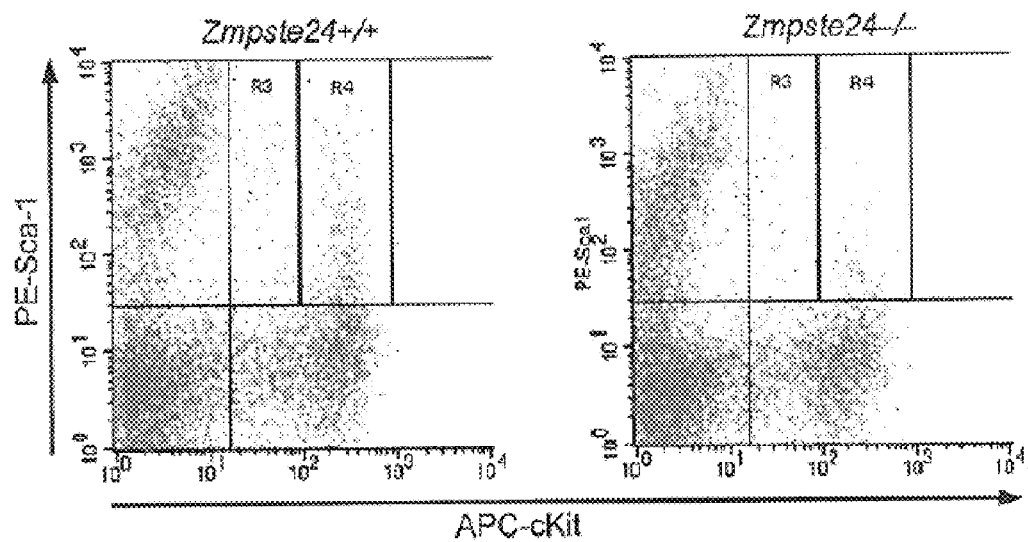
FIG. 9F

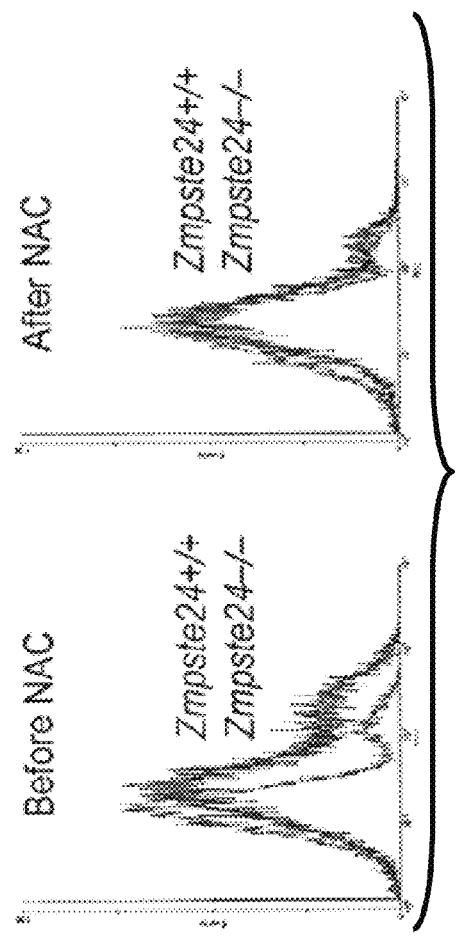
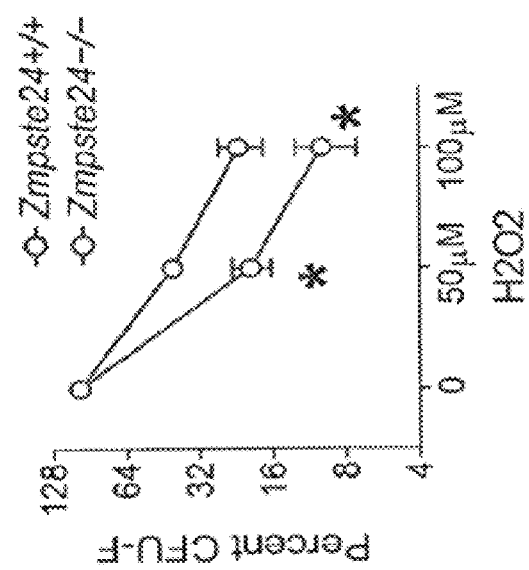
FIG. 10B
FIG. 10A

SEQUENCE LISTING

<160> NUMBER OF SEQ ID NOS: 2

<210> SEQ ID NO 1
<211> LENGTH: 4
<212> TYPE: PRT

```
<213> ORGANISM: Homo sapiens
<220> FEATURE:
<221> NAME/KEY: Acetylation
<222> LOCATION: (1)..(1)
<220> FEATURE:
<221> NAME/KEY: Acetylation
<222> LOCATION: (4)..(4)

<400> SEQUENCE: 1

Arg His Lys Lys
1

<210> SEQ ID NO 2
<211> LENGTH: 664
<212> TYPE: PRT
<213> ORGANISM: Homo sapiens

<400> SEQUENCE: 2

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
                20                  25                  30

Glu Asp Leu Gln Glu Leu Asn Asp Arg Leu Ala Val Tyr Ile Asp Arg
            35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
```

```
            305                 310                 315                 320
        Arg Asp Leu Glu Asp Ser Leu Ala Arg Glu Arg Asp Thr Ser Arg Arg
                        325                 330                 335

Leu Leu Ala Glu Lys Glu Arg Glu Met Ala Glu Met Arg Ala Arg Met
                        340                 345                 350

Gln Gln Gln Leu Asp Glu Tyr Gln Glu Leu Leu Asp Ile Lys Leu Ala
                        355                 360                 365

Leu Asp Met Glu Ile His Ala Tyr Arg Lys Leu Leu Glu Gly Glu Glu
                        370                 375                 380

Glu Arg Leu Arg Leu Ser Pro Ser Pro Thr Ser Gln Arg Ser Arg Gly
        385                 390                 395                 400

Arg Ala Ser Ser His Ser Ser Gln Thr Gln Gly Gly Gly Ser Val Thr
                        405                 410                 415

Lys Lys Arg Lys Leu Glu Ser Thr Glu Ser Arg Ser Ser Phe Ser Gln
                        420                 425                 430

His Ala Arg Thr Ser Gly Arg Val Ala Val Glu Glu Val Asp Glu Glu
                        435                 440                 445

Gly Lys Phe Val Arg Leu Arg Asn Lys Ser Asn Glu Asp Gln Ser Met
                        450                 455                 460

Gly Asn Trp Gln Ile Lys Arg Gln Asn Gly Asp Asp Pro Leu Leu Thr
        465                 470                 475                 480

Tyr Arg Phe Pro Pro Lys Phe Thr Leu Lys Ala Gly Gln Val Val Thr
                        485                 490                 495

Ile Trp Ala Ala Gly Ala Gly Ala Thr His Ser Pro Pro Thr Asp Leu
                        500                 505                 510

Val Trp Lys Ala Gln Asn Thr Trp Gly Cys Gly Asn Ser Leu Arg Thr
                        515                 520                 525

Ala Leu Ile Asn Ser Thr Gly Glu Glu Val Ala Met Arg Lys Leu Val
                        530                 535                 540

Arg Ser Val Thr Val Val Glu Asp Asp Glu Asp Glu Asp Gly Asp Asp
        545                 550                 555                 560

Leu Leu His His His His Gly Ser His Cys Ser Ser Ser Gly Asp Pro
                        565                 570                 575

Ala Glu Tyr Asn Leu Arg Ser Arg Thr Val Leu Cys Gly Thr Cys Gly
                        580                 585                 590

Gln Pro Ala Asp Lys Ala Ser Ala Ser Gly Ser Gly Ala Gln Val Gly
                        595                 600                 605

Gly Pro Ile Ser Ser Gly Ser Ser Ala Ser Ser Val Thr Val Thr Arg
                        610                 615                 620

Ser Tyr Arg Ser Val Gly Gly Ser Gly Gly Ser Phe Gly Asp Asn
        625                 630                 635                 640

Leu Val Thr Arg Ser Tyr Leu Leu Gly Asn Ser Ser Pro Arg Thr Gln
                        645                 650                 655

Ser Pro Gln Asn Cys Ser Ile Met
                        660
```

LAMIN A, AN ACTIVATOR OF LONGEVITY/ANTI-AGING SIRT1 PROTEIN

CROSS-REFERENCE TO RELATED APPLICATION

This application is a divisional of U.S. application Ser. No. 14/078,010, filed Nov. 12, 2013, which claims priority to U.S. Provisional Application No. 61/725,252, filed Nov. 12, 2012, the disclosures of which are hereby incorporated by reference in their entirety.

BACKGROUND OF THE INVENTION

Sirtuins (silent mating type information regulation 2 homolog), class III HDACs containing $NAD^+$-dependent protein deacetylase and ADP-ribosyltransferase activities, regulate various metabolic pathways (Denu, 2005; Donmez and Guarente, 2010; Finkel et al., 2009; Haigis and Sinclair, 2010).

Of seven mammalian sirtuins, SIRT1 (NAD-dependent deacetylase sirtuin-1) is the closest homolog of *Saccharomyces cerevesiae* Sir2 (silent information regulator 2) identified three decades ago (Klar et al., 1979). Loss of SIRT1 causes defective gametogenesis, heart and retinal abnormalities, genomic instability, small body size, and reduced survival in mice (Cheng et al., 2003; McBurney et al., 2003; Wang et al., 2008); and abolishes many beneficial effects of dietary restriction (Chen et al., 2005). Although lifespan extension in *Saccharomyces cerevesiae, C. elegans* and *Drosophila* by ectopic Sir2 is still under debate (Burnett et al., 2011; Lombard et al., 2011; Tissenbaum and Guarente, 2001; Viswanathan and Guarente, 2011; Viswanathan et al., 2005), transgenic mice with additional copies of SIRT1 show phenotypes resembling dietary restriction and consistent with improved healthspan (Alcendor et al., 2007; Banks et al., 2008; Bordone et al., 2007; Herranz et al., 2010; Pfluger et al., 2008).

SIRT1 deacetylates a variety of proteins, including KU70, Nbs1, p53, NF-κB, PPARγ, PGC-1α, FOXO, and SUV39H1, and regulates genomic integrity, the inflammatory response, adipogenesis, mitochondrial biogenesis, and stress resistance (Lavu et al., 2008). For example, SIRT1 catalyzes the deacetylation of tumor suppressor protein p53, thus promoting survival by inhibiting p53-mediated apoptosis (Cheng et al., 2003). SIRT1 also directly interacts with PPAR-γ and PGC-1α, thus regulating metabolic response (Picard et al., 2004; Rodgers et al., 2005).

In addition, SIRT1 deacetylates Foxo3a to enhance stress resistance through Foxo3a targets such as MnSOD, catalase, and Gadd45α (Brunet et al., 2004). SIRT1 is highly expressed in embryonic stem cells (ESCs), but its expression is reduced in differentiated cells through a process mediated by miRNAs (Saunders et al., 2010). SIRT1 is required for maintenance of self-renewal of ESCs via modulating p53 cellular distribution and Nanog expression (Han et al., 2008). The hematopoietic differentiation of ESCs is defective and the number and function of hematopoietic progenitor cells decline in $SIRT1^{-/-}$ and $SIRT1^{+/-}$ mice (Lee et al., 2011). When cultured under 5% oxygen, both $SIRT1^{-/-}$ and $SIRT1^{+/-}$ hematopoietic progenitor cells exhibit defective proliferation compared with wild-type cells (Mantel et al., 2008).

SIRT1 is one of the most conserved anti-aging/longevity-promoting proteins across species. Increase in SIRT1 deacetylase activity confers many beneficial effects on various mouse models mimicking human metabolic or degenerative diseases, such as obesity, diabetes, and Alzheimer's Diseases. Therefore, SIRT1-activating compounds could benefit human patients suffering from various metabolic and aging-related degenerative diseases. On the other hand, SIRT1 protein is found upregulated in various human cancers, and inhibition of SIRT1 activity could help in eliminating cancer stem cells (Li et al., 2012).

Increased SIRT1 activity has been documented as beneficial in many disease models and human patients; therefore, it has been widely accepted that SIRT1-activating compounds could provide therapeutic benefits for various metabolic and degenerative diseases (Baur, 2010). On the other hand, the suppressing role for SIRT1 in p53 apoptotic activity suggests tumor-promoting properties of SIRT1 (Luo et al., 2001). Indeed SIRT1 protein has been reported to be elevated in many types of neoplasia, including prostate cancer, acute myeloid leukemia, colon cancer, and various non-melanoma skin cancers (Deng, 2009). It has been recently reported that inhibiting SIRT1 activates p53, thus facilitating the elimination of leukemia stem cells (Li et al., 2012). Therefore, SIRT1-inhibiting compounds confer therapeutic potentials for various human malignancies. Resveratrol, a compound identified in a screen for SIRT1 activators, has been reported to increase lifespan in yeast, worms, and flies, and to enhance healthspan in rodents (Agarwal and Baur, 2011; Baur et al., 2006; Howitz et al., 2003; Milne et al., 2007; Wood et al., 2004). Beneficial effects of resveratrol have been reported on aging-related cataracts, reduced bone density, neurodegenerative diseases, obesity, and diabetes. Resveratrol induces multiple gene expression alterations, mimicking multiple gene expression alterations induced by calorie restriction (CR) (Pearson et al., 2008).

Consumption of RESVIDA®, a resveratrol-containing composition, confers significant metabolic changes similar to that of CR in obese human individuals (Timmers et al., 2011). Studies involving another resveratrol-containing nutraceutical, LONGEVINEX®, revealed that short-term consumption of the nutraceutical can recapitulate the long-term effects of CR (Barger et al., 2008).

A-type nuclear lamins, encoded by the LMNA locus, are type V intermediate filament proteins. The two most prominent A-type lamins, lamin A and C, only differ in the C-terminus where CaaX motif dictates a series of processing events including transient isoprenylation (Rusinol and Sinensky, 2006). A de novo G608G mutation in LMNA promotes alternate splicing, yielding a partially processed prelamin A (also referred to as progerin) that is the predominant cause of Hutchinson-Gilford Progeria Syndrome, a severe form of early-onset premature aging (Eriksson et al., 2003). Mice deficient for Zmpste24, a metalloproteinase responsible for prelamin A maturation, manifest many of the progeroid features resembling Hutchinson-Gilford progeria syndrome (HGPS) patients (Pendas et al., 2002).

The present inventors and other researchers have shown that HGPS skin fibroblasts and mouse embryonic fibroblasts (MEFs) derived from $Zmpste24^{-/-}$ embryos undergo early senescence attributable to genomic instability and hyperactivation of the p53 pathway, and that reduction of the prelamin A level in $Zmpste24^{-/-}$ mice by Lmna heterozygosity ameliorates progeroid phenotypes and significantly extends lifespan (Fong et al., 2004; Liu et al., 2005; Varela et al., 2005). Human cells engineered to express progerin exhibited defective proliferation and premature senescence (Candelario et al., 2008; Kudlow et al., 2008).

Lamin A/C is a major component of the nuclear matrix (NM), a filamentous nucleoskeleton distinct from chromatin and important for maintaining nuclear structure (Fey et al., 1991). Chromatin and other proteins dynamically associate with the NM to regulate various nuclear activities, including replication, gene transcription, DNA repair, and chromatin organization (Blencowe et al., 1994; Kruhlak et al., 2000; Phair and Misteli, 2000). For example, the NM co-purifies with a majority of the nuclear histone deacetylase (HDAC) activity (Downes et al., 2000; Hendzel et al., 1991; Li et al., 1996). One of the hallmarks of HGPS and Zmpste24$^{-/-}$ cells is a misshaped nucleus, which leads to disorganized heterochromatin (Liu et al., 2005; Pendas et al., 2002; Scaffidi and Misteli, 2005) and mislocalized nuclear proteins, such as ATR, SKIP, XPA and Mof (Krishnan et al., 2011; Liu et al., 2005; Liu et al., 2008; Manju et al., 2006; Pendas et al., 2002; Scaffidi and Misteli, 2005, 2006, 2008). Rescue of nuclear shape abnormality by reducing unprocessed prelamin A or progerin from the nuclear envelope via treatment with farnesyl transferase inhibitor (FTI) significantly ameliorates progeroid features in both HGPS cells and mouse models (Capell et al., 2005; Fong et al., 2006; Glynn and Glover, 2005; Toth et al., 2005; Varela et al., 2008).

Alternate splicing events at the wild type LMNA locus can lead to expression of low levels of progerin, which may affect the normal aging process (Scaffidi and Misteli, 2006). An increased number of cells expressing progerin were found during aging in normal individuals (McClintock et al., 2007) and telomere shortening or dysfunction activates progerin production (Cao et al., 2011). These findings suggest that progerin may contribute to the normal aging process (Burtner and Kennedy, 2010), possibly through modulating the activity of proteins implicated in aging.

Over the past several years, calorie restriction (CR)-mimicking properties of resveratrol and SIRT1 protein have attracted considerable efforts in searching for resveratrol mimics and SIRT1 activators. Compounds exhibiting significantly higher SIRT1-activating potential than resveratrol have been identified, and these compounds can elicit similar CR-mimicking beneficial effects as that of resveratrol. In addition, it has been reported that resveratrol specifically enhances SIRT1 activity towards a fluorophore-conjugated synthetic peptide (Ac-Arg-His-Lys-Lys$^{Ac}$-AMC) (SEQ ID NO:1) rather than the unmodified one (Borra et al., 2005; Kaeberlein et al., 2005). This observation was later confirmed by other researchers, showing that resveratrol and SRT1720 do not confer any SIRT1 activation towards its full-length native target proteins, including p53 and PGC-1α (Beher et al., 2009; Dai et al., 2010; Pacholec et al., 2010). Therefore, despite various beneficial effects of resveratrol and mimics, the underlying mechanism is still unclear.

BRIEF SUMMARY OF THE INVENTION

In one embodiment, the present invention provides methods of modulating the deacetylase activity of SIRT1 in one or more cell by modifying the binding affinity of lamin A to SIRT1 via an interaction modifying compound. The deacetylase activity of SIRT1 can be increased by an increased binding affinity of lamin A to SIRT1 and decreased by a decreased binding affinity of lamin A to SIRT1. An example of an interaction modifying compound includes, but is not limited to, resveratrol. Resveratrol increases the binding affinity of lamin A to SIRT1 in embodiments described herein. In some embodiments of the present invention, SIRT1 deacetylase activity is modulated via an interaction modifying compound by enhancing the binding capacity of the carboxyl terminus of lamin A protein to SIRT1 protein.

In one embodiment, the present invention provides methods of screening for agents that modulate SIRT1 deacetylase activity based on the interaction between lamin A and SIRT1 proteins and SIRT1-activating/inhibiting properties of lamin A. Some methods include contacting a candidate molecule with cells expressing SIRT1 in a test sample; determining deacetylase activity in the test sample; and selecting the candidate molecule as an agent that modulates SIRT1 deacetylase activity if the molecule changes the level of SIRT1 deacetylase activity in the test sample. Candidate molecules that activate or enhance SIRT1 deacetylase activity include, but are not limited to, peptide fragments of lamin A, including peptide fragments of the carboxyl domain of lamin A; analogs of lamin A, including peptide fragments of such analogs; compounds that enhance the binding of lamin A to SIRT1; compounds that enhance or induce the expression of lamin A; and combinations thereof. Candidate molecules that inhibit or reduce SIRT1 deacetylase activity include, but are not limited to, peptide fragments of lamin A, including the carboxyl domain of the lamin A peptide; analogs of lamin A, including peptide fragments of such analogs; agents or compounds that inhibit lamin A activity; agents or compounds that inhibit expression of lamin A; and combinations thereof.

In one embodiment, the present invention provides a method for treating a disease or condition in which modulated SIRT1 deacetylase activity is beneficial. Methods include administering to a subject in need of such treatment, an effective amount of an agent that modulates SIRT1 deacetylase activity. In some embodiments, the agent administered increases SIRT1 deacetylase activity. Examples of SIRT1-activating compounds include, but are not limited to, peptide fragments of lamin A, including fragments of the carboxyl domain of lamin A; analogs of the lamin A, or fragments thereof; compounds that enhance the binding of lamin A to SIRT1; and combinations thereof. In other embodiments, the agent administered decreases SIRT1 deacetylase activity. Such agents include, but are not limited to, carboxyl terminal peptides of lamin A, and analogs of carboxyl terminal peptides of lamin A.

Embodiments of methods of the present invention that result in increased SIRT1 deacetylase activity are useful in treating diseases or conditions where it is beneficial to increase the number and/or function of bone marrow stromal cells and/or hematopoietic stem cells, such as, but not limited to, metabolic and/or aging-related degenerative diseases. As a result, for example, an increase in bone density and prevention of bone loss can occur. Furthermore, embodiments of methods of the present invention that result in decreased SIRT1 deacetylase activity are useful in treating neoplasia and other malignancies.

In one embodiment, the present invention provides methods for increasing SIRT1 deacetylase activity in one or more cell. Methods include administering to, or contacting, one or more cell that expresses SIRT1, and is in need of increased SIRT1 deacetylase activity, a lamin A peptide, an analog of the lamin A peptide, or functional fragment thereof, in an amount effective to increase the deacetylase activity of SIRT1. In one embodiment, the lamin A peptide useful according to the present invention is of human origin, having the amino acid sequence of (SEQ ID NO:2; GENBANK™ Accession No. NP_733821), or an analog thereof. In one embodiment, the functional fragment of the lamin A peptide that increases SIRT1 deacetylase activity comprises the carboxyl domain of lamin A, or an analog thereof. The carboxyl domain of the lamin A peptide may include the amino acids 567-646 of SEQ ID NO:2, or one or more fragment thereof. Particularly useful fragments are from about 3 amino acids to about 50 amino acids in length.

In one embodiment, the present invention provides methods for decreasing or inhibiting SIRT1 deacetylase activity in AMC one or more cell. Methods include administering to one or more cell that expresses SIRT1, and is in need of decreased SIRT1 deacetylase activity, an inhibitor of the lamin A protein or peptide. Lamin A inhibitors useful according to embodiments of the present invention include, but are not limited to, agents that inhibit lamin A activity; and agents that reduce or inhibit the expression of lamin A, such as agents that inhibit the transcription, translation, and/or processing of lamin A.

BRIEF DESCRIPTION OF THE DRAWINGS

FIGS. 1A-1G show that SIRT1 interacts with lamin A, and that the formation of prelamin A/progerin jeopardizes the SIRT1-lamin A interaction. (FIG. 1A) FLAG-SIRT1 and lamin A were ectopically expressed in HEK293 cells. By Western blotting, lamin A was detected in anti-FLAG immunoprecipitates; FLAG-SIRT1 was detected in anti-lamin A/C immunoprecipitates. (FIG. 1B) In total cell lysate of HEK293 cells, endogenous SIRT1 was pulled down by anti-lamin A/C immunoprecipitates and reciprocally; endogenous lamin A was pulled down by anti-SIRT1 immunoprecipitates. (FIG. 1C) Immunofluorescence staining and confocal microscopy of SIRT1 and lamin A/C in human fibroblasts. Majority of nuclear SIRT1 co-localizes with lamin A in the nuclear interior (arrows). Scale bar, 5 μm. (FIG. 1D) Confocal microscopy showed co-localization of ectopic EGFP-SIRT1 and DsRed-lamin A in human fibroblast cells. Scale bar, 10 μm. (FIG. 1E) Recombinant human SIRT1 (rhSIRT1) was pulled down by anti-lamin A immunoprecipitates in test tubes containing rhSIRT1 and recombinant human lamin A (rhLamin A). (FIG. 1F) Lamin A, but not lamin C, was pulled down in anti-FLAG-SIRT1 immunoprecipitates in HEK293 cells. (FIG. 1G) HEK293 cells were transiently transfected with FLAG-SIRT1 together with one of the A-type lamins, i.e., wild-type lamin A, unprocessable prelamin A, and progerin. Western blotting was performed to determine levels of A-type lamins in anti-FLAG immunoprecipitates. Note that significantly less prelamin A/progerin was pulled down by anti-FLAG antibody compared with wild-type lamin A.

(FIG. 2A) Representative immunoblot showing various proteins in nuclear (Nu, P1) and nuclear matrix (NM, P2') fractions. NM-associated SIRT1 was significantly reduced in Zmpste24$^{-/-}$ BMSCs, whereas levels of Sirt6, CBP, Foxo3a, histone H3 and β-actin were comparable between wild-type and Zmpste24$^{-/-}$ BMSCs in NM fraction. Total nuclear level of SIRT1 was not changed. (FIG. 2B) Quantification of (FIG. 2A). Data represent mean±SEM, n=3. P<0.01. (FIG. 2C) Lamin A, unprocessible prelamin A or progerin was stably expressed in HEK293 cells. Subcellular fractionation and Western blotting were performed to determine the NM associated SIRT1. While NM-association of SIRT1 was reduced in prelamin A- and progerin-transfected cells compared with wild-type lamin A, the levels of Foxo3a and β-Catenin remained unchanged. (FIG. 2D) Quantification of (FIG. 2C). Data represent mean±SEM, n=3. P<0.01. (FIG. 2E) Hyperacetylation of Foxo3a in Zmpste24$^{-/-}$ BMSCs determined by Western blotting with anti-acetyl lysine antibodies in anti-Foxo3a immunoprecipitates. (FIG. 2F) Quantification of (FIG. 2E). Data represent mean±SEM, n=3. *P<0.05, **P<0.01. (FIG. 2G) Upper, acetylation of Foxo3a in HEK293 cells expressing ectopic lamin A or prelamin A or progerin determined by Western blotting with anti-acetyl lysine antibodies in anti Foxo3a immunoprecipitates; lower, expression of catalase, MnSOD and GADD45α in the input.

FIGS. 3A-3H show that resveratrol directly activates SIRT1 in a lamin A-dependent manner. (FIG. 3A) RhSIRT1 deacetylase activity was determined by BIOMOL®-SIRT1 Fluorimetric Drug Discovery Kit (BSDK) in the presence or absence of rhLamin A. Data represent mean±SEM, n=3. *P<0.05, P<0.01, rhLamin A+rhSIRT1 Vs rhSIRT1 only. *The molar ratio of rhLamin A to rhSIRT1 is 0.5, 1.0, 2.0, and 4.0 respectively. (FIG. 3B) Acetyl FLAG-p53 was incubated with rhSIRT1 and rhLamin A in the presence or absence of resveratrol. FLAG-p53 acetylation was detected by Western blotting with anti-acetyl lysine antibodies. Relative level of acetylated p53 was quantified by IMAGE J®. *The molar ratio of rhLamin A to rhSIRT1 is 0.5, 1.0 and 2.0 respectively. (FIG. 3C) Level of rhSIRT1 pulled down by anti-lamin A/C antibody in the presence or absence of resveratrol was assessed by Western blotting. (FIG. 3D) FLAG-SIRT1 and lamin A were co-transfected into HEK293 cells. Cells were treated with resveratrol followed by anti-FLAG immunoprecipitation. Western blotting showed that resveratrol treatment increased the interaction between SIRT1 and lamin A in a dose-dependent manner. (FIG. 3E) Quantification of (FIG. 3D). Data represent mean±SEM, n=3. *P<0.05. (FIG. 3F) Representative immunoblot in wild-type, SIRT1 null and Lmna null cells treated with different doses of resveratrol. (FIG. 3G) Immunofluorescence staining of H3K9ac in wild-type and Lmna null cells treated or untreated with resveratrol. (FIG. 3H) Resveratrol enhanced the association of rhSIRT1 with NM in test tube. Recombinant hSIRT1 was incubated with NM fraction prepared from wild-type or Zmpste24$^{-/-}$ BMSCs in the presence and absence of resveratrol (10 μM) in a similar way as the SIRT1 deacetylase activity assay was performed. Insoluble NM and reaction buffer were separated by centrifugation. Western blotting and Coomassie Blue staining were performed to determine the level of rhSIRT1.

FIGS. 4A-4I show that resveratrol rescues the decline of bone marrow stromal cells (BMSCs) in Zmpste24$^{-/-}$ mice in SIRT1-dependent manner. (FIG. 4A) Resveratrol (10 μM) increased colony-forming capacity of Zmpste24$^{-/-}$ BMSCs. Colony-forming assay was performed on freshly isolated bone marrow cells in 10 cm dishes in the presence and absence of resveratrol. (FIG. 4B) Colony number counting. Data showed that resveratrol (RSV) increased colony-formation capacity of Zmpste24$^{-/-}$ BMSCs in a dose-dependent manner (2 μM and 10 μM). Data represent mean±SEM, n=4. *P<0.05, RSV Vs Vehicle. (FIG. 4C) Left, level of prelamin A pull down by anti SIRT1 immunoprecipitates in BMSCs treated or untreated with resveratrol (2 μM) was determined by Immunoblotting; right, level of acetylated Foxo3a in resveratrol was assessed by Immunoblotting. (FIG. 4D) Levels of catalase and Gadd45α in SIRT1 or scramble siRNA treated Zmpste24$^{-/-}$ BMSCs in the presence or absence of resveratrol (10 μM) determined by Western blotting. (FIG. 4E) Colony-forming capacity of Zmpste24$^{-/-}$ BMSCs by SIRT1 or scramble knocking down in the presence or absence of resveratrol. Resveratrol treatment (10 μM) increased the colony-forming capacity in Zmpste24$^{-/-}$ BMSCs (left) and this was completely abolished by knocking down SIRT1 (right). Colony forming assay was done on freshly isolated cells in 6-well plates. (FIG. 4F) Quantification of (FIG. 4E). Data represent mean±SEM, n=5. *P<0.05, "Scramble+RSV" Vs "Scramble+Veh". (FIG. 4gG Levels of H3K9ac and IR-induced-H2AX with or without ectopic SIRT1 in wild-type and Zmpste24 null BMSCs were assessed by Western blotting. (FIG. 4H) Ectopic SIRT1 increased the colony-forming capacity of Zmpste24$^{-/-}$ and wild-type BMSCs. Colony-forming assay was performed on freshly isolated cells in 6 cm dishes. (FIG. 4I) Quantification of (FIG. 4H). Data represent mean±SEM, n=5. *P<0.05, SIRT1 Vs Mock.

FIGS. 5A-5J show that resveratrol rescues ASC decline, ameliorates progeroid features, and extends lifespan in Zmpste24$^{-/-}$ mice. (FIG. 5A) Colony-forming capacity of BMSCs in Zmpste24$^{-/-}$ mice treated with either vehicle or resveratrol (20 μg/ml in drinking water). Colony-forming assays were performed on freshly isolated bone marrow cells in 10 cm dishes. (FIG. 5B) Quantification of (FIG. 5A). Data represent average colony number of BMSCs±SEM, n=3. *P<0.05. (FIG. 5C) Levels of catalase, acetylated p53 and H3K9ac in BMSCs isolated from vehicle-treated and resveratrol-treated Zmpste24$^{-/-}$ mice. (FIG. 5D) Feeding Zmpste24$^{-/-}$ mice with resveratrol increased HSC population. Each dot represents the percentage of HSC population in total bone marrow mononucleated cells in individual mouse. *P<0.05, vehicle-treated Zmpste24$^{-/-}$ mice Vs wild-type and resveratrol-treated (20 μg/ml in drinking water) Vs vehicle-treated Zmpste24$^{-/-}$ mice. (FIG. 5E) Micro-CT examination of trabecular bone structure in wild-type mice and in Zmpste24$^{-/-}$ mice treated with either resveratrol (20 μg/ml in drinking water) or vehicle. (FIG. 5F) Resveratrol-treatment increased bone mineral density in Zmpste24$^{-/-}$ mice. Data represent mean±SEM, n=3. *P<0.05, vehicle-treated Zmpste24$^{-/-}$ mice Vs wild-type and resveratrol-treated (20 μg/ml in drinking water) Vs vehicle-treated Zmpste24$^{-/-}$ mice. (FIG. 5G) Body weight in resveratrol-treated and vehicle-treated male Zmpste24$^{-/-}$ mice. Data represent mean±SEM, n=10. *P<0.05. (FIG. 5H) Body weight in resveratrol-treated and vehicle-treated female Zmpste24$^{-/-}$ mice. Data represent mean±SEM, n=10. *P<0.05. (FIG. 5I) Survival rate in resveratrol-treated and vehicle-treated Zmpste24$^{-/-}$ mice. P<0.0001. (FIG. 5J) Maximal lifespan in resveratrol-treated and vehicle-treated Zmpste24$^{-/-}$ mice. Data represent mean±SEM. **P<0.01.

FIGS. 6A-6C show that lamin A interacts with SIRT1. (FIG. 6A) Endogenous interaction between lamin A and SIRT1 in BMSCs was determined by co-immunoprecipitation. (B) Endogenous interaction between lamin A and SIRT1 in wilt-type and Lmna null mouse embryonic fibroblasts (MEFs) was determined by co-immunoprecipitation. (FIG. 6C) Interaction between GFP-lamin A and SIRT1, SIRT2 and SIRT5 was assessed by anti GFP co-immunoprecipitation.

FIGS. 7A-7I show mislocalization and reduced deacetylase activity of SIRT1 in progeria cells and activation of SIRT1 by resveratrol in the presence of lamin A. (FIG. 7A) Expression of Kap-1 and Mcm3 in different subcellular fractions. Cells were fractionated and the subcellular distribution of Kap-1 and Mcm3 was determined by Western blotting. (FIG. 7B SIRT1$^{-/-}$ and wild-type MEFs were fractionated into cytoplasmic (Cyto, S1), nucleoplasmic/chromatic (Np+Chr, S2'), and nuclear matrix (NM, P2') fractions. Representative immunoblot showing the NM association of SIRT1. (FIG. 7C) SIRT1 expression in nuclear and NM fractions determined by Western blotting in dermal fibroblasts derived from healthy individual and patients with different LMNA gene mutations. Note that the NM-associated SIRT1 was significantly down-regulated in HGPS cells compared to that in cells from healthy individual or from patients with non-progeria LMNA mutations. The total nuclear level of SIRT1 was also decreased in HGPS cells. (FIG. 7D) Quantification of SIRT1 in human cells. Significant down-regulation of NM-associated SIRT1 relative to total nuclear SIRT1 in HGPS fibroblasts, compared with that in dermal fibroblasts from non-progeria laminopathy patients and healthy individual. (FIG. 7E) RhSIRT1 deacetylase activity was determined in the presence of cytoplasmic or NM fraction. The relative increase in deacetylase activity after addition of rhSIRT1 to the assay buffer, cytoplasmic or NM was determined and plotted. The NM from wild-type BMSCs potentiated rhSIRT1 deacetylase activity whereas the stimulating capacity of NM from Zmpste24$^{-/-}$ BMSCs was greatly compromised. Data represent mean±SEM, n=3. *P<0.05. (FIG. 7F) Acetyl FLAG-p53 was incubated with rhSIRT1 in the presence or absence of rhLamin A and resveratrol. FLAG-p53 acetylation was detected by Western blotting with anti-acetyl lysine antibodies. (FIG. 7G) Resveratrol enhanced NM-association of SIRT1 in wild-type and Zmpste24$^{-/-}$ BMSCs determined by Western blotting. (FIG. 7H) Quantification of (FIG. 7G). Data represent mean±SEM, n=3. *P<0.05. (FIG. 7I) Nuclear matrix (NM) fraction preserves SIRT1 deacetylase activity. Recombinant human SIRT1 (rhSIRT1) deacetylase activity was determined by BIOMOL® SIRT1 Fluorimetric Drug Discovery Kit in the presence or absence of nuclear matrix fraction. Suramin Sodium was applied as an inhibitor of SIRT1. The relative rhSIRT1 deacetylase activity was plotted. Data represent mean±SEM, n=3. *P<0.05.

(FIG. 8A) Cellular senescence determined by senescence-associated β-galactosidase assay in Zmpste24$^{-/-}$ MEFs treated with resveratrol. (FIG. 8B) Levels of p16$^{ink4a}$ in resveratrol-treated MEF cells determined by Western blotting.

FIGS. 9A-9H show accelerated ASC decline in Zmpste24$^{-/-}$ mice. (FIG. 9A) Number of BMSC colonies after 12-days culture. Colony-forming assay was performed in 10 cm dishes with freshly isolated bone marrow cells from 4-month-old wild-type and Zmpste24$^{-/-}$ mice. Data represent mean±SEM, n=5. *P<0.01. (FIG. 9B) Colonies of magnetically enriched BMSCs from either wild-type or mutant mice in 10 cm dishes after 12-days culture. (FIG. 9C) Proliferative capacity of enriched BMSCs from 1-month and 5-months wild-type and Zmpste24$^{-/-}$ mice. Data represent mean±SEM, n=3. P<0.001. (FIG. 9D) Senescence-associated β-galactosidase assay in enriched BMSCs from 1-month-old wild-type and Zmpste24$^{-/-}$ mice. Data represent mean±SEM, n=3. P<0.001. (FIG. 9E) Total number of mononucleated cells in femurs and tibias from 4-month-old wild-type and Zmpste24$^{-/-}$ mice. Data represent mean±SEM, n=6. *P<0.05. (FIG. 9F) Representative FACS profiles of HSCs in bone marrow from 4-month-old Zmpste24$^{-/-}$ and wild-type mice. Gate R4 represents HSC population (Lineage$^-$Flt3$^-$Sca-1$^+$c-Kit$^{high}$). Note reduced HSC population in Zmpste24$^{-/-}$ mice. (FIG. 9G) Percentage of HSC population in total mononucleated cells in bone marrow of 1-month-old, 2-month-old and 4-month-old wild-type and Zmpste24$^{-/-}$ mice. *P<0.01. (FIG. 9H) HSCs from 1-month-old wild-type or Zmpste24$^{-/-}$ mice were transplanted into lethally irradiated recipients. In wild-type transplanted recipients, B cell differentiation was not affected at 1, 4 or 6 months; in recipients repopulated with Zmpste24$^{-/-}$ donors, the B cell lineage was greatly reduced 4 months after transplantation. **P<0.001, Zmpste24$^{-/-}$ vs Zmpste24$^{+/+}$.

FIGS. 10A-10F show that N-acetyl cysteine feeding rescues ASC decline and extends lifespan in Zmpste24$^{-/-}$ mice. (FIG. 10A) Colony forming unit-fibroblast (CFU-F) of enriched BMSCs determined in the presence or absence of $H_2O_2$. Data represent mean±SEM, n=3. *P<0.05. (FIG. 10B) Elevated ROS level in freshly isolated Zmpste24$^{-/-}$ HSCs compared with that in wild-type HSCs (left) and rescued ROS level by N-acetyl Cysteine (NAC, 1 mg/ml in drinking water) (right). (FIG. 10C) Colony-forming efficiency of BMSCs in Zmpste24$^{-/-}$ mice treated with either vehicle or NAC (1 mg/ml in drinking water). Colony-forming assays were performed on freshly isolated bone marrow cells in 10 cm dishes. Data represent mean±SEM, n=3. *P<0.05. (FIG. 10D) Percentage of bone marrow HSC population in vehicle-treated and NAC-treated Zmpste24$^{-/-}$ mice. *P<0.05, vehicle-treated Zmpste24$^{-/-}$ mice Vs wild-type and NAC-treated Vs vehicle-treated Zmpste24$^{-/-}$ mice. (FIG. 10E) Body weight of vehicle-treated and NAC-treated Zmpste24$^{-/-}$ mice at 4-months of age. Data represent mean±SEM, n=12. *P<0.05, NAC-treated Vs vehicle-treated. (FIG. 10F) Survival rate of vehicle-treated and NAC-treated Zmpste24$^{-/-}$ mice. P<0.0001.

(FIG. 11B) RhSIRT1 deacetylase activity was determined by BIOMOL® SIRT1 Fluorimetric Drug Discovery Kit (BSDK) in the presence or absence of rhLamin A. Data represent mean±SEM, n=3. *P<0.05, P<0.01, rhLamin A+rhSIRT1 Vs rhSIRT1 only. *The molar ratio of rhLamin A to rhSIRT1 is 0.5, 1.0, 2.0, and 4.0 respectively. (FIG. 11C) Acetyl FLAG-p53 was incubated with rhSIRT1 in the presence or absence of rhLamin A. FLAG-p53 acetylation was detected by Western blotting with anti-acetyl lysine antibodies. Relative level of acetylated p53 was quantified by IMAGE J®. *The molar ratio of rhLamin A to rhSIRT1 is 0.5 and 1.0 respectively. (FIG. 11D) RhSIRT1 deacetylase activity was determined by BIOMOL® SIRT1 Fluorimetric Drug Discovery Kit (BSDK) in the presence or absence of LA-80 (synthetic peptide of carboxyl 80 aa of lamin A). Data represent mean±SEM, n=3. **P<0.01, LA-80+rhSIRT1 Vs rhSIRT1 only. (FIG. 11E) Acetyl FLAG-p53 was incubated with rhSIRT1 in the presence of various amount of LA-80. FLAG-p53 acetylation was detected by Western blotting with anti-acetyl lysine antibodies (left). Relative level of acetylated p53 was quantified by IMAGE J® (right).

BRIEF DESCRIPTION OF THE SEQUENCES

Figure 1A:
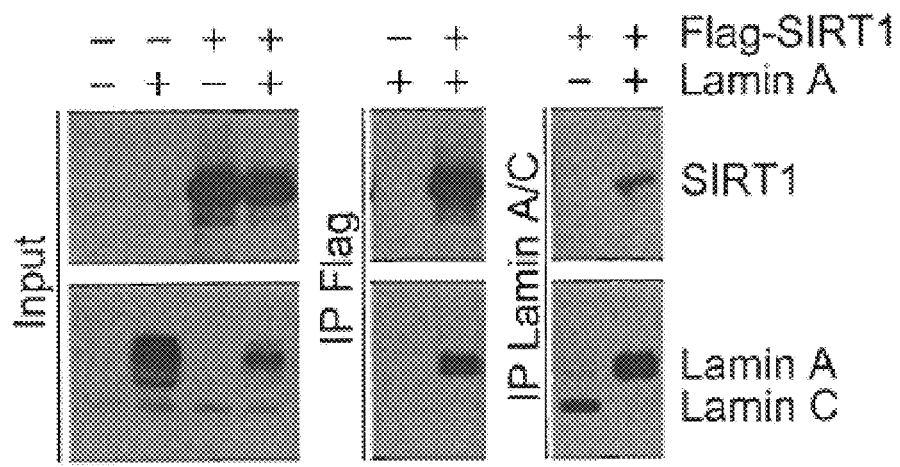

SEQ ID NO:1 is the amino acid sequence useful according to the present invention.

SEQ ID NO:2 is the amino acid sequence of the human lamin A protein.

DETAILED DISCLOSURE OF THE INVENTION

In one embodiment, the present invention provides methods of screening SIRT1-activating/inhibiting compounds based on the interaction between lamin A and SIRT1 proteins and SIRT1-activating property of lamin A. In another embodiment, the present invention provides uses of SIRT1-activating compounds to treat patient(s)/subject(s) suffering from metabolic and/or aging-related degenerative diseases, and uses of SIRT1-inhibiting compounds to treat human malignancies. In another embodiment, the present invention provides methods of modulating the deacetylase activity of SIRT1 by modifying the binding affinity of lamin A to SIRT1 via interaction modifying compound(s).

Activation of SIRT1 Deacetylase Activity by Lamin A

Given the essential roles of the nuclear matrix (NM) in preserving HDAC activity and the longevity-promoting properties of resveratrol, the potential effect of lamin A on SIRT1 is determined. The results show that lamin A directly interacts with SIRT1 and serves as an activator of SIRT1 on the NM; prelamin A and progerin exhibit significantly reduced binding capacity to SIRT1, therefore mis-localize SIRT1 from the NM, leading to rapid decline of ASCs in Zmpste24$^{-/-}$ mice. Resveratrol increases the binding of SIRT1 with A-type lamins both in vitro and in vivo, and thus can enhance the deacetylase activity of SIRT1, restore ASC population, ameliorate progeroid features, and extend lifespan in Zmpste24$^{-/-}$ mice.

The present invention shows that lamin A is an activator of SIRT1; Resveratrol activates SIRT1 via increasing its interaction with lamin A; Resveratrol rescues ASC decline in the SIRT1-dependent manner; and Resveratrol-treatment alleviates progeroid features and extends lifespan in progeria mice.

The present invention shows that nuclear lamin A protein forms complex with longevity/anti-aging SIRT1 protein in vivo. Lamin A protein directly binds to SIRT1 protein. Lamin A activates SIRT1 deacetylase activity towards both a fluorophore-conjugated synthetic peptide (Ac-Arg-His-Lys-Lys$^{4c}$-AMC) and a full-length acetylated FLAG-p53 protein (a known target of SIRT1 protein). Synthesized peptide, containing 80 amino acids on the carboxyl terminus of lamin A protein, confers much higher activating potential on SIRT1 towards both a fluorophore-conjugated synthetic peptide (Ac-Arg-His-Lys-Lys$^{4c}$-AMC) and a full-length acetylated FLAG-p53 protein.

In one embodiment, the present invention provides methods of screening small peptides of lamin A protein that activate SIRT1 deacetylase activity. In another embodiment, the present invention provides methods for identifying lamin A-peptide-mimicking compounds to activate or inhibit SIRT1 protein. In one embodiment, the present invention provides methods for identifying compounds that modulate the interaction between lamin A protein and SIRT1 protein thus to activate or inhibit the deacetylase activity of SIRT1. In a further embodiment, the present invention provides methods for treatment of patients suffering various metabolic diseases, such as obesity, cardiovascular diseases, diabetes, neurodegenerative diseases, premature aging syndromes and aging. Also provided are methods of using SIRT1-inhibiting compounds for the treatment of human cancers, including prostate cancer, acute myeloid leukemia, colon cancer and various non-melanoma skin cancers.

The present inventors have discovered that the nuclear lamin A protein interacts with the longevity-promoting/anti-aging SIRT1 protein. In one embodiment, the present invention provides methods of screening SIRT1 activators or inhibitors. In another embodiment, the present invention provides methods of increasing or inhibiting SIRT1 activity to treat human metabolic and degenerative diseases as well as neoplasia.

In one embodiment, the invention provides a method of using small carboxyl terminal peptides of lamin A protein to enhance SIRT1 protein activity. Synthesized peptides ranging from 3 mer to 20 mer located in the $G_{567}$-$Y_{646}$ region of mature lamin A protein are determined for their ability to enhance SIRT1 deacetylase activity towards both a fluorophore-conjugated synthetic peptide (Ac-Arg-His-Lys-Lys$^{4c}$-AMC) and a full-length acetylated FLAG-p53 protein (a known target of SIRT1 protein) in vitro. In a further embodiment, the effects of synthesized 3 mers to 20 mers peptides of SIRT1 are tested in cells using the acetylation status of SIRT1 direct deacetylating targets, such as p53 and PGC-1α, as readout. In a still further embodiment, covalently modified aforementioned 3 mer to 20 mer lamin A peptides are tested in the ability to enhance SIRT1 deacetylase activity by aforementioned in vitro and in vivo assays.

In one embodiment, the present invention provides a method of screening compounds that mimic the structure of aforementioned 3 mer to 20 mer lamin A peptides, wherein enhanced deacetylase activity of SIRT1 is determined by a fluorophore-conjugated synthetic peptide (Ac-Arg-His-Lys-Lys$^{4c}$-AMC) and a full-length acetylated FLAG-p53 protein in the test tube. In a further embodiment, the effects of lamin A-peptide-mimics on SIRT1 are tested in cells using the acetylation status of SIRT1 direct deacetylating targets, such as p53 and PGC-1α, as readout.

In one embodiment, the present invention provides a method of identifying compounds capable of enhancing SIRT1 deacetylase activity via increasing the interaction between lamin A and SIRT1 proteins. SIRT1 deacetylase towards both a fluorophore-conjugated synthetic peptide (Ac-Arg-His-Lys-Lys$^{4c}$-AMC) and a full-length acetylated FLAG-p53 protein is determined in the presence of lamin A protein and tested compound. The ability of tested compounds to enhance the interaction between lamin A and SIRT1 in the test tube containing recombinant lamin A and recombinant SIRT1 and in cells can be determined by co-immunoprecipitation, Western blotting, and GST-pull down assays. The ability of tested compounds to activate SIRT1 can be tested in cells by examining the level of acetylated p53 and acetylated PGC-1α.

In one embodiment, this invention provides a method of using aforementioned SIRT1-activating formula, including small lamin A peptides, peptide-mimics and lamin A-SIRT1 interaction enhancing compounds, to treat human metabolic and aging-related degenerative diseases. In one embodiment, the candidate compounds/peptides can be tested in animal (such as mouse) models recapitulating metabolic and aging-related degenerative diseases, such as mice fed with high-fat diet, mouse models resembling Hutchinson-Gilford progeria syndrome (HGPS), db/db diabetic mice, etc.

In another embodiment, this invention provides a method of using SIRT1-inhibiting compounds, including small lamin A peptides, peptide-mimics, and lamin A-SIRT1 interaction inhibiting compounds, to treat human malignancies. In addition, the present invention provides methods for treating metabolic diseases, including obesity, diabetes, neurodegenerative diseases, cardiovascular diseases, premature aging syndromes, and aging, via the administration of SIRT1-activating compounds.

Lamin A directly interacts with SIRT1, and the last 80 amino acids on the carboxyl domain of lamin A serves as an activator of SIRT1. In one embodiment, the present invention provides a method for increasing SIRT1 deacetylase activity, wherein the method comprises administering to a cell that expresses SIRT1 and is in need of increased SIRT1 deacetylase activity a lamin A peptide, an analog of the lamin A peptide, or functional fragment thereof.

Amino acid sequences of various species of the Lamin A protein are publicly known, and can be readily obtained by a person skilled in the art, such as via the GENBANK™ database. In one embodiment, the lamin A peptide useful according to the present invention is of human origin, having the amino acid sequence of SEQ ID NO:2; GENBANK™ Accession No. NP_733821.

In one embodiment, the functional fragment of the lamin A peptide that increases SIRT1 deacetylase activity comprises the carboxyl domain of the lamin A peptide. In one embodiment, the functional fragment of the lamin A peptide that increases SIRT1 deacetylase activity comprises amino acids 570-664 of SEQ ID NO:2.

Inhibition of SIRT1 Deacetylase Activity

In one embodiment, the present invention provides a method for decreasing or inhibiting SIRT1 deacetylase activity, wherein the method comprises administering to a cell that expresses SIRT1, and is in need of decreased SIRT1 deacetylase activity, an inhibitor of the lamin A protein or peptide.

Lamin A inhibitors useful according to the present invention include, but are not limited to, agents that inhibit lamin A activity; and agents that reduce or inhibit the expression of lamin A, such as agents that inhibit the transcription, translation, and/or processing of lamin A.

Agents that inhibit lamin A activity include, but are not limited to, anti-lamin A antibodies, aptamers, lamin A binding partners, and small molecule inhibitors of lamin A.

In one embodiment, the lamin A inhibitor is an antibody, aptamer, or binding partner that binds to lamin A. In a specific embodiment, the lamin A inhibitor is an antibody, aptamer, or binding partner that binds specifically to lamin A. In a further specific embodiment, the lamin A inhibitor is an antibody, aptamer, or binding partner that binds specifically to human lamin A. In a further specific embodiment, the lamin A inhibitor is an antibody, aptamer, or binding partner that binds specifically to a human lamin A of SEQ ID NO:2.

In certain embodiments, the lamin A inhibitor is an antibody, aptamer, or binding partner that binds specifically to a lamin A protein of non-human animal species including, but not limited to, apes, chimpanzees, orangutans, monkeys, dogs, cats, horses, pigs, sheep, goats, chickens, mice, rats, and guinea pigs. Antibodies that bind specifically to lamin A proteins are commercially available. The skilled artisan can readily make antibodies, aptamers, or binding partners that specifically bind to lamin A proteins that are publically known. In another embodiment, the lamin A inhibitor is a fusion construct comprising the antibody, aptamer, or binding partner that binds specifically to a lamin A protein (such as human lamin A).

"Specific binding" or "specificity" refers to the ability of a protein to detectably bind an epitope presented on a protein or polypeptide molecule of interest, while having relatively little detectable reactivity with other proteins or structures. Specificity can be relatively determined by binding or competitive binding assays, using, e.g., BIACORE™ instruments. Specificity can be exhibited by, e.g., an about 10:1, about 20:1, about 50:1, about 100:1, 10.000:1 or greater ratio of affinity/avidity in binding to the specific target molecule versus nonspecific binding to other irrelevant molecules.

Anti-lamin A antibodies of the present invention can be in any of a variety of forms, including intact immunoglobulin molecules, fragments of immunoglobulin molecules such as Fv, Fab and similar fragments; multimers of immunoglobulin molecules (e.g., diabodies, triabodies, and bi-specific and tri-specific antibodies, as are known in the art; see, e.g., Hudson and Kortt, J. Immunol. Methods 231:177 189, 1999); fusion constructs containing an antibody or antibody fragment; and human or humanized immunoglobulin molecules or fragments thereof.

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Antibodies of the present invention include polyclonal and monoclonal antibodies. The term "monoclonal antibody," as used herein, refers to an antibody or antibody fragment obtained from a substantially homogeneous population of antibodies or antibody fragments (i.e. the individual antibodies within the population are identical except for possible naturally occurring mutations that may be present in a small subset of the antibody molecules).

A monoclonal antibody composition is typically composed of antibodies produced by clones of a single cell called a hybridoma that secretes (produces) only one type of antibody molecule. The hybridoma cell is formed by fusing an antibody-producing cell and a myeloma or other self-perpetuating cell line. Such antibodies were first described by Kohler and Milstein, Nature, 1975, 256:495-497, the disclosure of which is herein incorporated by reference. An exemplary hybridoma technology is described by Niman et al., Proc. Natl. Acad. Sci. U.S.A., 1983, 80:4949-4953. Other methods of producing monoclonal antibodies, a hybridoma cell, or a hybridoma cell culture are also well known. See e.g., Antibodies: A Laboratory Manual, Harlow et al., Cold Spring Harbor Laboratory, 1988; or the method of isolating monoclonal antibodies from an immunological repertoise as described by Sasatry, et al., Proc. Natl. Acad. Sci. USA, 1989, 86:5728-5732; and Huse et al., Science, 1981, 246: 1275-1281. The references cited are hereby incorporated herein by reference.

In some embodiments, lamin A inhibitors useful according to the present invention are agents that reduce or inhibit the expression of lamin A, such as agents that inhibit the transcription, translation, and/or processing of lamin A.

In an embodiment, the lamin A inhibitor is a lamin A antisense polynucleotide. In an embodiment, the lamin A inhibitor is an antisense polynucleotide that targets human lamin A mRNA. In some embodiments, the lamin A antisense polynucleotides target lamin A mRNAs of non-human animals including, but not limited to, apes, chimpanzees, orangutans, monkeys, dogs, cats, horses, pigs, sheep, goats, chickens, mice, rats, and guinea pigs. The skilled artisan would readily appreciate that the antisense polynucleotides can be designed to target any lamin A mRNAs publically known.

In some embodiments, the lamin A inhibitor is a siRNA having a sequence sufficiently complementary to a target lamin A mRNA sequence to direct target-specific RNA interference (RNAi). In some embodiments, the lamin A inhibitor is siRNA having a sequence sufficiently complementary to a target human lamin A mRNA sequence to direct target-specific RNA interference.

Examples of antisense polynucleotides include, but are not limited to, single-stranded DNAs and RNAs that bind to complementary target lamin A mRNA and inhibit translation and/or induce RNaseH-mediated degradation of the target transcript; siRNA oligonucleotides that target or mediate lamin A mRNA degradation; ribozymes that cleave lamin A mRNA transcripts; and nucleic acid aptamers and decoys, which are non-naturally occurring oligonucleotides that bind to and block lamin A protein targets in a manner analogous to small molecule drugs.

The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms. The terms "nucleic acid" or "nucleic acid sequence" encompass an oligonucleotide, nucleotide, polynucleotide, or a fragment of any of these, DNA or RNA of genomic or synthetic origin, which may be single-stranded or double-stranded and may represent a sense or antisense strand, peptide nucleic acid (PNA), or any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

As used herein, the term "RNA" or "RNA molecule" or "ribonucleic acid molecule" refers generally to a polymer of ribonucleotides. The term "DNA" or "DNA molecule" or deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog", also referred to herein as an "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of endogenous target genes, such as lamin A.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA (e.g., lamin A mRNA) by the RNAi machinery or process. "mRNA" or "messenger RNA" or "transcript" is single-stranded RNA that specifies the amino acid sequence of one or more polypeptides. This information is translated during protein synthesis when ribosomes bind to the mRNA.

The present invention also contemplates vectors (e.g., viral vectors) and expression constructs comprising the nucleic acid molecules useful for inhibiting lamin A expression and/or activity. In an embodiment, the vector comprises a siRNA that targets lamin A mRNA. In another embodiment, the vector comprises a nucleic acid molecule encoding an anti-lamin A antibody.

As used herein, the term "expression construct" refers to a combination of nucleic acid sequences that provides for transcription of an operably linked nucleic acid sequence. As used herein, the term "operably linked" refers to a juxtaposition of the components described, wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

Drug Screening Assays

In one embodiment, the present invention pertains to methods for screening for therapeutic agents that increase or decrease SIRT1 deacetylase activity. The therapeutic agent can be a drug, chemical, compound, protein or peptide, or a nucleic acid molecule (e.g. DNA, RNA such as siRNA).

In one embodiment, the present invention provides a method for screening for agents that increase SIRT1 deacetylase activity, including contacting a candidate molecule with cells expressing SIRT1 in a test sample; determining deacetylase activity in the test sample; and selecting the candidate molecule as the agent that increases SIRT1 deacetylase activity if said molecule increases the level of SIRT1 deacetylase activity in the test sample.

In one embodiment of a screening assay for agents that increase SIRT1 deacetylase activity, the candidate molecule is selected from a fragment of lamin A peptide (such as a fragment of lamin A peptide of SEQ ID NO:2); an analog of compound mimicking lamin A activity, such as a peptidomimetic; or a compound enhancing lamin A-SIRT1 interaction.

Functional fragments of lamin A peptide can be of 5-600 amino acids in length, or of any length therebetween, including, but not limited to, 5, 10, 15, 20, 25, 30, 35, 40, 45, 50, 60, 70, 80, 90, 100, 150, 200, 250, 300, 350, 400, 450, 500, 550, and 600 amino acids in length.

In another embodiment, the screening assay for agents that increase SIRT1 deacetylase activity further includes determining binding of the candidate molecule to SIRT1, and selecting the candidate molecule if said molecule binds to SIRT1 or enhances the binding of lamin A (or a functional fragment thereof) to SIRT1.

In one embodiment, the present invention provides a method for screening for agents that decrease or inhibit SIRT1 deacetylase activity, including contacting a candidate molecule with cells expressing SIRT1 in a test sample; determining deacetylase activity in the test sample; and selecting the candidate molecule as the agent that decreases or inhibits SIRT1 deacetylase activity if said molecule decreases or inhibits the level of SIRT1 deacetylase activity in the test sample.

In one embodiment of a screening assay for agents that decrease or inhibit SIRT1 deacetylase activity, the candidate molecule is selected from agents that inhibit lamin A activity; and agents that reduce or inhibit the expression of lamin A, such as agents that inhibit the transcription, translation, and/or processing of lamin A.

In one embodiment, the screening assay for agents that decrease or inhibit SIRT1 deacetylase activity further includes determining binding of the candidate molecule to SIRT1, and selecting the candidate molecule if said molecule inhibits the binding of lamin A to SIRT1.

In certain embodiments, the screening assays examine the in vitro activity of SIRT1 in deacetylating proteins selected from KU70, Nbs1, p53, NF-κB, PPARγ, PGC-1α, FOXO, and SUV39H1. In certain embodiments, the screening assays examine the in vitro activity of SIRT1 in deacetylating proteins selected from Ac-Arg-His-Lys-Lys$^{Ac}$-AMC (SEQ ID NO:1) or a full-length acetylated FLAG-p53 protein.

The deacetylation activity can be determined by methods including, but not limited to, co-immunoprecipitation, Western blotting, ELISA, immunofluorescence, radioimmunoassay, immunocytochemistry, and a combination thereof.

In certain embodiments, the present invention provides methods including determining SIRT1 activating peptide or mimics on the kinetics ($V_{max}$ and $K_m$) of SIRT1 recombinant protein; determining the structure of SIRT1 in the presence or absence of peptide activator; and determining the biological effects of the peptide activator(s) on cultured human cells and premature aging mouse models.

Treatment of Diseases

In one embodiment, the present invention provides a method for treating a disease or condition in which increased SIRT1 deacetylase activity is beneficial, including administering to a patient or subject in need of such treatment an effective amount of lamin A peptide, an analog of lamin A that increases SIRT1 deacetylase activity or a functional fragment thereof.

In various embodiments, diseases or conditions in which increased SIRT1 deacetylase activity would be beneficial and which can be treated in accordance with the present invention include, but are not limited to, metabolic diseases, such as obesity, diabetes; neurodegenerative diseases, such as Alzheimer's Diseases; and aging-related diseases.

In one embodiment, the present invention provides a method for treating a disease or condition in which decreased SIRT1 deacetylase activity is beneficial, including administering to a patient or subject in need of such treatment, an effective amount of inhibitors of the lamin A peptide. In one embodiment, diseases or conditions in which decreased SIRT1 deacetylase activity would be beneficial include, but are not limited to, neoplasia.

The term "subject" or "patient," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; domesticated animals such as dogs, and cats; livestock such as horses, cattle, pigs, sheep, goats, and chickens; and other animals such as mice, rats, guinea pigs, and hamsters.

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, or affecting the progression, severity, and/or scope of a disease or condition.

The term "effective amount," as used herein, refers to an amount that is capable of treating, preventing, or ameliorating a disease or condition or otherwise capable of producing an intended therapeutic effect.

Therapeutic Compositions and Formulations

The present invention also provides for therapeutic or pharmaceutical compositions including a compound of the invention in a form that can be combined with a pharmaceutically acceptable carrier. In this context, the compound may be, for example, isolated or substantially pure.

The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions. Particularly preferred pharmaceutical carriers for treatment of or amelioration of inflammation in the central nervous system are carriers that can penetrate the blood/brain barrier. As used herein carriers do not include the natural plant material as it exists in nature.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents. These compositions can take the form of solutions, suspensions, emulsion, tablets, capsules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

In one embodiment, the present invention provides pharmaceutical compositions adapted for local injection administration to human beings. Typically, compositions for local injection administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with one or more of the ingredients, e.g., compound, carrier, of the pharmaceutical compositions of the invention.

Routes of Administration

The compounds and compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject.

The amount of the therapeutic or pharmaceutical composition of the invention which is effective in the treatment of a particular disease, condition or disorder will depend on the route of administration, and the seriousness of the disease, condition or disorder, and should be decided according to the judgment of the practitioner and each patient's circumstances. In general, the dosage ranges from about 0.001 mg/kg to about 3 g/kg. For instance, suitable unit dosages may be between about 0.01 to about 3 g, about 0.01 to about 1 g, about 0.01 to about 500 mg, about 0.01 to about 400 mg, about 0.01 to about 300 mg, about 0.01 to about 200 mg, about 0.01 to about 100 mg, about 0.01 to about 50 mg, about 0.01 to about 30 mg, about 0.01 to about 20 mg, about 0.01 to about 10 mg, about 0.01 to about 5 mg, about 0.01 to about 3 mg about, 0.01 to about 1 mg, or about 0.01 to about 0.5 mg. Such a unit dose may be administered more than once a day, e.g. two or three times a day.

The amount of active ingredient that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

Materials and Methods

Cell Lines, Constructs and Antibodies

HEK293 cells, MEFs, and human dermal fibroblasts were maintained in DMEM supplemented with 10% FBS. HGADFN143, HGADFN188, HGADFN164, and HGADFN122 skin fibroblasts derived from HGPS patients were provided by Progeria Research Foundation. Human healthy dermal fibroblasts PH and cells harboring LMNA mutations, i.e. R453W, R482W and R401C, were provided by Professor Manfred Wehnert (Institute of Human Genetics, University of Greifswald, Greifswald, Germany). SIRT1 null MEFs were provided by Professor Chu-Xia Deng (NIDDK, National Institutes of Health, USA). F2-S human fibroblasts and preparation of MEFs from mouse embryos were described elsewhere (Liu et al., 2005).

Transfection was performed with LIPO-FECTAMINE2000® (Invitrogen, USA) according to the manufacture's procedures. SIRT1 siRNA oligos were purchased from Invitrogen. USA. Lamin A and unprocessible prelamin A constructs have been described previously (Liu et al., 2005). The progerin construct was generated by bacterial recombineering based on the lamin A construct. Flag-FOXO3A (Addgene plasmid 8360) was obtained from Dr M. E Greenberg (Brunet et al., 2004). Adenoviral SIRT1 construct (Addgene plasmid 8438) (Rodgers et al., 2005) was provided by Dr P Puigserver. EGFP-SIRT1 construct (Sun et al., 2007) was provided by Prof Qiwei Zhai (Shanghai Institutes for Biological Sciences, China). Flag-tagged SIRT1 mutants, Flag-p53, and p300 constructs were gifts from Dr. Zhenkun Lou (Mayo Clinic College of Medicine, USA).

Rabbit anti-SIRT6, anti-SIRT1, anti-CBP, and anti-acetyl lysine antibodies were obtained from Abcam (Cambridge, UK). Rabbit anti-H3K9ac and mouse anti-γ-H2AX antibodies were purchased from Millipore (Bedford, Mass., USA). Anti-SIRT1, anti-lamin A/C, anti-catalase, anti-MnSOD, and anti-Gadd45α antibodies were purchased from Santa Cruz (Santa Cruz, Calif., USA). Rabbit anti-Foxo3a was purchased from BioVision (Mountain View, Calif., USA). Biotin-labeled lineage markers were purchased from BD Biosciences (San Jose, Calif., USA). PE anti-mouse CD105 antibody was purchased from eBioscience (San Diego, Calif., USA).

Resveratrol Treatment of Zmpste24$^{-/-}$ Mice

Zmpste24$^{-/-}$ mice have been described previously (Pendas et al., 2002). Mouse experimentation was performed in accordance with the guidelines of the Committee on the Use of Live Animals in Teaching and Research (CULATR) at the University of Hong Kong. New-born Zmpste24$^{-/-}$ mice and wild-type controls were fed with resveratrol (20 µg/ml) or N-acetyl Cysteine (1 mg/ml) in drinking water. The survival of resveratrol-treated, NAC-treated, or vehicle-treated Zmpste24$^{-/-}$ mice was recorded and their body weight was monitored weekly. The trabecular bone organization and bone mineral density were determined by micro-CT. The survival rate was analyzed by Kaplan-Meier method and statistical comparison was performed by Log-rank (Mantel-Cox) Test.

Bone Marrow Stromal Cells and Hematopoietic Stem Cells

Bone marrow stromal cells were isolated and cultured according to modified protocol (Enumeration and Expansion of Mouse Mesenchymal Progenitor Cells Using MESENCUILT®, Stemcell Technologies, Canada). Briefly, bone marrow cells were flushed out from femurs and tibias with α-MEM (Invitrogen, Carlsbad, Calif., USA) supplemented with 20% FBS, and plated in petri dishes. Non-adherent cells were removed on day 3 and medium was replaced every 3 days. BMSC colonies were fixed with methanol and stained with crystal violet solution on the indicated day. For magnetic enrichment, CD11b-positive population was removed using a MIDIMACS™ magnetic cell sorting kit (Miltenyi Biotec, Bergisch Gladbach, Germany), following the manufacturer's instructions. Colonies containing more than 50 cells were counted. BMSC colony forming efficiency was calculated as number of colonies formed by 10$^7$ bone marrow nucleated cells.

To analyze hematopoietic stem cells, mononucleated cells were collected by flushing femurs and tibias with staining medium (HBSS supplemented with 2% FBS) and stained with biotin-coupled lineage markers, Biotin-Flt3, PE-Sca-1, APC-c-Kit, and then SAv-PerCP. FACS profile analyses were performed using a BD FACSCalibur.

To purify HSCs, red blood cells were lysed using $NH_4Cl$ before surface-marker staining, and HSCs were then sorted with a BD FACSVantage SE. Sorted HSCs were incubated with 5 µM DCF-DA at 37° C. for 30 min and analyzed by FACS at 488-nm excitation and 525-nm emission to determine the ROS level.

For hematopoictic reconstitution, recipient mice (B6SJL/BoyJ) were lethally irradiated with a dose of 9 Gy using a GAMMACELL™ 3000 Elan irradiator and 500 purified donor HSCs were injected into recipients via the tail vein. After repopulation, peripheral blood was collected, stained for cell surface markers, and analyzed by FACS.

SA-β-Galactosidase Assay

SA-β-galactosidase assay was performed using a Cellular Senescence Assay Kit (Chemicon International, CA, USA), following the manufacturer's instructions. For MEFs, resveratrol was supplemented in the complete medium at passage 4 and SA-β-galactosidase assay was performed at passage 6. To quantify SA-β-galactosidase staining, the blue-dyed precipitate was extracted with 100 µl DMSO and the absorbance at 415 nm was recorded.

Immunofluorescence Staining

BMSCs were grown on chamber slides, fixed in 4% paraformaldehyde and then blocked in 1% BSA/PBS with 5% normal serum overnight at 4° C., and then incubated with primary antibody diluted in 1% BSA/PBS at 4° C. overnight in a humid box. The slides were washed 3 times with PBS, incubated with FITC- or TRITC-coupled secondary antibodies diluted in 1% BSA/PBS for 40 min at R.T., washed 3 times with PBS to remove unbound antibodies, mounted with SLOWFADE® Gold antifade reagent with DAPI (Invitrogen, USA), sealed with nail polish and subjected for microscopy analysis. Photos were processed with PHOTOSHOP CS®.

Protein Extraction, Fractionation, Western Blotting, and Co-Immunoprecipitation

Whole cell lysate was prepared by suspending the cells in 5 volumes of suspension buffer (0.1 M NaCl, 10 mM Tris-HCl, pH 7.5, 1 mM EDTA, 1 mM DTT, pH 8.0, protease inhibitors), and then adding 5 volumes of Laemmli buffer (0.1 M Tris-HCl, pH 7.0, 4% SDS, 20% glycerol, 1 mM DTT, protease inhibitors) and boiling for 5 min.

Cells were fractionated as described (Mendez and Stillman, 2000). Briefly, the cells were suspended in 100 µl ice-cold buffer A (10 mM HEPES, pH 7.9, 10 mM KCl, 1.5 mM $MgCl_2$, 0.34 M sucrose, 10% glycerol, 1 mM DTT, protease inhibitors). After the addition of 0.1% Triton X-100, the cell suspension was mixed gently, incubated on ice for 5 min and centrifuged at 1300×g at 4° C. for 4 min. The supernatant (S1) was transferred to a new tube and clarified by high-speed centrifugation (12000×g, 10 min, 4° C.). The remaining nuclei pellet (P1) was washed once with 100 μl buffer A and then resuspended in 100 μl buffer A supplemented with 1 mM $CaCl_2$ and 2 units of micrococcal nuclease, and incubated at 37° C. for 15 min. The reaction was stopped by adding 1 mM EGTA and the suspension was then centrifuged at 1300×g at 4° C. for 4 min. The resultant pellet was resuspended in 100 μl of buffer B (3 mM EDTA, 0.2 mM EGTA, 1 mM DTT) and centrifuged at 1700×g at 4° C. for 4 min. The supernatant (S2'), containing all the soluble components of the nucleoplasm and chromatin-bound proteins, was transferred to another tube; the remaining pellet (P2'), containing all the nuclear matrix components, was suspended in 100 μl Laemmli buffer and boiled for 5 min.

Western blotting was performed as described previously (Liu et al., 2005). Relative band intensity was measured by IMAGE J® and normalized to corresponding wild-type or untreated controls as indicated.

For statistical analysis, at least three independent immunoblots were quantified and student T test was used for P values.

For co-immunoprecipitation, cells were lysed into pre-chilled RIPA buffer containing 300 mM or 500 mM NaCl and protease inhibitors. Primary antibodies or appropriate control IgGs were added to the lysate and incubated for 2 h on a rocking platform at 4° C. before Agarose beads were added and incubated O/N. The beads were washed twice with RIPA buffer, resuspended into Laemmli buffer and boiled, and protein suspension was collected by centrifugation and stored for further analysis.

In Vitro SIRT1 Deacetylation Assay

SIRT1 deacetylation assay on fluorophore-conjugated synthetic p53 peptide was performed with SIRT1 Fluorimetric Drug Discovery Kit (Biomol, Hamburg, Germany) according to the manufactory's instruction. Cells were fractionated as described above except that protease inhibitors were NOT included and the nuclear matrix fraction was suspended into the assay buffer provided by the supplier. Different cell fractions or recombinant human lamin A (rhLamin A, Diatheva, Italy) were added in the reaction mix of SIRT1 Fluorimetric Drug Discovery Kit, incubated for 20 min at 37° C., and then the reaction was stopped and fluorescent signal was detected. SIRT1 deacetylase activity on native target was assayed using SIRT1 assay Kit from Sigma (USA). Constructs encoding FLAG-p53 and HA-p300 were co-transfected into HEK293 cells; FLAG-p53 was immunoprecipitated by anti-FLAG M2 Agarose (Sigma) followed by elution with FLAG peptide (Sigma). Purified acetyl FLAG-p53 was incubated with recombinant human SIRT1 (rhSIRT1) and NAD+ for 30 min at 37° C., in the presence or absence of rhLamin A or resveratrol. The acetylation level of FLAG-p53 was determined by Western blotting with pan anti acetyl lysine antibodies.

EXAMPLES

Following are examples that illustrate embodiments and procedures for practicing the invention. The examples should not be construed as limiting. All percentages are by weight and all solvent mixture proportions are by volume unless otherwise noted.

Example 1—SIRT1 Interacts with Lamin A while Prelamin A or Progerin Jeopardizes the Interaction To determine the potential involvement of SIRT1 in progeria, the potential interaction between lamin A and SIRT1 is examined by co-immunoprecipitation in HEK293 cells expressing ectopic FLAG-tagged SIRT1.

Figure 1B:
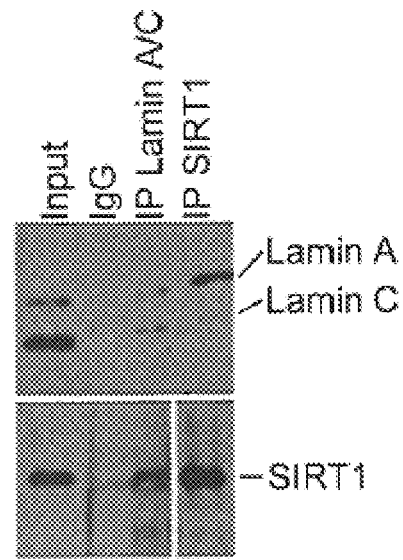

Lamin A was pulled down in the anti-FLAG immunoprecipitates, while FLAG-SIRT1 was detected in the anti-lamin A/C immunoprecipitates (FIG. 1A). The interaction between endogenous SIRT1 and lamin A/C was confirmed in HEK293 cells, bone marrow stromal cells (BMSCs), and mouse embryonic fibroblasts (MEFs), where anti-SIRT1 immunoprecipitates pulled down lamin A and vice versa (FIGS. 1B, 6A, 6B).

Figure 1E:
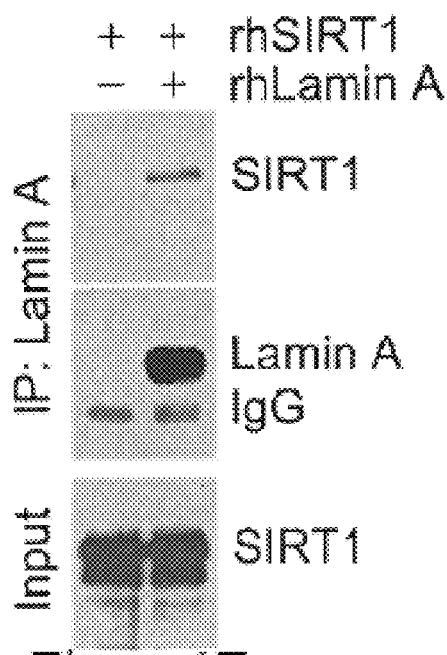

Immunofluorescence confocal microscopy showed that much of nuclear SIRT1 co-localized with nucleoplasmic lamin A/C in the nuclear interior in human fibroblasts (FIG. 1C). Consistently, ectopic EGFP-SIRT1 and DsRed-lamin A co-existed in the nuclear interior (FIG. 1D). This interaction seems specific to nuclear SIRT1 as neither cytoplasmic SIRT1 nor mitochondrial SIRT5 was detected in the anti GFP-lamin A immunoprecipitates (FIG. 6C). In addition, SIRT1 physically interacts with lamin A as recombinant human SIRT1 (rhSIRT1) was pulled down by recombinant human lamin A (rhLamin A) in a test tube (FIG. 1E).

Alternative splicing of LMNA gives rise to different A-type lamins, of which lamin A and C are the most abundant (Lin and Worman, 1993). Lamin A and C share the first 566 amino acids; lamin A has a specific 98-amino-acid carboxyl tail, and lamin C has a unique 6-amino-acid carboxyl tail (Liu and Zhou, 2008).

Figure 1F:
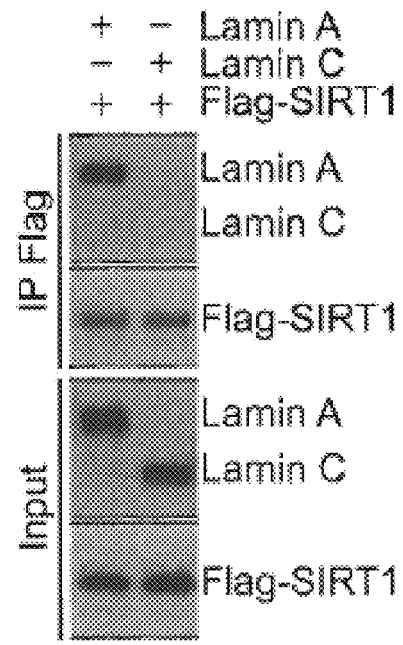

Although the level of lamin C was much higher than A in HEK293 cells, lamin C was hardly detected in the anti-SIRT1 immunoprecipitates (FIG. 1B), indicating that lamin A likely interacts with SIRT1 via its C-terminal domain. This was further confirmed by co-immunoprecipitation in HEK293 cells expressing FLAG-SIRT1 together with either lamin A or lamin C. As shown in FIG. 1F, lamin A was detected in the anti-FLAG-SIRT1 immunoprecipitates, whereas lamin C was negligible.

It is widely accepted that the unprocessed C-terminal tail in progerin or prelamin A is responsible for the progeroid features in HGPS and progeria mouse models. Given that lamin A interacts with SIRT1 via its C-terminal domain, this Example examines whether the interaction between SIRT1 and prelamin A or progerin is reduced compared to lamin A. Co-immunoprecipitation was performed in HEK293 cells expressing FLAG-SIRT1 together with one of the A-type lamins, i.e., wild-type lamin A, prelamin A or progerin.

Figure 1G:
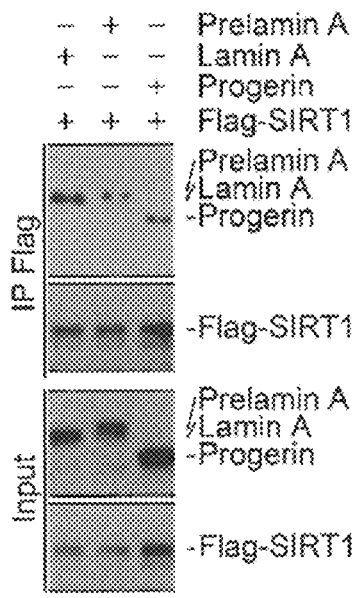
Figure 1H:
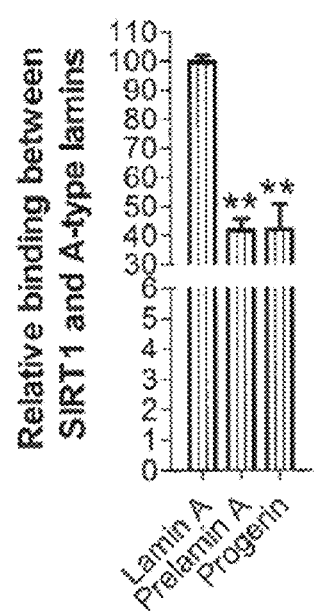
(FIG. 1H) Quantification of (FIG. 1G). Data represent mean±SEM, n=3. **P<0.01.

As shown in FIGS. 1G, 1H, significantly less prelamin A and progerin were pulled down by anti-FLAG antibodies compared with lamin A, though comparable or higher levels of FLAG-SIRT1 and prelamin A/progerin were present in the input. The results indicate that SIRT1 preferentially interacts with lamin A whereas prelamin A or progerin has significantly reduced association with SIRT1.

Example 2—SIRT1 is Mislocalized in Progeria Cells

Lamin A is one of the major components of NM. This Example investigates the association of SIRT1 with the NM by subcellular fractionation. SIRT1$^{-/-}$ cells were utilized as a negative control for the specific staining of SIRT1 protein. KAP-1 (KRAB-associated protein 1, also known as Trim28 or Tif1β) and MCM3 proteins served as positive controls for the purity of the subcellular fractionation.

KAP-1 is a heterochromatin factor and was reported to be associated with the majority of the micrococcal nuclease-resistant fraction in the nucleus (Goodarzi et al., 2008; Ryan et al., 1999). MCM3 protein is important in preventing excessive DNA replication during S phase and is predominantly associated with chromatin (Mendez and Stillman, 2000).

Figure 7E:
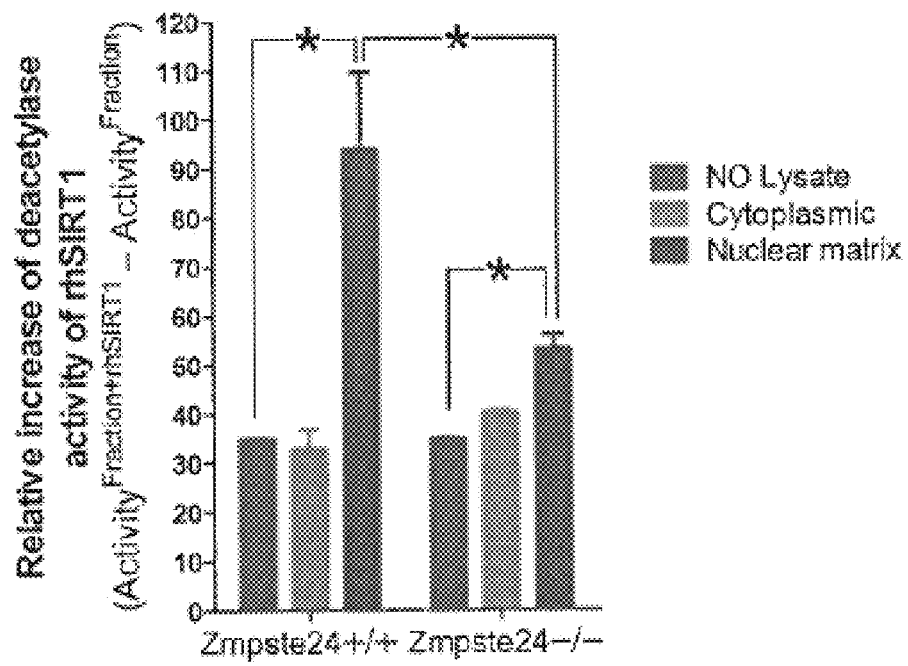

As expected, Kap-1 was resistant to MNase digestion and remained in the NM fraction (P2') whereas the majority of Mcm3 was released into the nucleoplasmic and chromatic fraction (S2') after MNase treatment (FIG. 7A). Consistent with its interaction with lamin A, SIRT1 protein was enriched in the NM fraction (P2') in MEFs (FIG. 7B).

Since prelamin A has less binding capacity to SIRT1 compared with lamin A and SIRT1 is highly expressed in stem cells (Saunders et al., 2010), this Example also examines SIRT1 localization in Zmpste24$^{-/-}$ cells by subcellular fractionation in multipotent BMSCs.

Figure 2A:
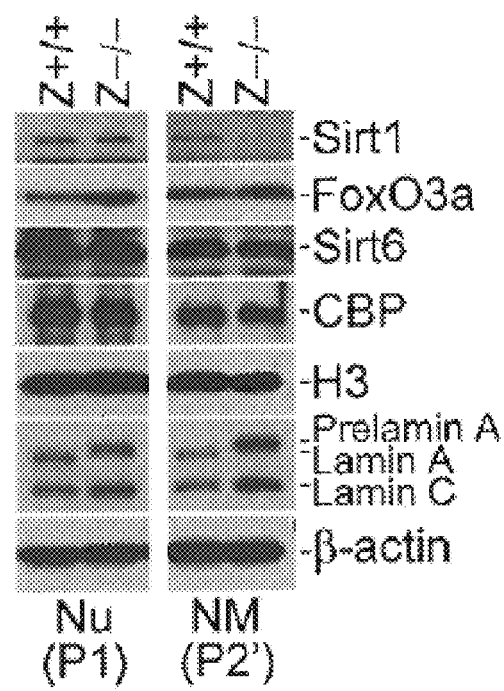
FIGS. 2A-2G show mislocalization and reduced deacetylase activity of SIRT1 in progeroid cells.
Figure 2B:
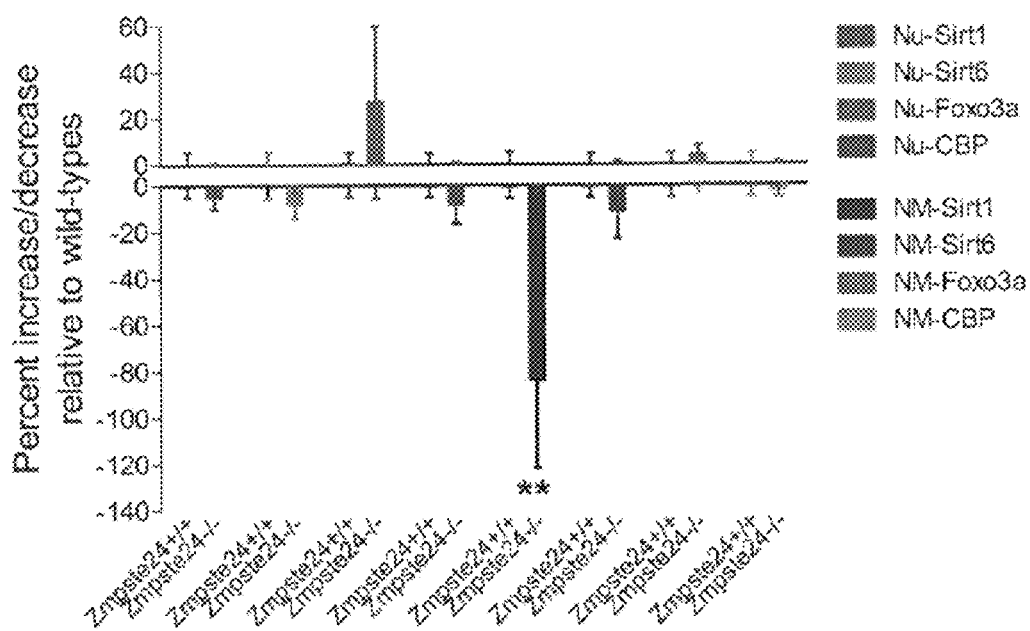

NM-associated SIRT1 was largely reduced in Zmpste24$^{-/-}$ BMSCs compared to wild type controls, though total nuclear proportion of SIRT1 was comparable (FIGS. 2A, 2B). The reduction in NM-associated SIRT1 appears specific, because Sirt6, CBP acetyltransferase and Foxo3a were not significantly affected in Zmpste24$^{-/-}$ cells.

The NM-associated SIRT1 was also reduced in HGPS dermal fibroblasts, including HGADFN143, HGADFN188, HGADFN164 and HGADFN122, compared to either healthy F2-S fibroblasts or dermal fibroblasts harboring non-progeria LMNA mutations, i.e., R453W in Emery Dreifuss Muscular Dystrophy (EDMD), R482W in Familial Lipodystrophy (FLPD) and R401C in EDMD (Liu and Zhou, 2008) (FIGS. 7C, 7D).

Figure 2C:
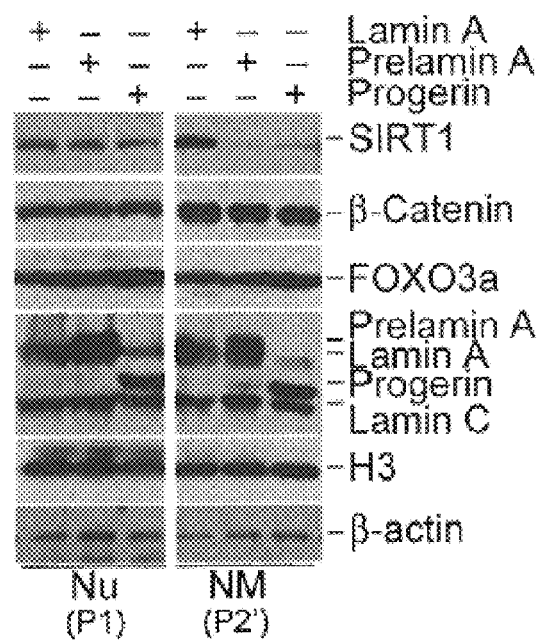
Figure 2D:
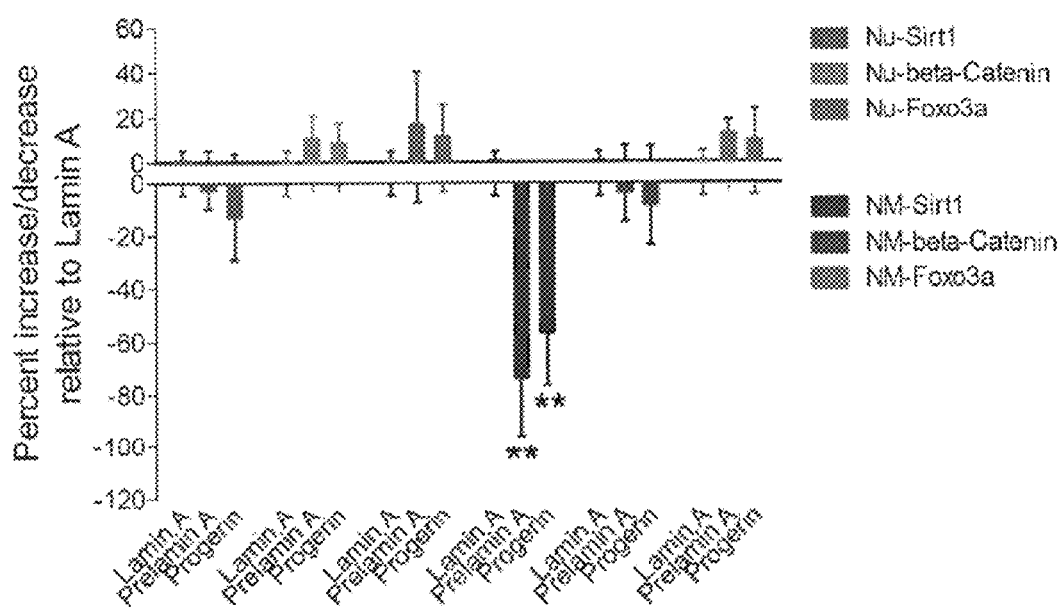

Though total nuclear level of SIRT1 was variable in different HGPS cell lines, the percentage of NM-associated SIRT1 was consistently reduced. Moreover, ectopic expression of prelamin A and progerin caused remarkable disassociation of SIRT1 from the NM, while the nuclear level of SIRT1 was hardly affected in HEK293 cells (FIGS. 2C, 2D). The results indicate that prelamin A or progerin compromises the proper NM localization of SIRT1.

To further assess the functional significance of mislocalization of SIRT1, this Example examines SIRT1 downstream pathway(s) in progeria cells. SIRT1 deacetylates Foxo3a and upregulates its transcriptional activity, thus promoting expression of antioxidant enzymes such as MnSOD and catalase in response to oxidative stress (Brunet et al., 2004).

Figure 2E:
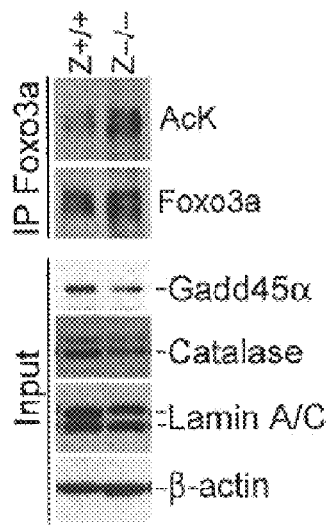
Figure 2F:
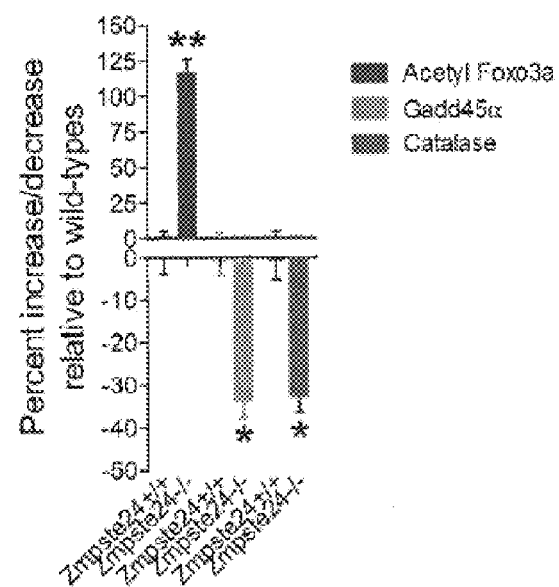
Figure 2G:
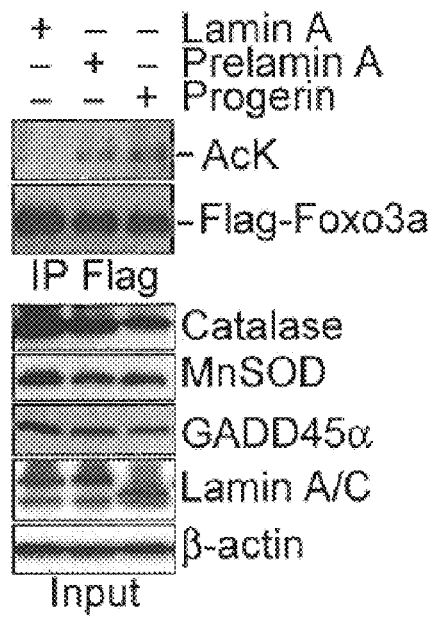

Consistent with the mislocalization of SIRT1, Foxo3a was hyper-acetylated in Zmpste24$^{-/-}$ BMSCs and the level of catalase and Gadd45α was reduced by approximately 40% in Zmpste24$^{-/-}$ mice relative to wild-type controls (FIGS. 2E-F). The increase in Foxo3a acetylation is likely the result of decreased SIRT1 deacetylase activity in vivo, as neither total nuclear SIRT1 level nor NM association of CBP, the acetyltransferase for Foxo3a, was changed in Zmpste24$^{-/-}$ BMSCs (FIGS. 2A-B). Ectopic expression of either prelamin A or progerin increased the acetylation of FOXO3A, and reduced the expression of catalase, MnSOD and GADD45α in HEK293 cells (FIG. 2G).

Example 3—Resveratrol Enhances the Binding of SIRT1 to Lamin A and Stimulates its Deacetylase Activity in a Lamin A-Dependent Manner The NM-localization of SIRT1 and the association of NM with HDAC deacetylase activity (Fey et al., 1991) suggest that NM might contain potential SIRT1 activators. To test this hypothesis, in vitro deacetylase activity of rhSIRT1 by a BIOMOL® SIRT1 Fluorimetric Drug Discovery Kit (BSDK) was quantified in the presence or absence of NM derived from wild-type or Zmpste24–/– BMSCs.

Surprisingly, the deacetylase activity of rhSIRT1 was enhanced approximately 3-fold in the presence of NM from wild-type BMSCs compared with the control without NM or with cytoplasmic fraction (FIG. 7E), suggesting the existence of potential SIRT1 activator(s) on the NM. In contrast, the NM from the Zmpste24$^{-/-}$ BMSCs showed a significantly reduced stimulatory effect on rhSIRT1 deacetylase activity.

This Example further investigates whether lamin A acts as an activator of SIRT1. In mammalian cells, lysine acetyltransferase p300 and SIRT1 mediate the acetylation and deacetylation of p53 on residue K382 (Gu and Roeder, 1997). BSDK utilizes fluorophore-conjugated acetyl p53 peptide as target (see Materials and Methods). As shown in FIG. 3A, in the presence of rhLamin A, the deacetylase activity of rhSIRT1 on acetyl p53 peptide was increased in a dose-dependent manner. Lamin A-stimulated SIRT1 deacetylase activity was completely abolished by SIRT1 inhibitor Suramin.

To further test the effect of rhLamin A on the native target of SIRT1, acetyl p53 was purified by anti-FLAG immunoprecipitation in HEK293 cells ectopically expressing FLAG-p53 and p300, and SIRT1 deacetylation assay was performed as described in Materials and Methods.

As shown in FIG. 3B and S2F, around 20% decrease in FLAG-p53 acetylation level was observed in the presence of rhLamin A-rhSIRT1 complex compared with rhSIRT1 only, suggesting that lamin A serves as an activator of SIRT1.

Resveratrol, which might be a potential SIRT1 activator, has been reported to enhance healthspan in a range of age-related diseases. However several independent studies found that resveratrol activates SIRT1 towards the fluorophore-conjugated synthetic p53 peptide rather than unconjugated native targets (Barra et al., 2005; Burnett et al., 2011; Dai et al., 2010; Kaeberlein et al., 2005; Pacholec et al., 2010).

Figure 3E:
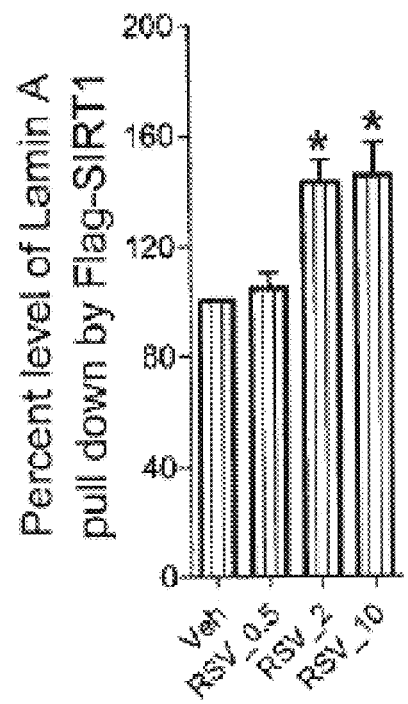
Figure 7F:
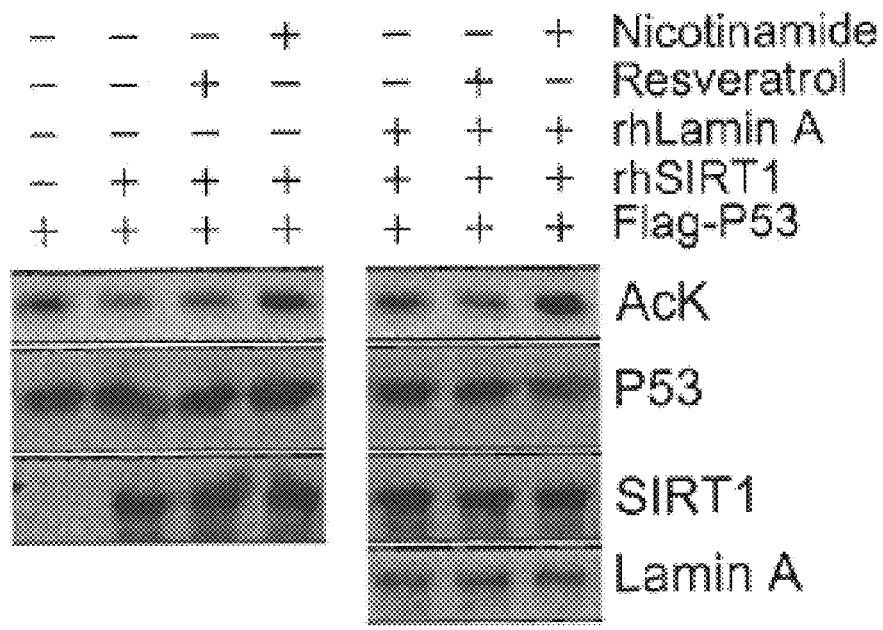

This Example shows that resveratrol does not directly activate SIRT1 deacetylase activity using native full-length FLAG-p53 as a substrate (FIG. 7F). Surprisingly, in the presence of rhLamin A, resveratrol activated SIRT1 in a lamin A dose-dependent manner (FIGS. 3B, 7F). Further examination revealed that resveratrol enhanced the binding of rhSIRT1 to rhLamin A in the test tube (FIG. 3C) and the binding of FLAG-SIRT1 to lamin A in HEK293 cells (FIGS. 3D, 3E) by co-immunoprecipitation.

Figure 3F:
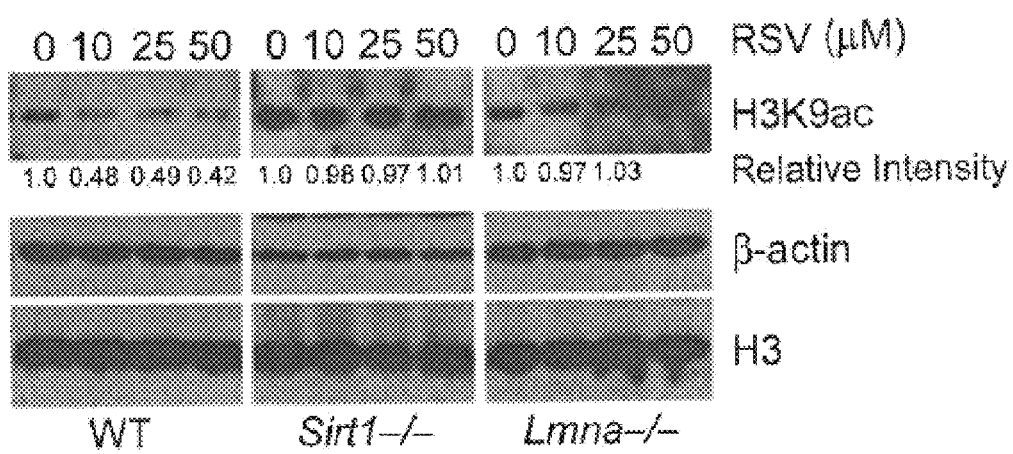
Figure 3G:
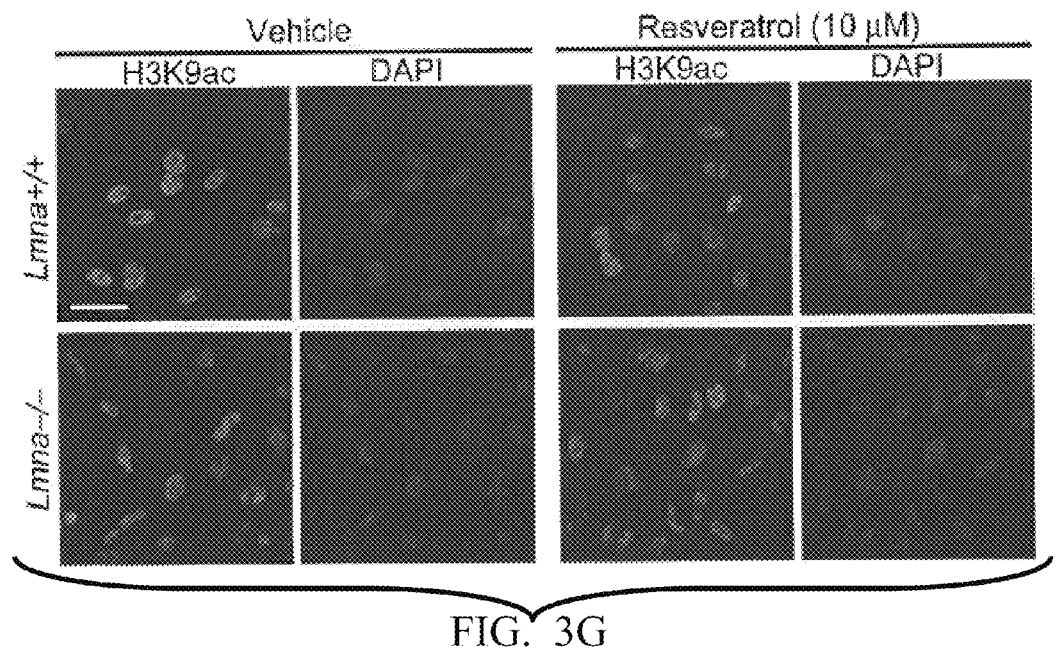

In addition to acetyl p53, H3K9ac is another substrate of SIRT1 deacetylase (Wang et al., 2008). This Example further investigates the effects of resveratrol on H3K9ac in the wild-type, SIRT1$^{-/-}$ or Lmna null cells. As shown in FIG. 3F, treatment with resveratrol downregulated the level of H3K9ac in wild-type cells in a dose-dependent manner, while this effect was completely abrogated in SIRT1$^{-/-}$ or Lmna$^{-/-}$ cells. Anti-H3K9ac immunofluorescence staining further confirmed the lamin A-dependent activation of SIRT1 by resveratrol (FIG. 3G).

Figure 3H:
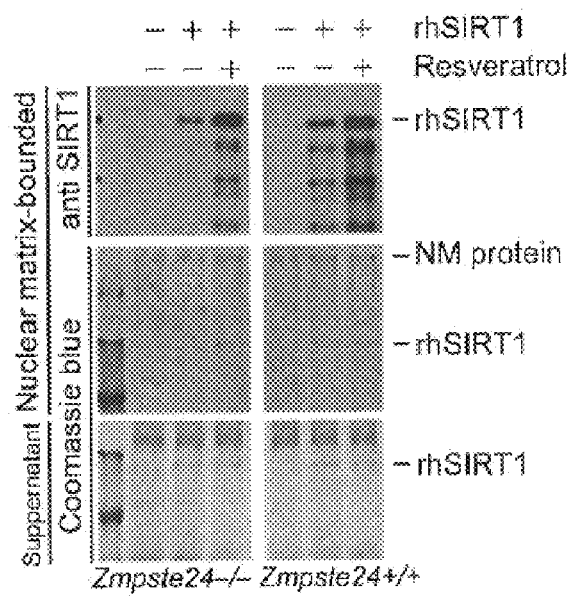

As SIRT1 interacts with lamin A and thus associates with NM and resveratrol increases the binding between lamin A and SIRT1, this Example also examines whether resveratrol enhances NM association of SIRT1. As shown in FIGS. 7G-H, in wild-type and Zmpste24$^{-/-}$ BMSCs incubated with different concentrations of resveratrol, NM-associated SIRT1 was increased compared to untreated controls. The ability of resveratrol to stimulate the NM association of SIRT1 was also observed in test tube. When equal amounts of rhSIRT1 were incubated with the insoluble NM fraction from either wild-type or Zmpste24$^{-/-}$ cells suspended in BSDK assay buffer, significant less NM-bound rhSIRT1 was found in precipitates from Zmpste24$^{-/-}$ NM relative to wild-type NM precipitates in the absence of resveratrol (FIG. 3H). Significantly, the presence of resveratrol enhanced the association of rhSIRT1 with NM derived from both wild-type and Zmpste24$^{-/-}$ cells. Consistently, rhSIRT1 level in the supernatant underwent a compensatory reduction (FIG. 3H). Collectively, these data indicate that resveratrol could enhance the interaction between lamin A and SIRT1 to increase the NM association of SIRT1 and thus activates SIRT1.

Example 4—Resveratrol Treatment Rescues ASC Decline in Zmpste24$^{-/-}$ Mice

Figure 8B:
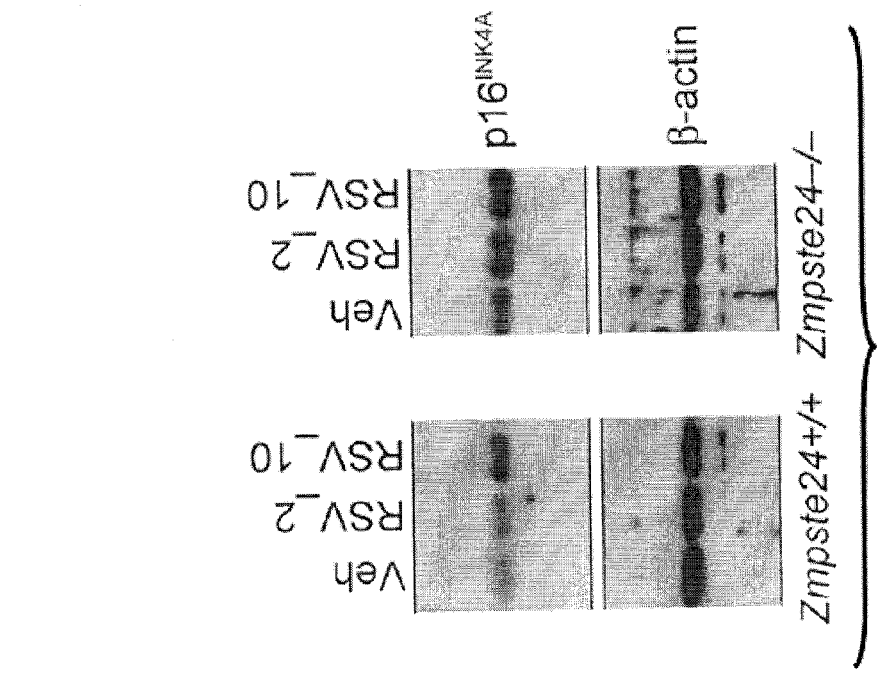
FIGS. 8A-8B show effects of resveratrol on Zmpste24$^{-/-}$ mouse embryonic fibroblasts (MEFs).
Figure 8A:
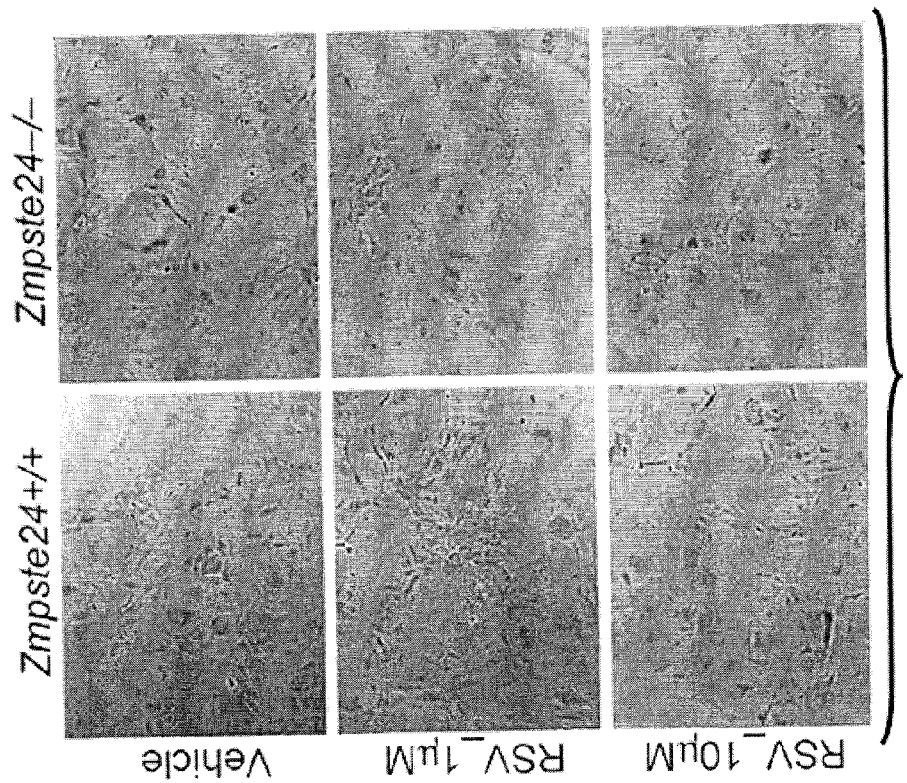

As resveratrol enhances SIRT1 deacetylase activity by increasing its binding to lamin A, this Example examines the effects of resveratrol treatment on the early senescence in Zmpste24$^{-/-}$ MEFs. However, no obvious difference in β-galactosidase activity was observed between resveratrol-treated and saline-treated Zmpste24$^{-/-}$ MEFs (FIG. 8A), and resveratrol did not reduce the elevated levels of p16$^{ink4a}$ in Zmpste24$^{-/-}$ MEFs (FIG. 8B). As SIRT1 is more highly expressed in stem cells than in somatic differentiated cells and it is critical for maintaining stem cell self-renewal and function (Han et al., 2008; Lee et al., 2011; Saunders et al., 2010), we then tested effects of resveratrol on BMSCs.

Figure 4E:
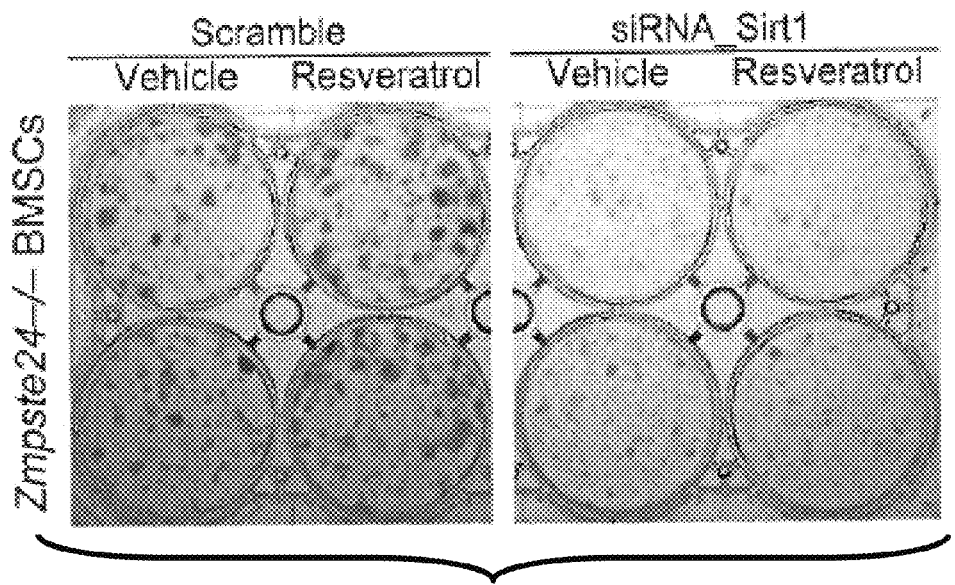
Figure 4F:
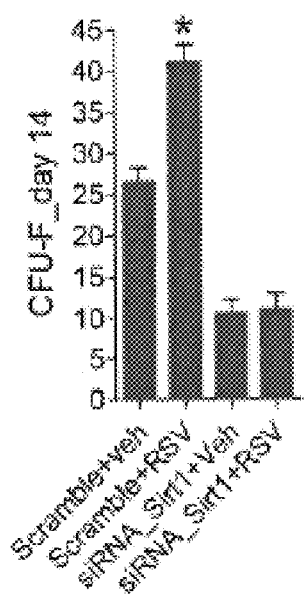
Figure 4G:
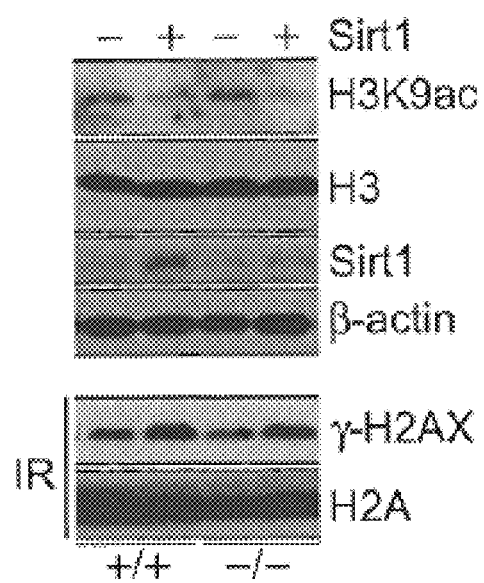
Figure 4H:
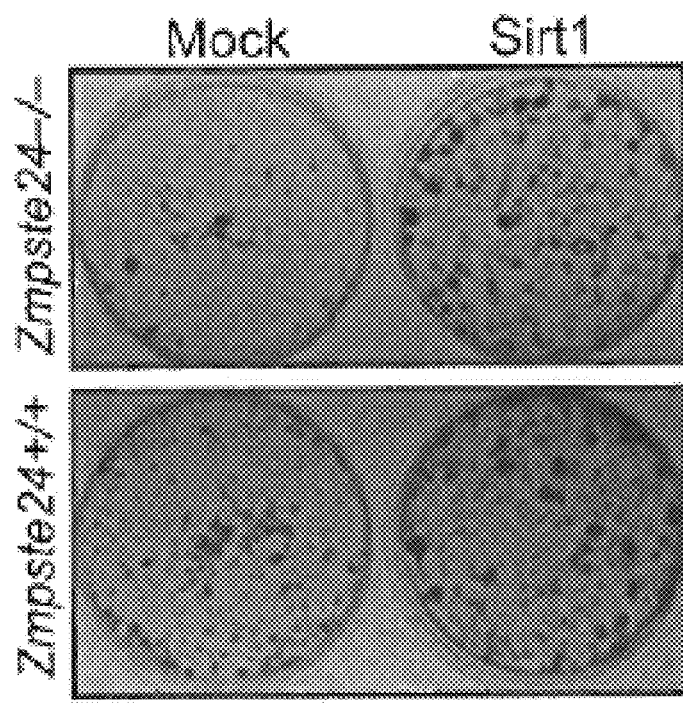
Figure 4I:
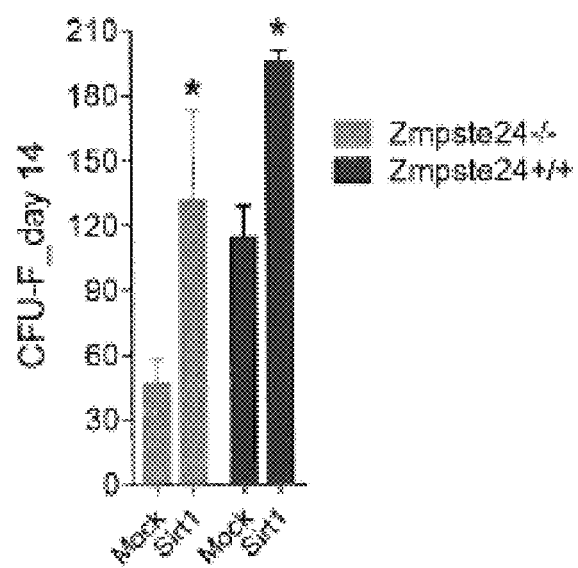
Figure 9A:
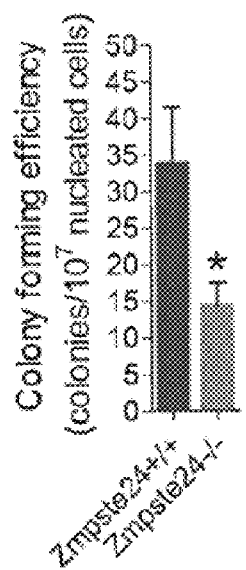
Figure 9B:
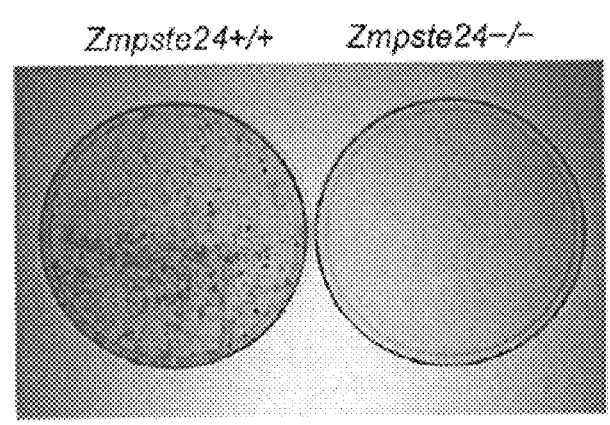
Figure 9C:
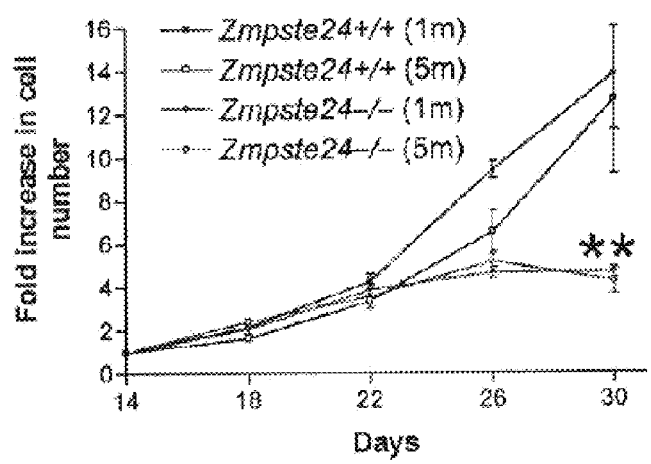
Figure 9G:
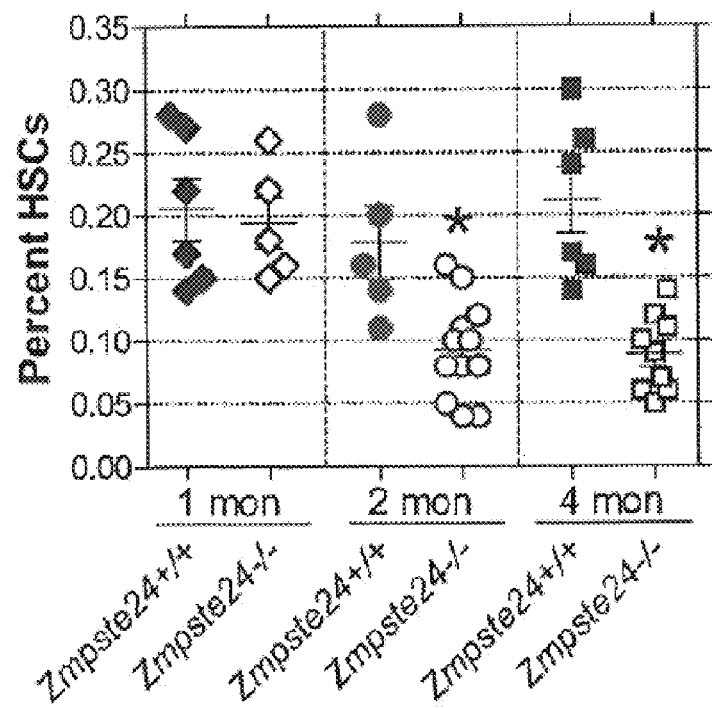
Figure 9H:
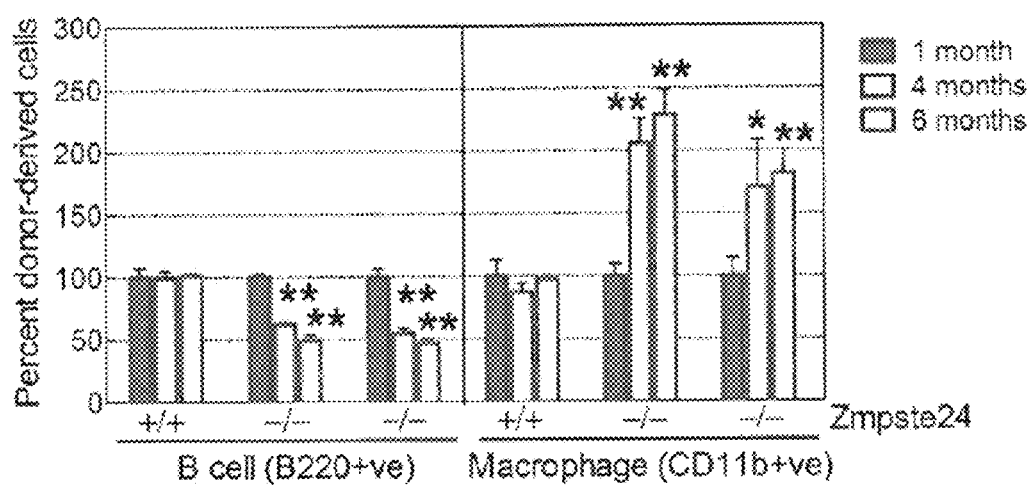
Figure 10C:
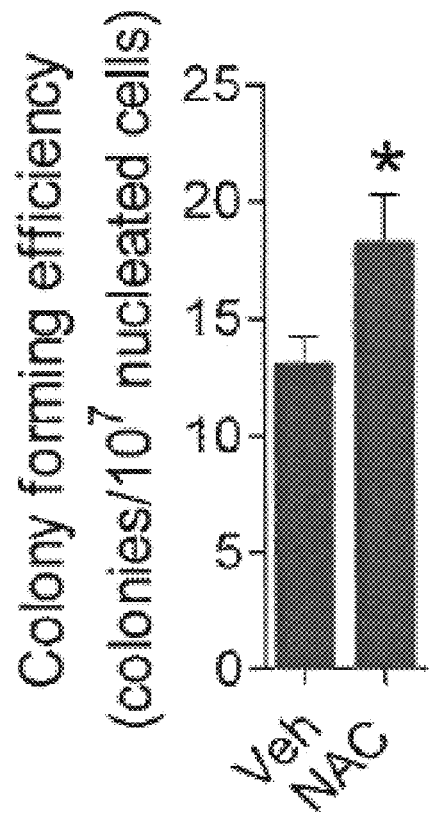
Figure 10D:
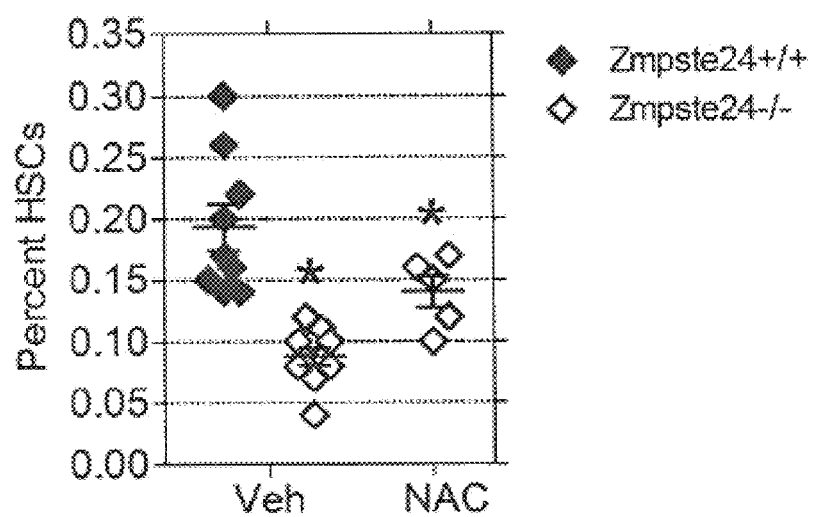
Figure 10E:
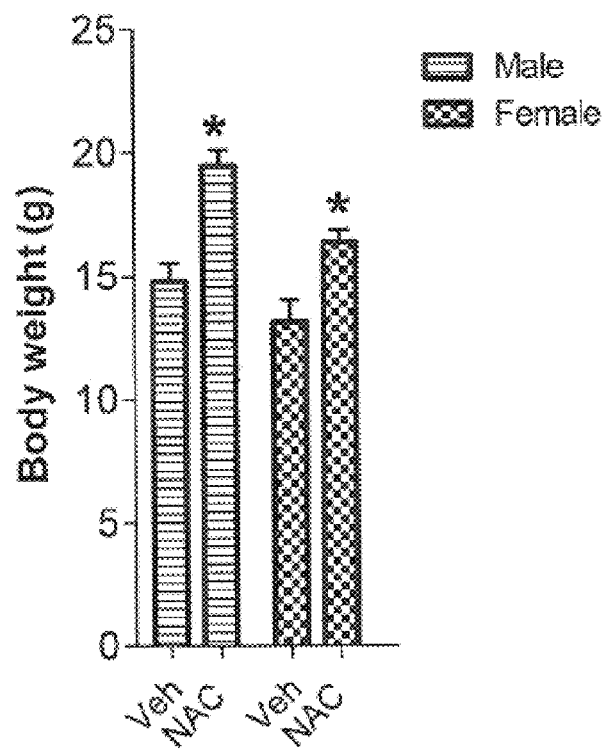
Figure 10F:
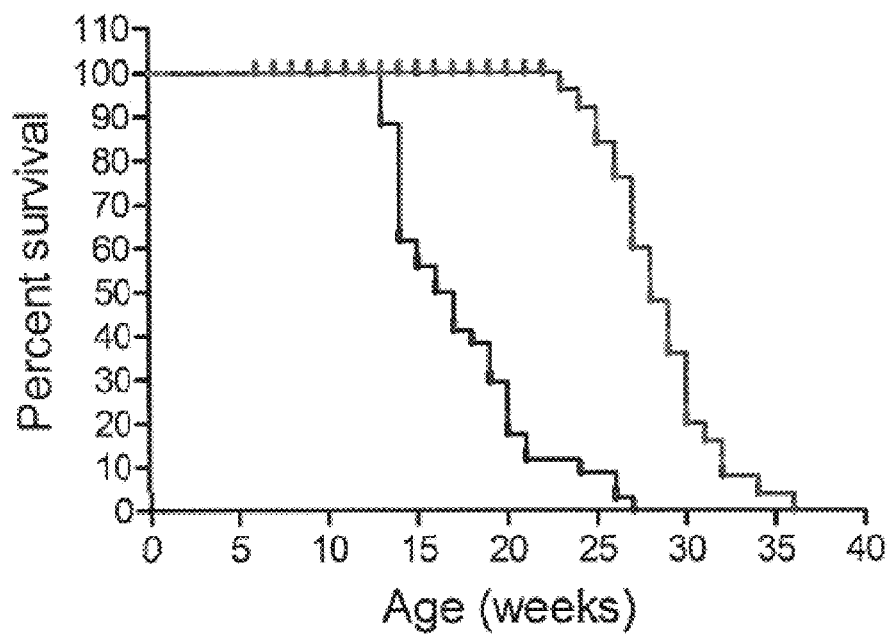
Figures 11A, 11B, 11C:
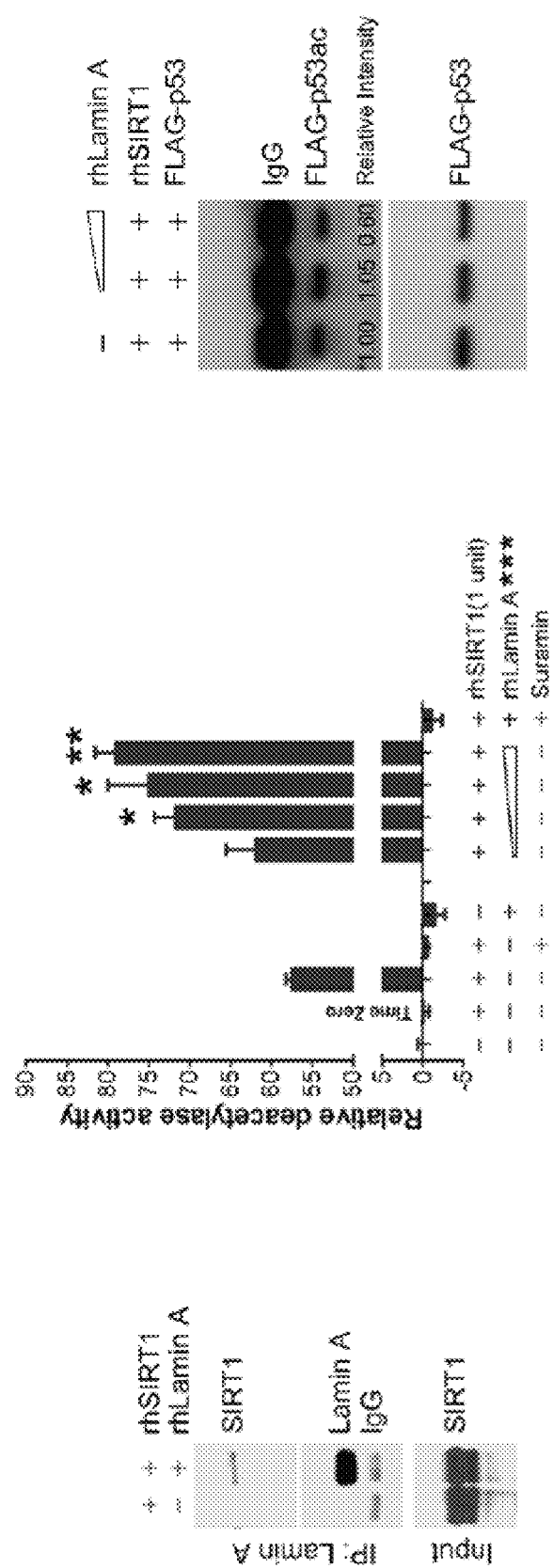
FIGS. 11A-11E (FIG. 11A) Recombinant human SIRT1 (rhSIRT1) was pulled down by anti lamin A immunoprecipitates in test tube containing rhSIRT1 and recombinant human lamin A (rhLamin A).
Figure 11D:
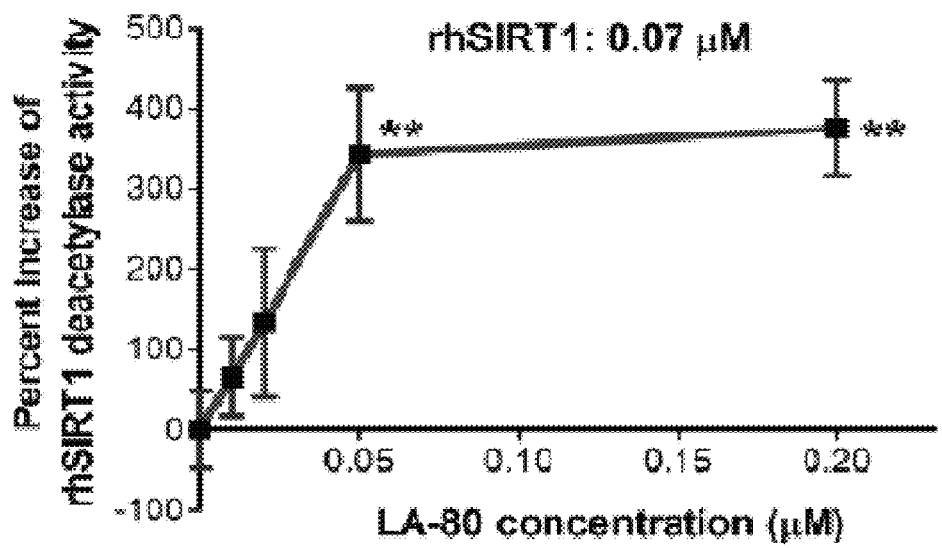
Figure 11E:
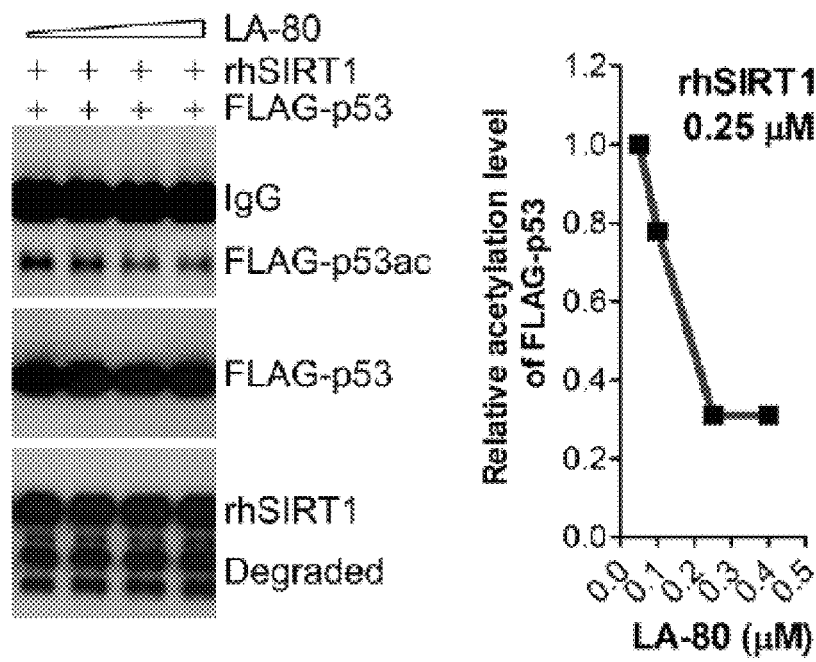

Progerin and prelamin A have been previously linked to defects in mesenchymal stem cells (MSCs) and in hair follicle progenitor cells in Zmpste24$^{-/-}$ mice (Espada et al., 2008; Scaffidi and Misteli, 2008). Consistently, the number of BMSCs was significantly reduced in Zmpste24$^{-/-}$ mice compared with wild-type controls at 4 months of age (FIG. 9A). Zmpste24$^{-/-}$ BMSCs in culture showed compromised colony-forming capacity (FIG. 9B), reduced proliferation (FIG. 9C), and a dramatically increased cellular senescence (FIG. 9D). Similarly, an early decline in mononucleated cells (MNCs) and hematopoietic stem cells (HSCs, Lineage$^-$Flt3$^-$Sca-1$^+$cKit$^{high}$) was observed in Zmpste24$^{-/-}$ mice (FIGS. 9E-G), such that by 4 months of age HSC levels fell to less than half of that of wild-type controls. HSC transplantation experiments showed that the self-renewal defects were cell-intrinsic (FIG. 9H). Interestingly, resveratrol enhanced the colony-forming capacity in Zmpste24$^{-/-}$ BMSCs in a dose-dependent manner (FIGS. 4A-B). The treatment also increased the binding of SIRT1 to prelamin A and the expression of Gadd45α and catalase (FIGS. 4C-D). Moreover, the rescue effect of resveratrol is SIRT1-dependent, as knocking down SIRT1 attenuated its effect on Zmpste24$^{-/-}$ BMSCs (FIGS. 4D-F). Knocking down SIRT1 abolished the stimulating effect of resveratrol on the expression of Gadd45α and catalase (FIG. 4D). In addition, knockdown of SIRT1 decreased colony-forming capacity (FIGS. 4E-F) and ectopic SIRT1 increased the colony-forming capacity of Zmpste24$^{-/-}$ BMSCs to levels comparable to that of wild-type BMSCs (FIGS. 4G-I). These data indicate that BMSC decline in Zmpste24$^{-/-}$ mice is attributable to impaired SIRT1 function which can be rescued by resveratrol.

Example 5—Resveratrol Alleviates Progeroid Features and Extends Lifespan in Zmpste24$^{-/-}$ Mice As the SIRT1-dependent rescue of BMSC colony-forming capacity in vitro, this Example examines whether resveratrol could rescue the BMSC defects in Zmpste24$^{-/-}$ mice in vivo.

Briefly, resveratrol was supplemented at a concentration of 20 µg/ml in drinking water. Four months after treatment, BMSCs were collected for examination and comparison between resveratrol-treated and vehicle-treated Zmpste24$^{-/-}$ mice.

Figure 5E:
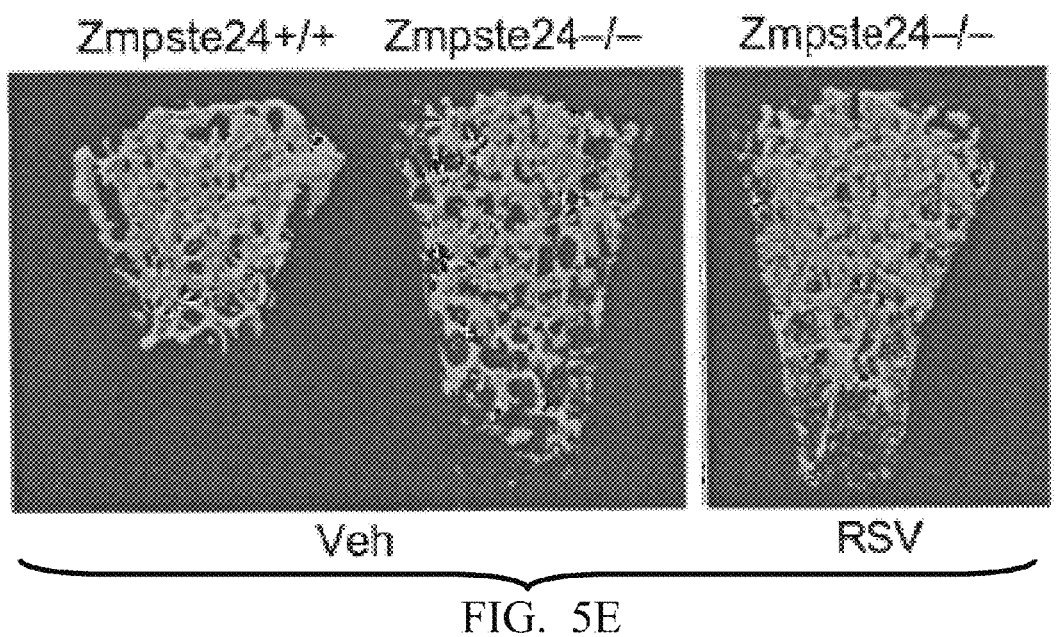
Figure 5F:
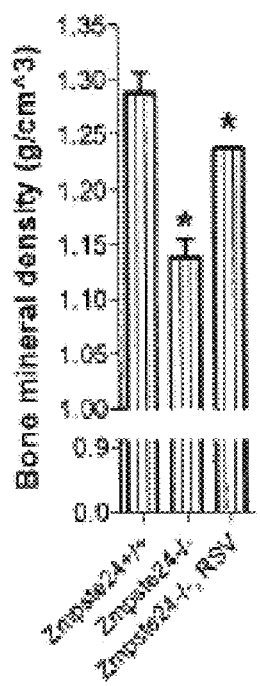
Figure 5G:
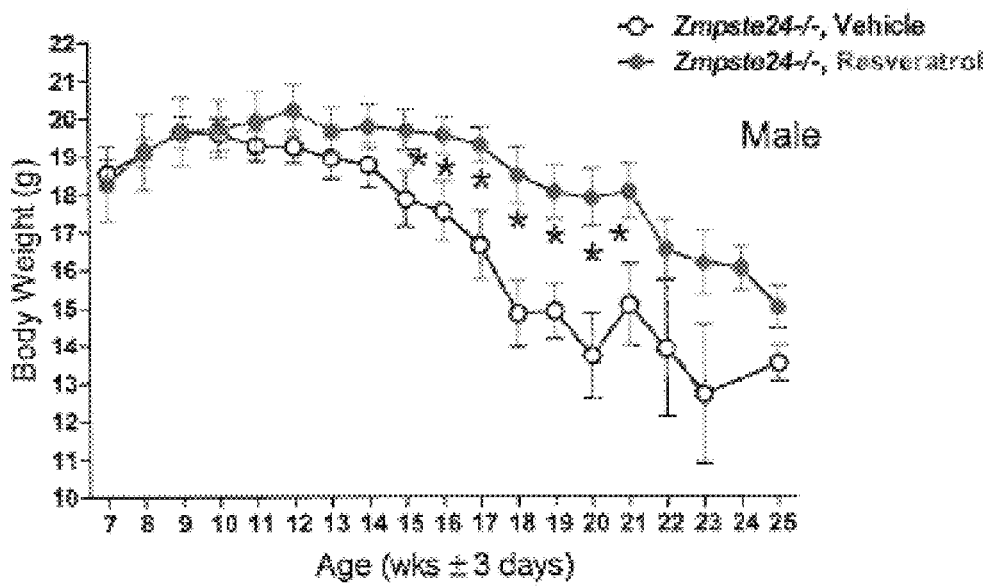
Figure 5H:
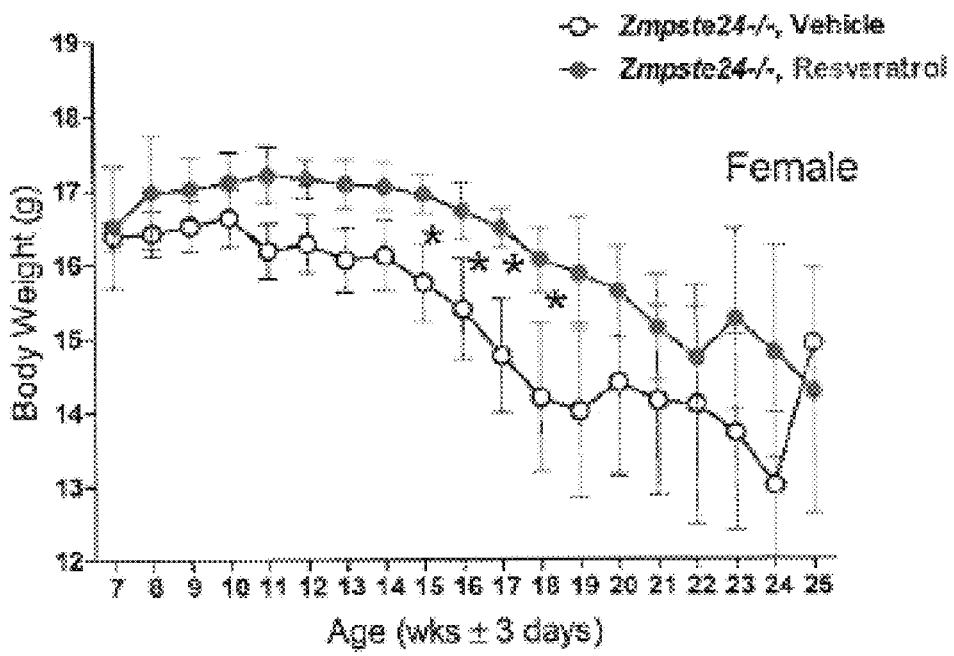
Figure 5I:
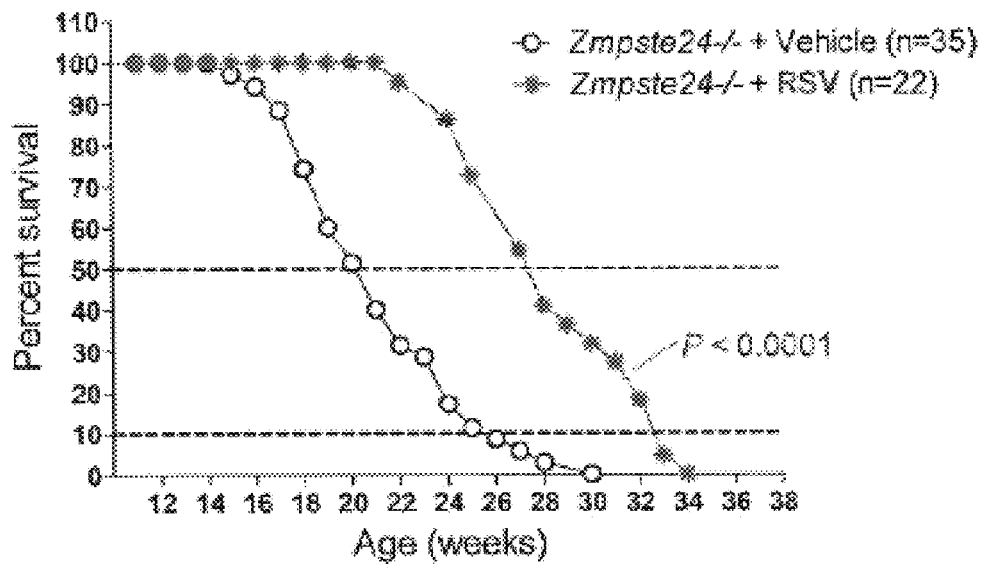
Figure 5J:
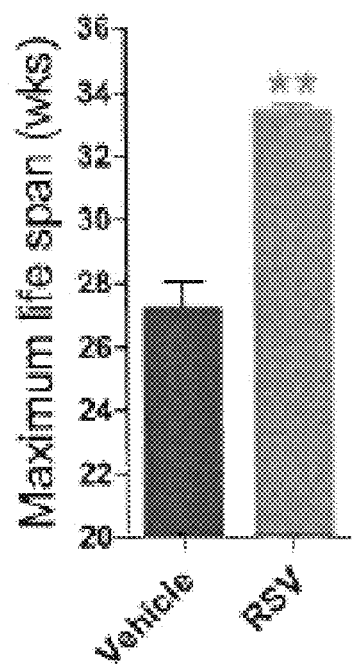

As shown in FIGS. 5A and 5B, BMSC colony-forming efficiency was significantly increased in the resveratrol-treated group. Concomitantly, resveratrol treatment enhanced the level of catalase whereas it decreased the level of acetyl p53 and H3K9 in BMSCs (FIG. 5C). Resveratrol-treatment also rescued the early decline in HSCs (FIG. 5C). Moreover resveratrol-treatment ameliorated progeroid features in Zmpste24$^{-/-}$ mice. As shown by micro-CT analyses, the trabeculae in Zmpste24$^{-/-}$ mice appeared to be thinner and more widely spaced. After 4 months of treatment, resveratrol increased the trabecular thickness, improved the structural organization and increased bone mineral density (FIGS. 5D-E). In addition, resveratrol-treatment also significantly slowed down the body weight loss, compared to vehicle-treated controls (FIGS. 5F-G). Most importantly, the median survival was extended from 20 weeks in vehicle-treated Zmpste24$^{-/-}$ mice to 27 weeks in resveratrol-treated Zmpste24$^{-/-}$ mice (FIG. 5H). By 26 weeks after birth, 95% of Zmpste24$^{-/-}$ mice had died, whereas nearly 60% of resveratrol-treated animals were still alive. The maximum lifespan (mean lifespan of the longest-lived 10% of the animals) was prolonged from 27.5 weeks in vehicle-treated to 33.5 weeks in resveratrol-treated Zmpste24$^{-/-}$ mice (FIG. 5I).

Resveratrol rescues SIRT1-dependent decline in adult stem cell numbers and alleviates progeroid features in laminopathy-based progeria. Mice lacking Zmpste24, a metalloproteinase responsible for prelamin A processing, recapitulate many of the HGPS features, including accelerated cellular senescence and dysfunctional adult stem cells (ASCs). SIRT1 directly interacts with lamin A, and thus, localizes on the nuclear matrix (NM). The association of SIRT1 with lamin A and NM enhances its deacetylase activity.

Compared with lamin A, prelamin A and progerin have significantly decreased interaction with SIRT1 in vivo and reduced activation of SIRT1 deacetylase activity, leading to rapid depletion of ASCs in laminopathy-based progeria mice. Resveratrol activates SIRT1 via increasing the binding of SIRT1 to A-type lamins and enhancing its NM association. Resveratrol treatment rescues ASC decline in a SIRT1-dependent manner, slows down body weight loss, improves trabecular bone structure and mineral density, and significantly extends the lifespan of Zmpste24$^{-/-}$ mice. The present invention shows that lamin A is an activator of SIRT1 and resveratrol directly activates SIRT1 in a lamin A-dependent manner. Further, the association between conserved SIRT1 longevity pathway and progeria indicates that the stem cell-based and SIRT1 pathway-dependent therapeutic strategies can be useful for treatment of progeria.

SIRT1 interacts with lamin A and associates with the NM; lamin A serves as an activator of SIRT1. SIRT1 interacts weakly with prelamin A or progerin, and SIRT1 abundance and activity in the NM is significantly reduced in progeria cells. Resveratrol directly activates SIRT1 through enhancing the binding between SIRT1 and A-type lamins and increasing the association of SIRT1 with the NM, which in turn rescues the defective BMSCs, ameliorates progeroid phenotypes, and extends the lifespan of Zmpste24$^{-/-}$ mice.

The present invention shows that lamin A directly interacts with SIRT1 and thus enhances deacetylase activity of SIRT1, using either AMC-conjugated synthetic peptide or native full-length acetyl p53. It is postulated that lamin A interacts with SIRT1 through its C-terminus, as the interaction between lamin C and SIRT1 is minimal. The unprocessed C-terminus in prelamin A or progerin may interfere with their binding with SIRT1, and therefore, reduce SIRT1 association on NM, leading to jeopardized deacetylase activity in progeria cells. Resveratrol enhances the binding of SIRT1 to A-type lamins and thus activates SIRT1 deacetylase activity.

Although many of the in vivo benefits of resveratrol are SIRT1-dependent (Baur, 2010), emerging evidence indicates that it also activates AMPK independent of SIRT1 (Canto et al., 2009; Gledhill et al., 2007; Hawley et al., 2010; Park et al., 2012). It was shown that low doses of resveratrol ($\leq 25$ µM) activates AMPK in a SIRT1-dependent manner, while high doses ($\geq 50$ µM) activate AMPK independent of SIRT1 (Baur et al., 2006; Price et al., 2012; Sun et al., 2007). In the present invention, low doses (2-10 µM) of resveratrol were used and activation of AMPK was not observed; therefore, it is postulated that the beneficial effects of resveratrol on BMSCs are primarily attributable to the activation of SIRT1. Interestingly, although resveratrol rescues BMSC decline in a SIRT1-dependent manner, ameliorates progeroid phenotypes and extends the lifespan of Zmpste24$^{-/-}$ mice, it does not rescue cellular senescence in Zmpste24$^{-/-}$ MEFs, suggesting that resveratrol treatment may affect somatic cells and ASCs differently.

Accordingly, it has been reported that resveratrol inhibits proliferation of somatic cells of different origins and in various cancer cell lines (Sgambato et al., 2001). As the effects of resveratrol are pleiotropic (Harikumar and Aggarwal, 2008) and involve both sirtuin-dependent and independent pathways, it seems plausible that resveratrol could influence sirtuin and non-sirtuin pathways differently in ASCs and somatic cells.

Given the fact that SIRT1 expression is much higher in stem cells compared to that in somatic cells (Saunders et al., 2010), the different effects of resveratrol on BMSCs and MEFs may also lie in the difference in level of SIRT1 expression. Indeed, the effect of resveratrol on BMSCs is SIRT1-dependent and ectopic SIRT1 enhances colony-forming capacity in both wild-type and Zmpste24$^{-/-}$ BMSCs. It is likely that the lifespan extension in Zmpste24$^{-/-}$ mice by resveratrol is attributable, at least in part, to the rescue of SIRT1-dependent ASC decline, e.g. BMSCs and HSCs etc. Since SIRT1 affects multiple pathways (Lavu et al., 2008; Smith et al., 2008), it is not clear which downstream targets of SIRT1 influence the maintenance of BMSCs in Zmpste24$^{-/-}$ mice. However, Foxo3a-mediated oxidative detoxification would be one potential candidate because directly scavenging ROS level via N-acetyl Cysteine (NAC) rescued the decline in BMSCs and HSCs and extended lifespan to a similar extent as resveratrol did (FIG. 10). Although lifespan extension in *C. elegans* and *Drosophila* by ectopic Sir2 was recently called into question, SIRT1 deficiency in mammals may affect metabolic and transcriptional adaptation essential for life in response to stress (Burnett et al., 2011; Chalkiadaki and Guarente, 2012; Houtkooper et al., 2012; Lombard et al., 2011; Viswanathan and Guarente, 2011). In this regard, it should be emphasized that lifespan extension in progeroid mice by resveratrol may be the consequence of elevated SIRT1-dependent physiological and metabolic functions necessary for healthspan that are severely compromised in Zmpste24$^{-/-}$ mice. Resveratrol prolongs lifespan and delays aging-related phenotypes in a short-lived fish strain (Valenzano et al., 2006).

The present invention shows that (i) resveratrol activates SIRT1 via increasing its binding to lamin A; (ii) a perturbed interaction between SIRT1 and A-type lamins compromises SIRT1 function, leading to impaired ASC population which contributes, at least partially, to some of the phenotypes associated with HGPS; (iii) resveratrol facilitates the interaction between SIRT1 and A-types lamins to activate SIRT1, and therefore, rescuing ASC decline, ameliorating progeroid phenotypes and extending lifespan in a mouse model of progeria. The present invention shows that resveratrol directly targets SIRT1. Also, resveratrol and other SIRT1 activators can be used in the treatment of HGPS.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

REFERENCES

Agarwal, B., and Baur, J. A. (2011). Resveratrol and life extension Ann N Y Acad Sci 1215, 138-143.

Alcendor, R. R., Gao, S., Zhai, P., Zablocki, D., Holle, E., Yu, X., Tian, B., Wagner, T., Vatner, S. F., and Sadoshima, J. (2007). Sirt1 regulates aging and resistance to oxidative stress in the heart. Circ Res 100, 1512-1521.

Banks, A. S., Kon, N., Knight, C., Matsumoto, M., Gutierrez-Juarez, R., Rossetti, L., Gu, W., and Accili, D. (2008). SirT1 gain of function increases energy efficiency and prevents diabetes in mice. Cell Metab 8, 333-341.

Barger, J. L., Kayo, T., Pugh, T. D., Prolla, T. A., and Weindruch, R. (2008). Short-term consumption of a resveratrol-containing nutraceutical mixture mimics gene expression of long-term caloric restriction in mouse heart. Experimental gerontology 43, 859-866.

Deng, C. X. (2009). SIRT1, is it a tumor promoter or tumor suppressor? International journal of biological sciences 5, 147-152.

Baur, J. A. (2010). Biochemical effects of SIRT1 activators. Biochim Biophys Acta 1804, 1626-1634.

Baur, J. A., Pearson, K. J., Price, N. L., Jamieson, H. A., Lerin, C., Kalra, A., Prabhu, V. V., Allard, J. S., Lopez-Lluch, G., Lewis, K., et al. (2006). Resveratrol improves health and survival of mice on a high-calorie diet. Nature 444, 337-342.

Beher, D., Wu, J., Cumine, S., Kim, K. W., Lu, S. C., Atangan, L., and Wang, M. (2009). Resveratrol is not a direct activator of SIRT1 enzyme activity. Chemical biology & drug design 74, 619-624.

Blencowe, B. J., Nickerson, J. A., Issner, R., Penman, S., and Sharp, P. A. (1994). Association of nuclear matrix antigens with exon-containing splicing complexes. J Cell Biol 127, 593-607.

Bordone, L., Cohen, D., Robinson, A., Motta, M. C., van Veen, E., Czopik, A., Steele, A. D., Crowe, H., Marmor, S., Luo, J., et al. (2007). SIRT1 transgenic mice show phenotypes resembling calorie restriction. Aging Cell 6, 759-767.

Borra, M. T., Smith, B. C., and Denu, J. M. (2005). Mechanism of human SIRT1 activation by resveratrol. J Biol Chem 280, 17187-17195.

Brunet, A., Sweeney, L. B., Sturgill, J. F., Chua, K. F., Greer, P L., Lin, Y., Tran, H., Ross, S. E., Mostoslaysky, R., Cohen, H. Y., et al. (2004). Stress-dependent regulation of FOXO transcription factors by the SIRT1 deacetylase. Science 303, 2011-2015.

Burnett, C., Valentini, S., Cabreiro, F., Goss, M., Somogyvari, M., Piper, M. D., Hoddinott, M., Sutphin, G L., Leko, V., McElwee, J. 1., et al. (2011). Absence of effects of Sir2 overexpression on lifespan in C. elegans and Drosophila. Nature 477, 482-485.

Burtner, C. R., and Kennedy, B. K (2010). Progeria syndromes and ageing: what is the connection? Nat Rev Mol Cell Biol 11, 567-578.

Candelario, J., Sudhakar, S., Navarro, S., Reddy, S., and Comai, L. (2008). Perturbation of wild-type lamin A metabolism results in a progeroid phenotype. Aging Cell 7, 355-367.

Canto, C., Gerhart-Hines, Z., Feige, J. N., Lagouge, M., Noriega, L., Milne, J. C., Elliott, P. J., Puigserver, P., and Auwerx, J. (2009). AMPK regulates energy expenditure by modulating NAD+ metabolism and SIRT1 activity. Nature 458, 1056-1060.

Cao, K., Blair, C. D., Faddah, D. A., Kieckhaefer, J. E., Olive, M., Erdos, M. R., Nabel, E. G, and Collins, F. S. (2011). Progerin and telomere dysfunction collaborate to trigger cellular senescence in normal human fibroblasts. J Clin Invest 121, 2833-2844.

Capell, B. C., Erdos, M. R., Madigan, J. P., Fiordalisi, J. J., Varga, R., Conneely, K N., Gordon, L. B., Der, C. J., Cox, A. D., and Collins, F. S. (2005) Inhibiting farnesylation of progerin prevents the characteristic nuclear blebbing of Hutchinson-Gilford progeria syndrome. Proc Natl Acad Sci USA 102, 12879-12884.

Chalkiadaki, A., and Guarente, L. (2012). Sirtuins mediate mammalian metabolic responses to nutrient availability. Nature reviews Endocrinology.

Chen, D., Steele, A. D., Lindquist, S., and Guarente, L. (2005). Increase in activity during calorie restriction requires Sirt1. Science 310, 1641.

Cheng, H. L., Mostoslaysky, R., Saito, S., Manis, J. P., Gu, Y., Patel, P., Bronson, R., Appella, E., Alt, F. W., and Chua, K. F. (2003). Developmental defects and p53 hyperacetylation in Sir2 homolog (SIRT1)-deficient mice. Proc Natl Acad Sci USA 100, 10794-10799.

Dai, H., Kustigian, L., Carney, D., Case, A., Considine, T., Hubbard, B. P., Perni, R. B., Riera, T. V., Szczepankiewicz, B., Vlasuk, G P., et al. (2010). SIRT1 activation by small molecules: kinetic and biophysical evidence for direct interaction of enzyme and activator. J Biol Chem 285, 32695-32703.

Denu, J. M. (2005). The Sir 2 family of protein deacetylases. Curr Opin Chem Biol 9, 431-440.

Donmez, G., and Guarente, L. (2010). Aging and disease: connections to sirtuins. Aging Cell 9, 285-290.

Downes, M., Ordentlich, P., Kao, H. Y., Alvarez, J. G, and Evans, R. M. (2000). Identification of a nuclear domain with deacetylase activity. Proc Natl Acad Sci USA 97, 10330-10335.

Eriksson, M., Brown, W. T., Gordon, L. B., Glynn, M. W., Singer, J., Scott, L., Erdos, M. R., Robbins, C. M., Moses, T. Y., Berglund, P., et al. (2003). Recurrent de novo point mutations in lamin A cause Hutchinson-Gilford progeria syndrome. Nature 423, 293-298.

Espada, J., Varela, I., Flores, I., Ugalde, A. P., Cadinanos, J., Pendas, A. M., Stewart, C. L., Tryggvason, K., Blasco, M. A., Freije, J. M., et al. (2008). Nuclear envelope defects cause stem cell dysfunction in premature-aging mice. J Cell Biol 181, 27-35.

Fey, E. G, Bangs, P., Sparks, C., and Odgren, P. (1991). The nuclear matrix: defining structural and functional roles. Crit Rev Eukaryot Gene Expr 1, 127-143.

Finkel, T., Deng, C. X., and Mostoslaysky, R. (2009). Recent progress in the biology and physiology of sirtuins. Nature 460, 587-591.

Fong, L. G, Frost, D., Meta, M., Qiao, X., Yang, S. H., Coffinier, C., and Young, S. G (2006). A protein farnesyltransferase inhibitor ameliorates disease in a mouse model of progeria. Science 311, 1621-1623.

Fong, L. G, Ng, J. K, Meta, M., Cote, N., Yang, S. H., Stewart, C. L., Sullivan, T., Burghardt, A., Majumdar, S., Reue, K., et al. (2004). Heterozygosity for Lmna deficiency eliminates the progeria-like phenotypes in Zmpste24-deficient mice. Proc Natl Acad Sci USA 101, 18111-18116.

Gledhill, J. R., Montgomery, M. G., Leslie, A. G., and Walker, J. E. (2007). Mechanism of inhibition of bovine F1-ATPase by resveratrol and related polyphenols. Proc Natl Acad Sci USA 104, 13632-13637.

Glynn, M. W., and Glover, T. W. (2005). Incomplete processing of mutant lamin A in Hutchinson-Gilford progeria leads to nuclear abnormalities, which are reversed by farnesyltransferase inhibition. Hum Mol Genet 14, 2959-2969.

Goodarzi, A. A., Noon, A. T., Deckbar, D., Ziv, Y, Shiloh, Y, Lobrich, M., and Jeggo, P. A. (2008). ATM signaling facilitates repair of DNA double-strand breaks associated with heterochromatin. Molecular cell 31, 167-177.

Gu, W., and Roeder, R. G. (1997). Activation of p53 sequence-specific DNA binding by acetylation of the p53 C-terminal domain. Cell 90, 595-606.

Haigis, M. C., and Sinclair, D. A. (2010). Mammalian sirtuins: biological insights and disease relevance. Annual review of pathology 5, 253-295.

Han, M. K., Song, E. K., Guo, Y, Ou, X., Mantel, C., and Broxmeyer, H. E. (2008). SIRT1 regulates apoptosis and Nanog expression in mouse embryonic stem cells by controlling p53 subcellular localization. Cell Stem Cell 2, 241-251.

Harikumar, K B., and Aggarwal, B. B. (2008). Resveratrol: a multitargeted agent for age-associated chronic diseases. Cell Cycle 7, 1020-1035.

Hawley, S. A., Ross, F A., Chevtzoff, C., Green, K A., Evans, A., Fogarty, S., Towler, M. C., Brown, L. J., Ogunbayo, O. A., Evans, A. M., et al. (2010). Use of cells expressing gamma subunit variants to identify diverse mechanisms of AMPK activation. Cell Metab 11, 554-565.

Hendzel, M. J., Delcuve, G. P., and Davie, J. R. (1991). Histone deacetylase is a component of the internal nuclear matrix. J Biol Chem 266, 21936-21942.

Herranz, D., Munoz-Martin, M., Canamero, M., Mulero, F, Martinez-Pastor, B., Fernandez-Capetillo, O., and Serrano, M. (2010). Sirt1 improves healthy ageing and protects from metabolic syndrome-associated cancer. Nature communications 1, 3.

Houtkooper, R. H., Pirinen, E., and Auwerx, J. (2012). Sirtuins as regulators of metabolism and healthspan. Nat Rev Mol Cell Biol.

Howitz, K. T., Bitterman, K. J., Cohen, H. Y., Lamming, D. W., Lavu, S., Wood, J. G., Zipkin, R. E., Chung, P., Kisielewski, A., Zhang, L. L., et al. (2003). Small molecule activators of sirtuins extend *Saccharomyces cerevisiae* lifespan. Nature 425, 191-196.

Kaeberlein, M., McDonagh, T., Heltweg, B., Hixon, J., Westman, E. A., Caldwell, S. D., Napper, A., Curtis, R., DiStefano, P. S., Fields, S., et al. (2005). Substrate-specific activation of sirtuins by resveratrol. J Biol Chem 280, 17038-17045.

Kim, E. J., Kho, J. H., Kang, M. R., and Um, S. J. (2007). Active regulator of SIRT1 cooperates with SIRT1 and facilitates suppression of p53 activity. Mol Cell 28, 277-290.

Kim, J. E., Chen, J., and Lou, Z. (2008). DBC1 is a negative regulator of SIRT1. Nature 451, 583-586.

Klar, A. J., Fogel, S., and Macleod, K (1979). MAR1-a Regulator of the HMa and HMalpha Loci in *SACCHAROMYCES CEREVISIAE*. Genetics 93, 37-50.

Krishnan, V., Chow, M. Z., Wang, Z., Zhang, L., Liu, B., Liu, X., and Zhou, Z. (2011). Histone H4 lysine 16 hypoacetylation is associated with defective DNA repair and premature senescence in Zmpste24-deficient mice. Proc Natl Acad Sci USA 108, 12325-12330.

Kruhlak, M. J., Lever, M. A., Fischle, W., Verdin, E., Bazett-Jones, D. P., and Hendzel, M. J. (2000). Reduced mobility of the alternate splicing factor (ASF) through the nucleoplasm and steady state speckle compartments. J Cell Biol 150, 41-51.

Kudlow, B. A., Stanfel, M. N., Burtner, C. R., Johnston, E. D., and Kennedy, B. K. (2008). Suppression of proliferative defects associated with processing-defective lamin A mutants by hTERT or inactivation of p53. Mol Biol Cell 19, 5238-5248.

Lavu, S., Boss, O., Elliott, P. J., and Lambert, P. D. (2008). Sirtuins—novel therapeutic targets to treat age-associated diseases. Nat Rev Drug Discov 7, 841-853.

Lee, H., Kim, K. R., Noh, S. J., Park, H. S., Kwon, K. S., Park, B. H., Jung, S. H., Youn, H. J., Lee, B. K., Chung, M. J., et al. (2011). Expression of DBC1 and SIRT1 is associated with poor prognosis for breast carcinoma. Hum Pathol 42, 204-213.

Li, L., Wang, L., Wang, Z., Ho, Y., McDonald, T., Holyoake, T. L., Chen, W., and Bhatia, R. (2012). Activation of p53 by SIRT1 inhibition enhances elimination of CML leukemia stem cells in combination with imatinib. Cancer Cell 21, 266-281.

Li, W., Chen, H. Y., and Davie, J. R. (1996). Properties of chicken erythrocyte histone deacetylase associated with the nuclear matrix. Biochem J 314 (Pt 2), 631-637.

Lin, F., and Worman, H. J. (1993). Structural organization of the human gene encoding nuclear lamin A and nuclear lamin C. J Bioi Chem 268, 16321-16326.

Liu, B., Wang, J., Chan, K. M., Tjia, W. M., Deng, W., Guan, X., Huang, J. D., Li, K. M., Chau, P. Y., Chen, D. J., et al. (2005). Genomic instability in laminopathy-based premature aging. Nat Med 11, 780-785.

Liu, B., and Zhou, Z. (2008). Lamin A/C, laminopathies and premature ageing. Histol Histopathol 23, 747-763.

Liu, Y., Wang, Y., Rusinol, A. E., Sinensky, M. S., Liu, J., Shell, S. M., and Zou, Y (2008). Involvement of xeroderma pigmentosum group A (XPA) in progeria arising from defective maturation of prelamin A. FASEB J 22, 603-611.

Lombard, D. B., Pletcher, S. D., Canto, C., and Auwerx, J. (2011). Ageing: longevity hits a roadblock. Nature 477, 410-411.

Manju, K., Muralikrishna, B., and Parnaik, V. K. (2006). Expression of disease-causing lamin A mutants impairs the formation of DNA repair foci. J Cell Sci 119, 2704-2714.

Mantel, C. R., Wang, R. H., Deng, C., and Broxmeyer, H. E. (2008). Sirt1, notch and stem cell "age asymmetry". Cell Cycle 7, 2821-2825.

McBurney, M. W., Yang, X., Jardine, K., Hixon, M., Boekelheide, K., Webb, J. R., Lansdorp, P. M., and Lemieux, M. (2003). The mammalian SIR2alpha protein has a role in embryogenesis and gametogenesis. Mol Cell Biol 23, 38-54.

McClintock, D., Ratner, D., Lokuge, M., Owens, D. M., Gordon, L. B., Collins, F. S., and Djabali, K. (2007). The mutant form of lamin A that causes Hutchinson-Gilford progeria is a biomarker of cellular aging in human skin. PLoS One 2, e1269.

Mendez, J., and Stillman, B. (2000). Chromatin association of human origin recognition complex, cdc6, and minichromosome maintenance proteins during the cell cycle: assembly of prereplication complexes in late mitosis. Mol Cell Biol 20, 8602-8612.

Milne, J. C., Lambert, P. D., Schenk, S., Carney, D. P., Smith, J. J., Gagne, D. J., Jin, L., Boss, O., Perni, R. B., Vu, C. B., et al. (2007). Small molecule activators of SIRT1 as therapeutics for the treatment of type 2 diabetes. Nature 450, 712-716.

Pacholec, M., Bleasdale, J. E., Chrunyk, B., Cunningham, D., Flynn, D., Garofalo, R. S., Griffith, D., Griffor, M., Loulakis, P., Pabst, B., et al. (2010). SRT1720, SRT2183, SRT1460, and resveratrol are not direct activators of SIRT1. J Biol Chem 285, 8340-8351.

Park, S. J., Ahmad, F., Philp, A., Baar, K., Williams, T., Luo, H., Ke, H., Rehmann, H., Taussig, R., Brown, A. L., et al. (2012). Resveratrol ameliorates aging-related metabolic phenotypes by inhibiting cAMP phosphodiesterases. Cell 148, 421-433.

Pendas, A. M., Zhou, Z., Cadinanos, J., Freije, J. M., Wang, J., Hultenby, K., Astudillo, A., Wernerson, A., Rodriguez, F., Tryggvason, K., et al. (2002). Defective prelamin A processing and muscular and adipocyte alterations in Zmpste24 metalloproteinase-deficient mice. Nat Genet 31, 94-99.

Pfluger, P. T., Herranz, D., Velasco-Miguel, S., Serrano, M., and Tschop, M. H. (2008). Sirt1 protects against high-fat diet-induced metabolic damage. Proc Natl Acad Sci USA 105, 9793-9798.

Phair, R. D., and Misteli, T. (2000). High mobility of proteins in the mammalian cell nucleus. Nature 404, 604-609.

Picard, F., Kurtev, M., Chung, N., Topark-Ngarm, A., Senawong, T., Machado De Oliveira, R., Leid, M., McBurney, M. W., and Guarente, L. (2004). Sirt1 promotes fat mobilization in white adipocytes by repressing PPAR-gamma. Nature 429, 771-776.

Price, N. L., Gomes, A. P., Ling, A. J., Duarte, F. V., Martin-Montalvo, A., North, B. J., Agarwal, B., Ye, L., Ramadori, G., Teodoro, J. S., et al. (2012). SIRT1 is required for AMPK activation and the beneficial effects of resveratrol on mitochondrial function. Cell Metab 15, 675-690.

Rodgers, J. T., Lerin, C., Haas, W., Gygi, S. P., Spiegelman, B. M., and Puigserver, P. (2005). Nutrient control of glucose homeostasis through a complex of PGC-1alpha and SIRT1. Nature 434, 113-118.

Rusinol, A. E., and Sinensky, M. S. (2006). Farnesylated lamins, progeroid syndromes and farnesyl transferase inhibitors. J Cell Sci 119, 3265-3272.

Ryan, R. F., Schultz, D. C., Ayyanathan, K., Singh, P. B., Friedman, J. R., Fredericks, W. J., and Rauscher, F. J., 3rd (1999). KAP-1 corepressor protein interacts and colocalizes with heterochromatic and euchromatic HP1 proteins: a potential role for Kruppel-associated box-zinc finger proteins in heterochromatin-mediated gene silencing. Molecular and cellular biology 19, 4366-4378.

Saunders, L. R., Sharma, A. D., Tawney, J., Nakagawa, M., Okita, K., Yamanaka, S., Willenbring, H., and Verdin, E. (2010). miRNAs regulate SIRT1 expression during mouse embryonic stem cell differentiation and in adult mouse tissues. Aging (Albany N.Y.) 2, 415-431.

Scaffidi, P., and Misteli, T. (2005). Reversal of the cellular phenotype in the premature aging disease Hutchinson-Gilford progeria syndrome. Nat Med 11, 440-445.

Scaffidi, P., and Misteli, T. (2006). Lamin A-dependent nuclear defects in human aging. Science 312, 1059-1063.

Scaffidi, P., and Misteli, T. (2008). Lamin A-dependent misregulation of adult stem cells associated with accelerated ageing. Nat Cell Biol 10, 452-459.

Sgambato, A., Ardito, R., Faraglia, B., Boninsegna, A., Wolf, F. I., and Cittadini, A. (2001). Resveratrol, a natural phenolic compound, inhibits cell proliferation and prevents oxidative DNA damage. Mutat Res 496, 171-180.

Smith, B. C., Hallows, W. C., and Denu, J. M. (2008). Mechanisms and molecular probes of sirtuins. Chem Biol 15, 1002-1013.

Sun, C., Zhang, F., Ge, X., Yan, T., Chen, X., Shi, X., and Zhai, Q. (2007). SIRT1 improves insulin sensitivity under insulin-resistant conditions by repressing PTP1B. Cell Metab 6, 307-319.

Timmers, S., Konings, E., Bilet, L., Houtkooper, R. H., van de Weijer, T., Goossens, G. H., Hoeks, J., van der Krieken, S., Ryu, D., Kersten, S., et al. (2011). Calorie restriction-like effects of 30 days of resveratrol supplementation on energy metabolism and metabolic profile in obese humans. Cell Metab 14, 612-622.

Tissenbaum, H. A., and Guarente, L. (2001). Increased dosage of a sir-2 gene extends lifespan in *Caenorhabditis elegans*. Nature 410, 227-230.

Toth, J. I., Yang, S. H., Qiao, X., Beigneux, A. P., Gelb, M. H., Moulson, C. L., Miner, J. H., Young, S. G., and Fong, L. G. (2005). Blocking protein farnesyltransferase improves nuclear shape in fibroblasts from humans with progeroid syndromes. Proc Natl Acad Sci USA 102, 12873-12878.

Valenzano, D. R., Terzibasi, E., Genade, T., Cattaneo, A., Domenici, L., and Cellerino, A. (2006). Resveratrol prolongs lifespan and retards the onset of age-related markers in a short-lived vertebrate. Current biology: CB 16, 296-300.

Varela, I., Cadinanos, J., Pendas, A. M., Gutierrez-Femandez, A., Folgueras, A. R., Sanchez, L. M., Zhou, Z., Rodriguez, F. J., Stewart, C. L., Vega, J. A., et al. (2005). Accelerated ageing in mice deficient in Zmpste24 protease is linked to p53 signalling activation. Nature 437, 564-568.

Varela, I., Pereira, S., Ugalde, A. P., Navarro, C. L., Suarez, M. F., Cau, P., Cadinanos, J., Osorio, F. G., Foray, N., Cobo, J., et al. (2008). Combined treatment with statins and aminobisphosphonates extends longevity in a mouse model of human premature aging. Nat Med 14, 767-772.

Villalba, J. M., de Cabo, R., and Alcain, F. J. (2012). A patent review of sirtuin activators: an update. Expert opinion on therapeutic patents 22, 355-367.

Viswanathan, M., and Guarente, L. (2011). Regulation of *Caenorhabditis elegans* lifespan by sir-2.1 transgenes. Nature 477, E1-2.

Viswanathan, M., Kim, S. K., Berdichevsky, A., and Guarente, L. (2005). A role for SIR-2.1 regulation of ER stress response genes in determining *C. elegans* life span. Developmental cell 9, 605-615.

Wang, R. H., Sengupta, K., Li, C., Kim, H. S., Cao, L., Xiao, C., Kim, S., Xu, X., Zheng, Y, Chilton, B., et al. (2008). Impaired DNA damage response, genome instability, and tumorigenesis in SIRT1 mutant mice. Cancer Cell 14, 312-323.

Wood, J. G., Rogina, B., Lavu, S., Howitz, K., Helfand, S. L., Tatar, M., and Sinclair, D. (2004). Sirtuin activators mimic caloric restriction and delay ageing in metazoans. Nature 430, 686-689.

Zhao, W., Kruse, J. P., Tang, Y., Jung, S. Y., Qin, J., and Gu, W. (2008). Negative regulation of the deacetylase SIRT1 by DBC1. Nature 451, 587-590.

What is claimed is:

1. A method for modulating the deacetylase activity of NAD-dependent deacetylase sirtuin-1 (SIRT1) in a mammalian stem cell present in a mammal, the method comprising modifying the binding affinity of lamin A to SIRT1 in the mammalian cell by administering to the mammal an effective amount of a composition that modifies the binding affinity of lamin A to SIRT1, wherein the composition comprises a carboxyl terminal peptide of lamin A consisting of amino acids 570 to 664 of SEQ ID NO:2 or a functional fragment thereof.

2. The method of claim 1, wherein the deacetylase activity of SIRT1 is increased by an increased binding affinity of lamin A to SIRT1.

3. The method according to claim 1, wherein the mammalian stem cell is an adult stem cell (ASC) or a mesenchymal stem cell (MSC).

4. A method for treating an ASC decline or an MSC decline in a mammal, the method comprising administering to the mammal an effective amount of a composition that increases the binding affinity of lamin A to SIRT1 in the ASCs or the MSCs of the mammal, wherein the composition comprises a carboxyl terminal peptide of lamin A consisting of amino acids 570 to 664 of SEQ ID NO:2 or a functional fragment thereof.

* * * * *